United States Patent
Hong et al.

(10) Patent No.: US 12,194,027 B2
(45) Date of Patent: Jan. 14, 2025

(54) SMALL MOLECULE INHIBITORS OF GPCR GPR68 AND RELATED RECEPTORS FOR TREATING CANCER, GLIOBLASTOMA, AND OTHER INDICATIONS

(71) Applicant: UNIVERSITY OF MARYLAND, BALTIMORE, Baltimore, MD (US)

(72) Inventors: Charles C. Hong, Baltimore, MD (US); Charles H. Williams, Odenton, MD (US); Latur Ravithej Singh, Hyderabad (IN)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 572 days.

(21) Appl. No.: 17/602,101

(22) PCT Filed: Apr. 17, 2020

(86) PCT No.: PCT/US2020/028651
§ 371 (c)(1),
(2) Date: Oct. 7, 2021

(87) PCT Pub. No.: WO2020/214896
PCT Pub. Date: Oct. 22, 2020

(65) Prior Publication Data
US 2022/0202785 A1 Jun. 30, 2022

Related U.S. Application Data

(60) Provisional application No. 62/835,016, filed on Apr. 17, 2019.

(51) Int. Cl.
*A61K 31/433* (2006.01)
*A61K 31/495* (2006.01)
(Continued)

(52) U.S. Cl.
CPC .......... *A61K 31/433* (2013.01); *A61K 31/495* (2013.01); *A61K 31/56* (2013.01); *A61K 45/06* (2013.01); *A61P 35/00* (2018.01)

(58) Field of Classification Search
CPC .............. A61K 2300/00; A61K 31/433; A61K 31/4439; A61K 31/4709; A61K 31/495;
(Continued)

(56) References Cited

U.S. PATENT DOCUMENTS

| | | |
|---|---|---|
| 2015/0210717 A1 | 7/2015 | Gunes et al. |
| 2015/0315211 A1 | 11/2015 | Walensky et al. |

FOREIGN PATENT DOCUMENTS

| | | |
|---|---|---|
| CN | 106800566 A | 6/2017 |
| WO | 2005/092304 A2 | 10/2005 |
| WO | 2007/146138 A2 | 12/2007 |

OTHER PUBLICATIONS

Falconer, S. B. et al., "Supporting information", May 26, 2015, pp. S1-S22, XP093004574, Retrieved from the Internet: URL:https://pubs.acs.org/doi/10.1021/acsinfecdis.5b00033.
(Continued)

*Primary Examiner* — Savitha M Rao
(74) *Attorney, Agent, or Firm* — Wolter Van Dyke Davis, PLLC; Eugene J. Molinelli; Martha Cassidy

(57) ABSTRACT

The invention relates to a class of small molecule inhibitors of GPR68/OGR1, a proton-sensing/stretch-sensing/sheer-stress-sending G-protein coupled receptor, and related receptors GPR4 and GPR65. These inhibitors are useful as a therapeutic for glioblastoma and other neoplasms, as a monotherapy or adjuvant, and also can be used as a treatment for other conditions, such as osteoporosis, inflammatory bowel disease, autoimmune and chronic inflammatory diseases such as multiple sclerosis and inflammatory pain syndromes, GERD, aspiration pneumonitis, bacterial and
(Continued)

viral pneumonia, COPD, acute respiratory distress syndrome (ARDS), and COVID-19.

5 Claims, 52 Drawing Sheets

(51) Int. Cl.
    *A61K 31/56*     (2006.01)
    *A61K 45/06*     (2006.01)
    *A61P 35/00*     (2006.01)
(58) Field of Classification Search
    CPC ...... A61K 31/56; A61K 45/06; C07D 513/10; A61P 11/00; A61P 11/06; A61P 19/10; A61P 29/00; A61P 3/10; A61P 35/00; A61P 37/00; A61P 9/00
    See application file for complete search history.

(56) References Cited

OTHER PUBLICATIONS

Falconer, S. B. et al., "Zinc Chelation by a Small-Molecule Adjuvant Potentiates Meropenem Activity in Vivo against NDM-1-Producing Klebsiella pneumoniae", Acs Infectious Diseases, vol. 1, No. 11, May 26, 2015, pp. 533-543.
International Preliminary Report on Patentability received for PCT Patent Application No. PCT/US20/28651, mailed on Jun. 16, 2021, 7 pages.
International Search Report and Written Opinion received for PCT Patent Application No. PCT/US20/28651, mailed on Sep. 21, 2020, 12 pages.
Liu, H. Q. et al., "Synthesis and biological evaluation of 5'-phenyl-3'H-spiro-[indoline-3,2'-[1,3,4] oxadiazol]-2", Chinese Chemical Letters, vol. 24, No. 10, Jul. 2, 2013, pp. 929-933.
Supplementary European search report and Search Opinion Received for EP Application No. 20791442.5, mailed on Dec. 14, 2022, 13 pages.
Williams, C. H. et al., "Coupling Metastasis to pH-Sensing GPR68 Using a Novel Small Molecule Inhibitor", bioRxiv, Apr. 17, 2019, pp. 1-33.
Dr. Massimo Milani, et al.; "Efficacy of betamethasone valerate 1.0% thermophobic foam in seborrhoeic dermatitis of the scalp: an open-label, multicentre, prospective trial on 180 patients"; Journal Current Medical Research and Opinion; vol. 19, 2003—Issue 4; 4pp.
PubChem Compound Summary; 5'-Naphthalen-1-ylspiro[1H-indole-3,2'-3H-1,3,4-thiadiazole]-2-one; 2018; 8pp.
Steven N. Reuland, et al.; "The Combination of BH3-Mimetic ABT-737 with the Alkylating Agent Temozolomide Induces Strong Synergistic Killing of Melanoma Cells Independent of p53"; PLoS ONE, Aug. 2011, vol. 6, Issue 8; 10pp.
Charles H. Williams III; "Chemical genetics of Vertebrate development"; Dissertation; May 2017; 80pp.

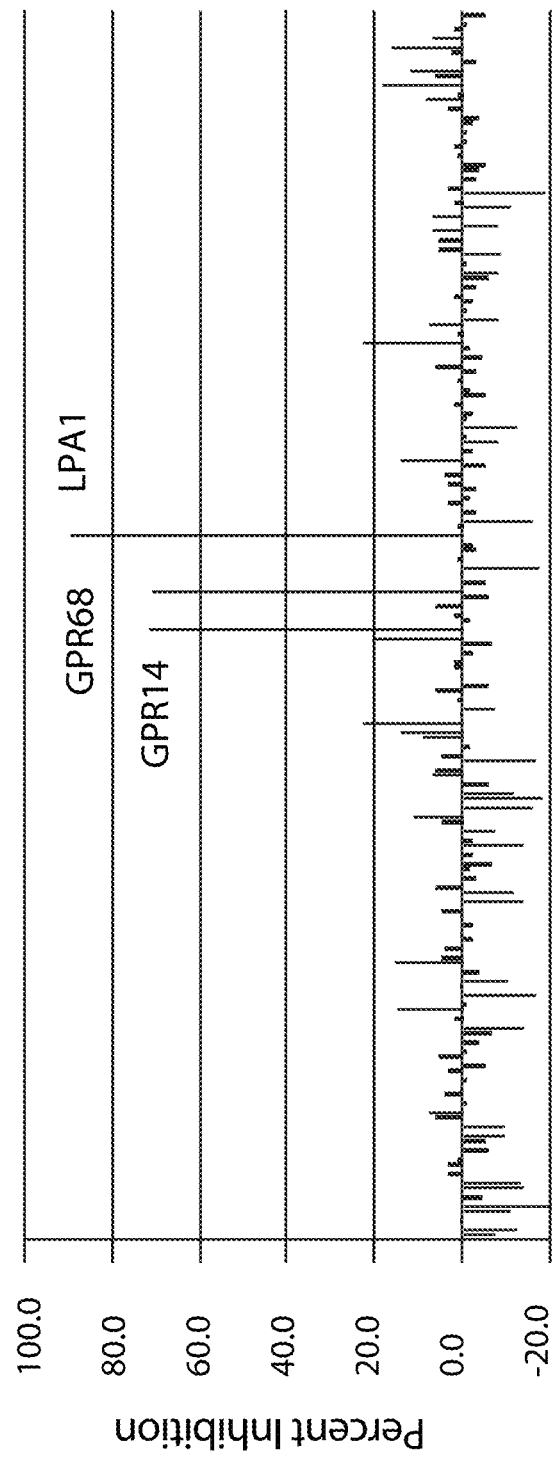

FIG. 9A

| Variant | Consequence | Het Carriers count (UKB) | Homo Carriers (UKB) |
|---|---|---|---|
| rs141731950 | A124A | 863 | 0 |
| rs150575263 | A281A | 7916 | 27 |
| rs2540862 | R183R | 9077 | 656 |
| rs61745752 | E336X | 700 | 0 |

FIG. 9B

| Algorithm | Prediction/score |
|---|---|
| DANN Mutation | 0.9949 Disease Causing |
| Taster | |
| FATHMM_MKL | Damaging |
| EIGEN | Pathogenic |
| LRT | Neutral |

FIG. 9C

| ICD10 Code | Description |
|---|---|
| C433 | Malignant melanoma of other and unspecified parts of face |
| C61 | Malignant neoplasm of prostate |
| C786 | Secondary malignant neoplasm of retroperitoneum and peritoneum |
| D127 | Benign neoplasm of rectosigmoid junction |
| D179 | Benign lipomatous neoplasm, unspecified |
| D261 | Other benign neoplasm of corpus uteri |

FIG. 9D

| CODE | Variant | Odd Ratio | Upper 95% CI | Lower 95% CI |
|------|---------|-----------|--------------|--------------|
| C433 | rs141731950 | NA | NA | NA |
| C433 | rs150575263 | 1.22 | 3.27 | 0.45 |
| C433 | rs2540862 | 0.29 | 0.89 | 0.09 |
| C433 | rs61745752 | 5.60 | 22.58 | 1.39 |
| C61 | rs141731950 | 0.65 | 1.30 | 0.32 |
| C61 | rs150575263 | 0.93 | 1.13 | 0.76 |
| C61 | rs2540862 | 1.01 | 1.23 | 0.83 |
| C61 | rs61745752 | 1.75 | 2.70 | 1.13 |
| C786 | rs141731950 | 0.34 | 2.43 | 0.05 |
| C786 | rs150575263 | 0.83 | 1.27 | 0.55 |
| C786 | rs2540862 | 0.80 | 1.24 | 0.51 |
| C786 | rs61745752 | 2.43 | 5.13 | 1.15 |
| D127 | rs141731950 | NA | NA | NA |
| D127 | rs150575263 | 0.54 | 1.44 | 0.20 |
| D127 | rs2540862 | 0.43 | 1.33 | 0.14 |
| D127 | rs61745752 | 3.71 | 11.59 | 1.19 |
| D179 | rs141731950 | 1.58 | 11.24 | 0.22 |
| D179 | rs150575263 | 1.23 | 2.61 | 0.58 |
| D179 | rs2540862 | 1.94 | 3.63 | 1.03 |
| D179 | rs61745752 | 4.79 | 14.96 | 1.53 |
| D261 | rs141731950 | NA | NA | NA |
| D261 | rs150575263 | 1.65 | 4.46 | 0.61 |
| D261 | rs2540862 | 2.24 | 5.45 | 0.92 |
| D261 | rs61745752 | 7.45 | 30.09 | 1.84 |

FIG. 10A

PREDICTED ARRESTIN BINDING DOMAIN

| | | | | | | | | | | | | | | | | |
|---|---|---|---|---|---|---|---|---|---|---|---|---|---|---|---|---|
| Rhodopsin | 329 | G | D | D | A | S | A | pT | V | - | pS | K | T | E | T | S | Q | V |
| Vasopressin2 | 350 | S | L | G | Q | E | E | pS | C | pT | pT | A | S | pS | L | A | K |
| GPR68 | 331 | P | P | G | P | E | A | pS | G | K | pS | G | A | Q | G | E | E | E |
| Re1745752 | 331 | P | L | G | P | X | | | | | | | | | | | | |

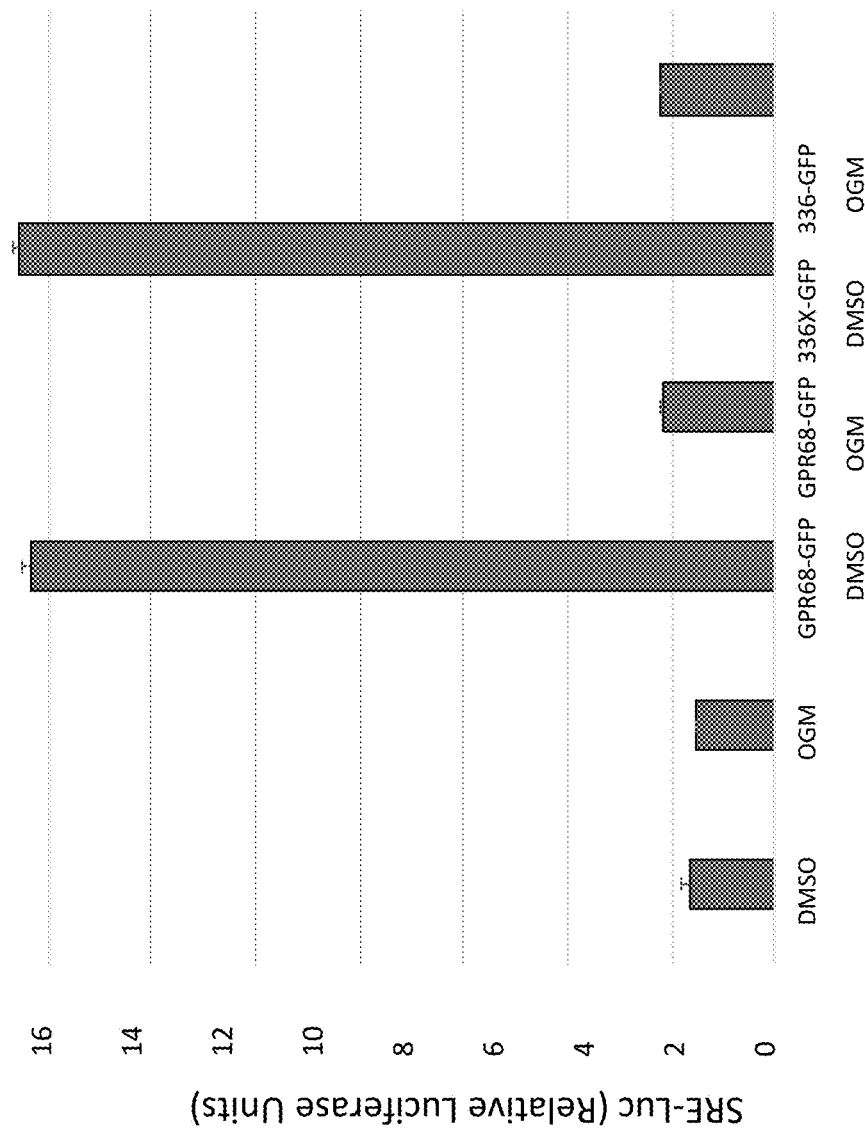

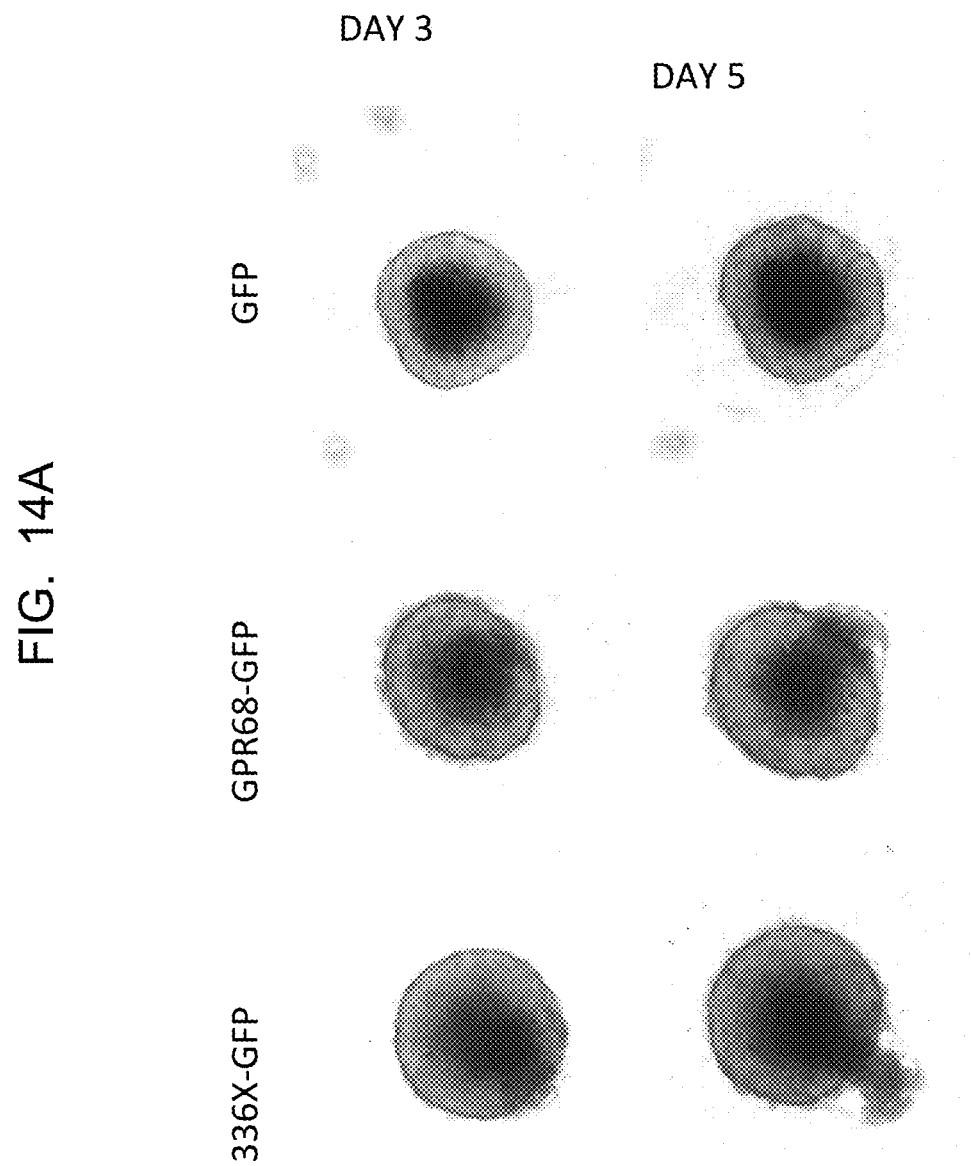

FIG. 20A
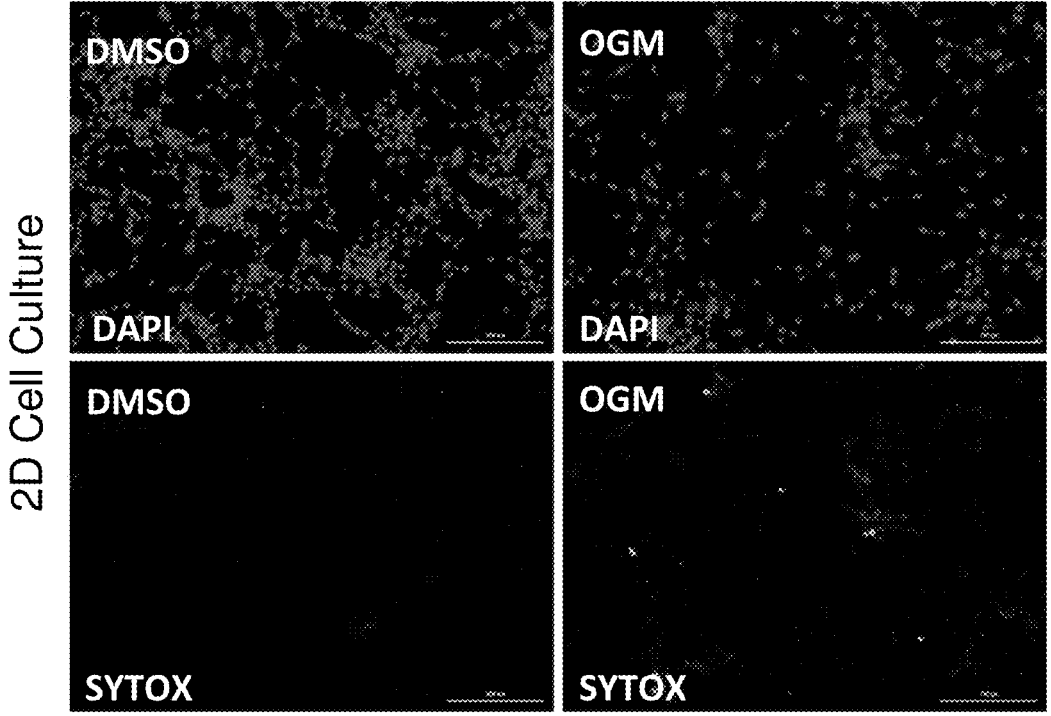
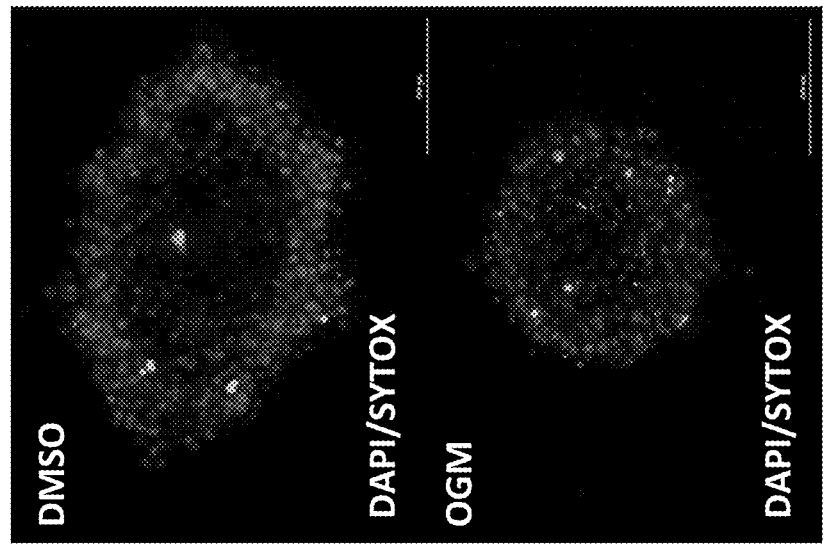
FIG. 20B

FIG. 28C
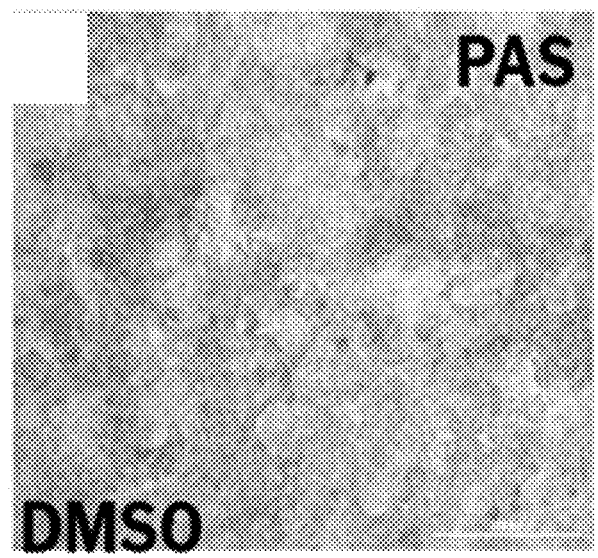
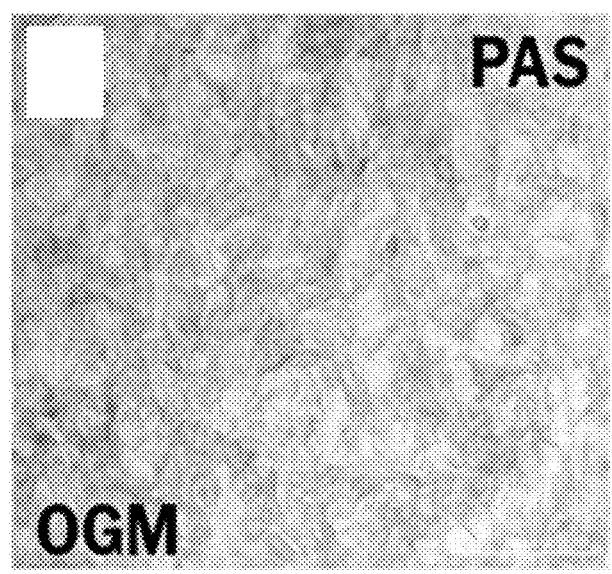
FIG. 28D

SMALL MOLECULE INHIBITORS OF GPCR GPR68 AND RELATED RECEPTORS FOR TREATING CANCER, GLIOBLASTOMA, AND OTHER INDICATIONS

CROSS-REFERENCE TO RELATED APPLICATIONS

This application is a national stage entry of and claims priority to PCT/US2020/028651, filed Apr. 17, 2020, which claims the benefit of U.S. provisional application Ser. No. 62/835,016, filed Apr. 17, 2019. The entire contents of this application is hereby incorporated by reference as if fully set forth herein.

GOVERNMENT FUNDING SUPPORT

This invention was made with government support under grant no. GM118557 awarded by the National Institutes of Health. The government has certain rights in the invention.

BACKGROUND

1. Field of the Invention

The invention relates generally to the field of medicine and in particular a novel class of small molecule inhibitors of GPR68/OGR1 and their therapeutic use for treating cancer, glioblastoma, cardiology indications, and other conditions as a monotherapy or as an adjuvant in combination with other therapeutic agents. The inhibitors are of the 1,2-dihydro-3'H-spiro[indole-3,2'-(1,3,4}thiadiazole]-2-one class of compounds.

2. Background of the Invention

Acidic milieu is a hallmark of glycolytic metabolism which occurs in cancerous cells. The effect of an acidic environment on cancer progression can be categorized into effects on tumor cell survival, tumor metastasis, inflammatory response, and blood vessels. Yet the underlying signaling and cell biological underpinnings of these phenomena are not well understood.

Highly malignant, invasive, and metastatic cancers have markedly elevated glycolytic activity, producing an oncologically favorable acidotic extracellular environment; a phenomenon called the Warburg effect (Vander Heiden et al., 2009). This acidification (pHe<7.4) of the environment is marked by increases in efflux mechanisms H+ATPases and Na+-H+ exchangers (Martinez-Zaguilan et al., 1993; Martínez-Zaguilán et al., 1998; McLean et al., 2000; Sennoune et al., 2004). Acidification promotes tumor malignancy, including metabolic reprogramming and invasiveness. Investigations have shown that in numerous animal models of solid tumors, small molecule inhibition of NHE1 can have an effect on tumor growth and metastasis (Matthews et al., 2011), however the cellular mechanisms triggered by the acidification of the tumor environment are still not wholly understood.

Asthma exacerbation is often triggered by airway acidification. This can be caused by exogenous factors such as air pollution as well as by endogenous factors such as gastroesophageal reflux disease (GERD). There are major processes in asthma pathogenesis: (1) mucous hyperproduction, (2) bronchoconstriction, and (3) inflammation. The inflammation is highly characteristic of an abnormal immune response, highly skewed toward the arm of the immune system commonly called "Th2" or "type 2" immunity. There are particular cell types involved in the immune response including innate immune cells called "eosinophils" and antigen presenting cells called "dendritic cells" or "DCs'" as well as particular cytokines that include, but are not limited to, IL-4, IL-5, and IL-13 (1). Asthma severity has been shown to correlate with the pH of induced sputum samples. In other words, the less well-controlled the asthma, the lower the sputum pH. Furthermore, poor asthma control also is correlated with an increased percentage of eosinophils in sputum samples. The proton-sensing molecule, GPR68, is implicated in all cardinal pathogenic processes in asthma.

Aspiration pneumonia is a leading cause of pneumonia in the intensive care unit and is one of the leading risk factors for acute lung injury (ALI) and acute respiratory distress syndrome (ARDS). Patients placed on a ventilator are particularly susceptible to aspiration pneumonia. The mechanisms underlying the impact of acid aspiration on lung inflammation are poorly understood. The main pathologic characteristics of acid aspiration-induced lung injury include increased permeability of the alveolus-capillary interface, interstitial inflammation, and edema that eventually fills the alveolar air sacs, which are also consistent with the pathology of ARDS. Hypoxia is a hallmark of lung injury and hypoxia and ultimately leads to activation of hypoxia-inducible factor (HIF)-1 alpha (7). HIF-1alpha plays a central role in the inflammation caused by acid aspiration characterized by an accumulation alveolar macrophages, neutrophils, and increased permeability via type II alveolar epithelial cells (i.e. the cells that produce surfactant).

Hypoxia and inflammation are interconnected and linked in multiple ways and may induce and influence each other. Inflammation may be hypoxia-driven or hypoxia may be induced by inflammation (inflammatory hypoxia). Hypoxia not only maintains or aggravates inflammation via stabilization of HIF-1alpha but can also lower the local tissue pH. This acidic environment is not only the result of inflammation, but also affects the degree and outcome of inflammation. Inflammation has been attributed to an increase in local proton concentration and lactate production and has also been linked to subsequent proinflammatory cytokine production, including TNF-alpha, IL-1 beta, IL-6, and interferon-gamma. Thus, hypoxia, inflammation, and low pH can create a pathological feedforward loop.

Hypoxia also positively regulates the expression of GPR68, as demonstrated in surgical resection specimens from subjects with inflammatory bowel disease (IBD). In particular, GPR68 is directly upregulated on intestinal submucosal macrophages in IBD compared to normal control in specimens incubated in a hypobaric chamber. In addition, HIF-1 alpha binds to the GPR68 promoter under the hypoxic conditions. Thus, it appears that hypoxia leads to a local acidic microenvironment and causes up-regulation of GPR68 via HIF-1 alpha-induced transcription, which in turn drives mucosal inflammation.

Disruption of the positive feed forward pathologic loop that results from gastric acid aspiration and that subsequently leads to ARDS, by inhibiting GPR68, is an attractive and logical therapeutic strategy. Thus, an inhibitor or antagonist of GPR68 could be administered to a mammal, including a human subject with COPD, especially with aspiration, in an amount effective to prevent or to attenuate ALI/ARDS, including chronic sequelae such as lung fibrosis.

SUMMARY OF THE INVENTION

The invention relates to a class of small molecule inhibitors of GPR68/OGR1, a proton-sensing/stretch-sensing/ sheer-stress-sending G-protein coupled receptor, and related receptors GPR4 and GPR65. These inhibitors are useful as a therapeutic for glioblastoma and other neoplasms, as a monotherapy or adjuvant, and also can be used as a treatment for other conditions, such as osteoporosis, inflammatory bowel diseases, autoimmune and chronic inflammatory diseases, such as multiple sclerosis, and inflammatory pain syndromes. asthma, chronic obstructive pulmonary disease, aspiration pneumonia, viral pneumonia, coronavirus pneumonia and lung injury, acute lung injury (ALI), acute respiratory distress syndrome (ARDS), diabetes type 1, osteoporosis, inflammatory bowel disease, chronic inflammatory disease, atherosclerosis, cardiovascular disease, multiple sclerosis, inflammatory pain syndrome, and autoimmune disease.

Specifically, embodiments of the invention include a method of treating or preventing a malignancy in a mammalian subject in need thereof, comprising administering to the subject a therapeutic 1,2-dihydro-3'H-spiro[indole-3,2'-[1,3,4]thiadiazole]-2-one agent of Formula I or a salt thereof:

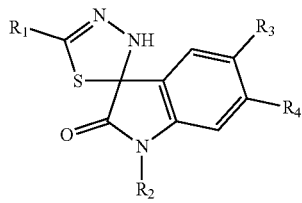

wherein $R_1$ is an optionally substituted

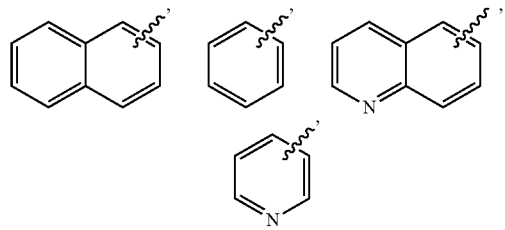

wherein the substitution is selected from —H, —CH$_3$, —CH$_2$CH$_3$, —OCH$_3$, —Br, —F, and —CF$_3$; wherein $R_2$ is —H or —CH$_3$; and wherein $R_3$ and $R_4$ independently are —H, —CH$_3$, —CH$_2$CH$_3$, —OCH$_3$, —CN, —F, —COOCH$_3$, —COOH, —SO$_2$NH$_2$. Preferred compounds are selected from the group consisting of

OGM6

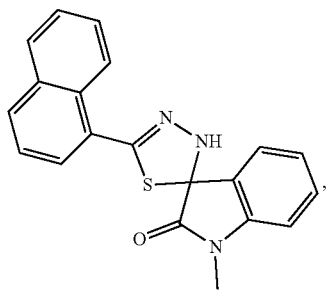

OGM2

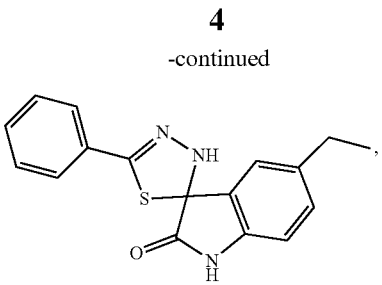

OGM5

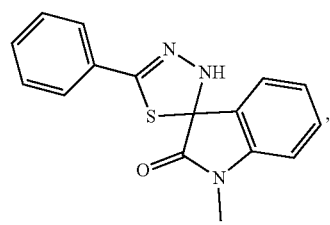

OGM1

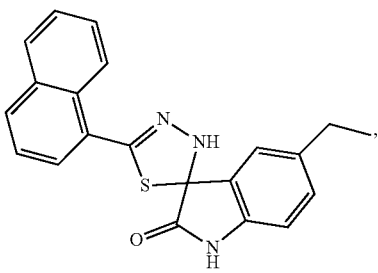

OGM3

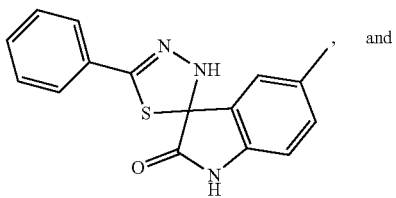

, and

OGM4

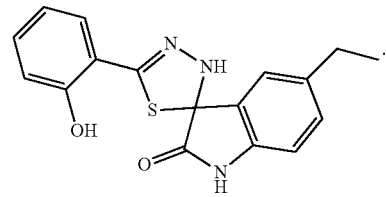

preferably, the compound is

OGM1

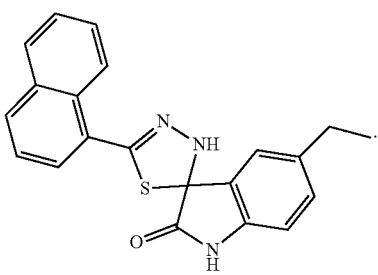

In certain embodiments, the malignancy is selected from the group consisting of glioblastoma, medulloblastoma, neuroendocrine prostate cancer, melanoma, skin cancer, breast cancer, ovarian cancer, kidney cancer, and lung cancer. In other embodiments, the method further comprises administering to the mammalian subject in need thereof at least one additional therapeutic agent, for example an anticancer agent such as Temozolomide.

In another embodiment, the invention involves a method of treating or preventing an autoimmune/inflammatory condition in a mammalian subject in need thereof, comprising administering to the subject a therapeutic 1,2-dihydro-3'H-spiro[indole-3,2'-[1,3,4]thiadiazole]-2-one agent of Formula I or a salt thereof:

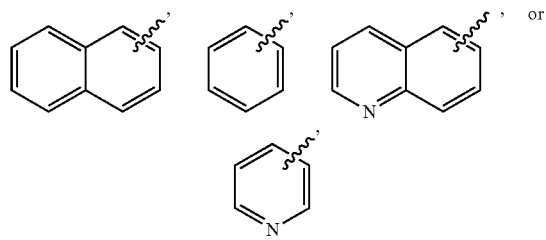

wherein $R_1$ is an optionally substituted

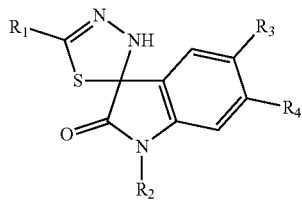

wherein the substitution is selected from —H, —CH$_3$, —CH$_2$CH$_3$, —OCH$_3$, —Br, —F, and —CF$_3$; wherein $R_2$ is —H or —CH$_3$; and wherein $R_3$ and $R_4$ independently are —H, —CH$_3$, —CH$_2$CH$_3$, —OCH$_3$, —CN, —F, —COOCH$_3$, —COOH, —SO$_2$NH$_2$.

Preferred compounds are selected from the group consisting of

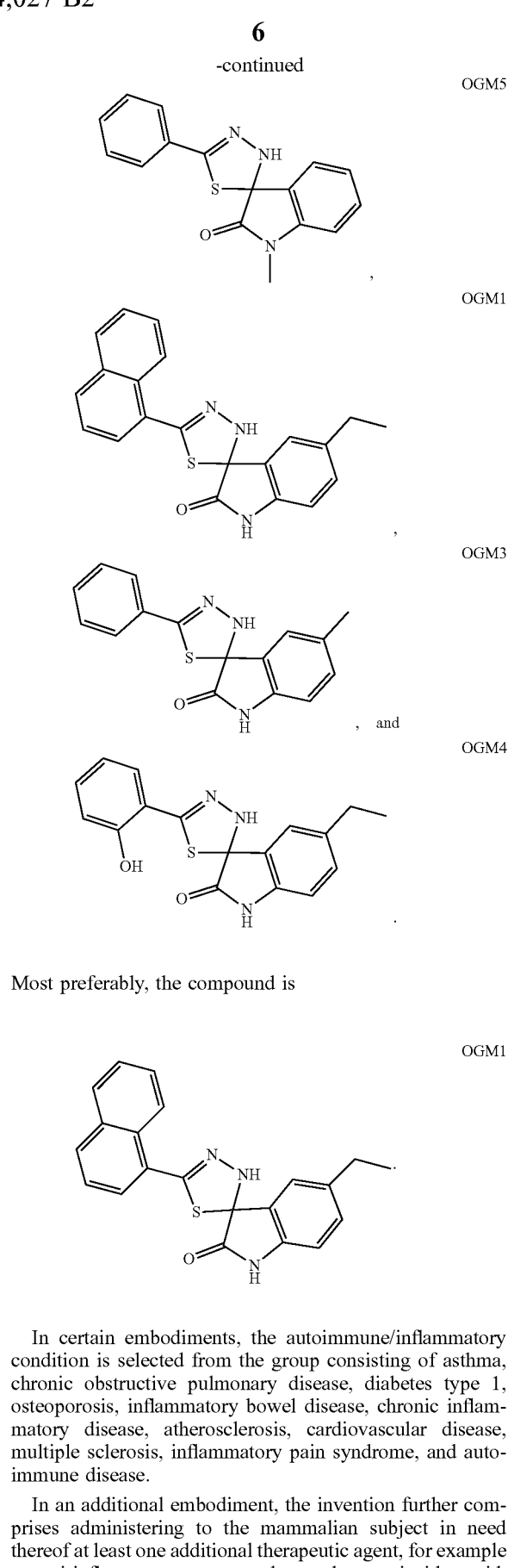

Most preferably, the compound is OGM1

In certain embodiments, the autoimmune/inflammatory condition is selected from the group consisting of asthma, chronic obstructive pulmonary disease, diabetes type 1, osteoporosis, inflammatory bowel disease, chronic inflammatory disease, atherosclerosis, cardiovascular disease, multiple sclerosis, inflammatory pain syndrome, and autoimmune disease.

In an additional embodiment, the invention further comprises administering to the mammalian subject in need thereof at least one additional therapeutic agent, for example an anti-inflammatory agent, such as a glucocorticoid steroid.

In certain embodiments, the invention comprises a method for inhibiting GPR68 in a mammalian subject in need thereof comprising administering to the subject a therapeutic 1,2-dihydro-3'H-spiro[indole-3,2'-[1,3,4]thiadiazole]-2-one agent of Formula I or a salt thereof:

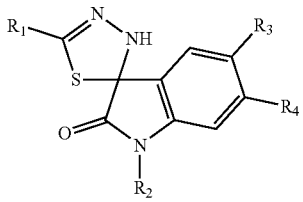

wherein R₁ is an optionally substituted

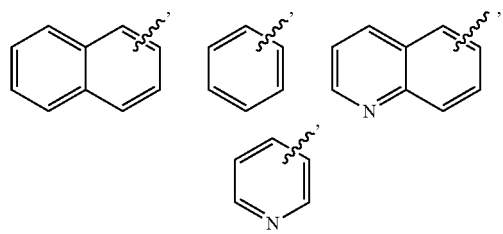

wherein the substitution is selected from —H, —CH₃, —CH₂CH₃, —OCH₃, —Br, —F, and —CF₃; wherein R₂ is —H or —CH₃; and wherein R₃ and R₄ independently are —H, —CH₃, —CH₂CH₃, —OCH₃, —CN, —F, —COOCH₃, —COOH, —SO₂NH₂. Preferred compounds are selected from the group consisting of

OGM6

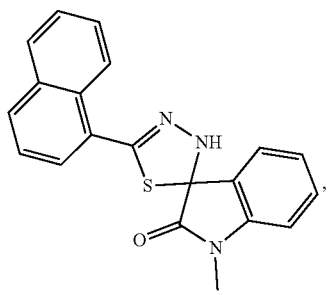

OGM2

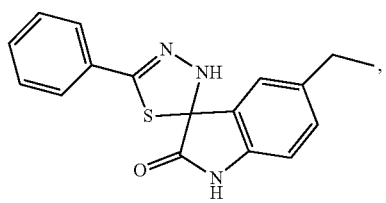

OGM5

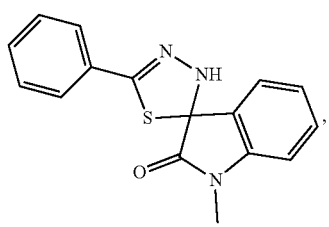

OGM1

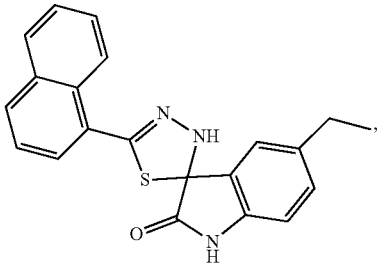

OGM3

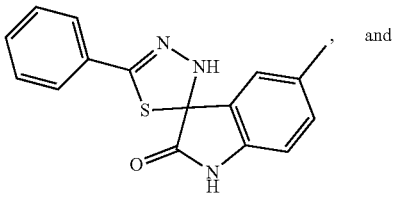

OGM4

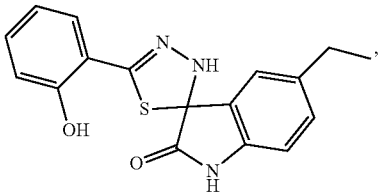

Most preferably, the compound is

OGM1

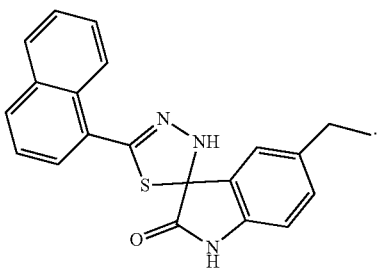

The invention also comprises, in some embodiments, a therapeutic 1,2-dihydro-3'H-spiro[indole-3,2'-[1,3,4]thiadiazole]-2-one agent of Formula I or a salt thereof:

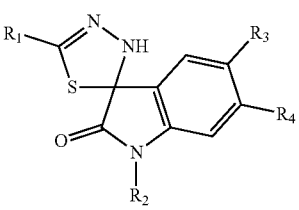

wherein R₁ is an optionally substituted

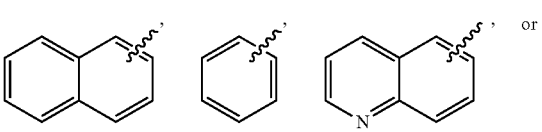

-continued

wherein the substitution is selected from —H, —CH₃, —CH₂CH₃, —OCH₃, —Br, —F, and —CF₃; wherein R₂ is —H or —CH₃; and wherein R₃ and R₄ independently are —H, —CH₃, —CH₂CH₃, —OCH₃, —CN, —F, —COOCH₃, —COOH, —SO₂NH₂, more preferably a therapeutic agent selected from the group consisting of

OGM6

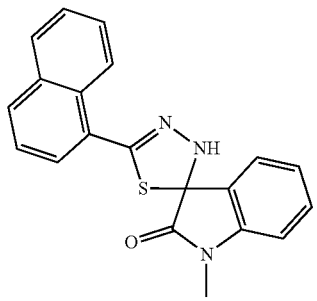

OGM2

OGM5

OGM1

OGM3

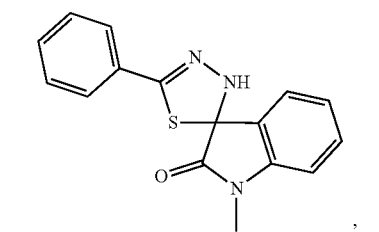

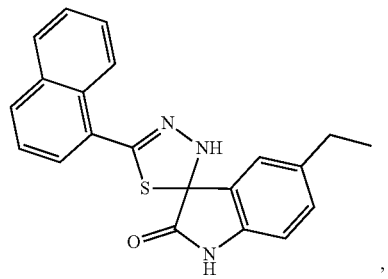

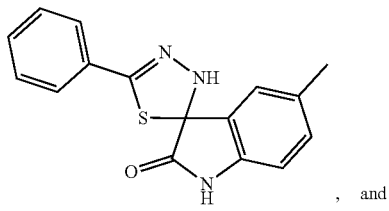, and

-continued

OGM4

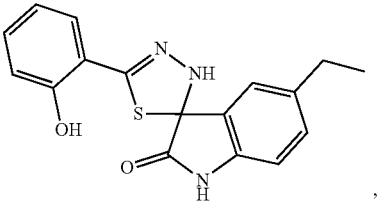

and most preferably the therapeutic agent

OGM1

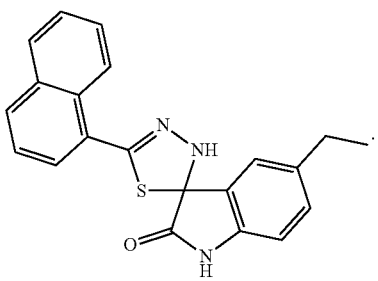

The invention specifically includes the above methods, wherein the subject in need suffers from a condition selected from the group consisting of a malignancy, GERD, aspiration pneumonitis, COPD, ARDS, and COVID-19.

The invention also includes as certain embodiments, pharmaceutical compositions comprising a pharmaceutically acceptable carrier and the therapeutic agents discussed above and herein.

BRIEF SUMMARY OF THE DRAWINGS

FIG. 1A provides the structure of Ogremorphin (5-ethyl-5'-naphthalen-1-ylspiro[1H-indole-3,2'-3H-1,3,4-thiadiazole]-2-one. FIG. 1B shows a dorsal view of a DMSO vehicle control-treated zebrafish embryo at 48 hours pf. FIG. 1C shows a dorsal view of an OGM (10 μM) treated zebrafish embryo at 48 hours pf. FIG. 1D provides a temporal phenotypic analysis for the perturbation of pigmentation. FIG. 1E provides a lateral view of zebrafish after in situ hybridization of FOXD3 on the left side, and a magnification inset on the right side. Arrows point to positive staining along the dorsal ridge of the embryo.

FIG. 2A through FIG. 2D. OGM is a reversible inhibitor of GPR68. FIG. 2A shows the results of a Millipore™ GPCRome screen. FIG. 2B shows the core scaffold for OGM derivatives according to embodiments of the invention. FIG. 2C shows recovery of response to stimulus after removal of inhibitor. FIG. 2D Shows representative dose response assay of Ogremorphin analog OGM-2.

FIG. 3A is a graph showing HNMR spectra confirming resynthesis of OGM2. FIG. 3B is a graph showing LCMS spectra confirming resynthesis of OGM2.

FIG. 4A: top=control; middle=OGM treatment;

middle=morphant. FIG. 4B, FIG. 4C, and FIG. 4D are bar graphs showing quantitation of the phenotypes present in percentage of treated embryos.

FIG. 5A is a graph showing overall survival of glioblastoma over time. FIG. 5B is a graph presenting data inhibition of calcium flux response to acidification by OGM-2.

FIG. 6A and FIG. 6B. OGM inhibits human melanoma migration. FIG. 6A shows that OGM and EIPA both prevent wound closure compared to DMSO (CTL). FIG. 6B is a bar graph showing results from quantitation of inhibition of scratch assay across three melanoma lines.

FIG. 7 is a photograph of a gel showing WM115, MeWo, and A2058, as indicated.

FIG. 8A is a schematic of an agarose drop assay. FIG. 8B, FIG. 8C, FIG. 8D, FIG. 8E, and FIG. 8F are photographs of agarose gel plates. FIG. 8G is a bar graphs that presents data from quantitation of the cells that escaped from an average of 5 gel drop replicates.

FIG. 9A through FIG. 9D. GPR68 variant Rs61745752 associated with oncological signals including metastasis. FIG. 9A show number of heterozygous and homozygous synonymous 'silent' mutations and stop gain variant carriers in the imputed UK Biobank dataset. FIG. 9B are the results of functional outcome algorithm for Rs61745752 showing 4/5 predicting a deleterious or pathogenic consequence. FIG. 9C shows highlighted neoplasm ICD10 codes. FIG. 9D show increased association of Stop gain variant rs61745752 with both benign and malignant neoplasm ICD10 codes, while silent mutations do not share the same associations.

FIG. 10A through FIG. 10D. Variant Rs61745752 is a functional c-terminal truncation. FIG. 10A is a phosphocode prediction of beta-arrestin binding site downstream of amino acid 335. The figure shows SEQ ID NO:1 (rhodopsin), SEQ ID NO:2 (vasopressin 2), SEQ ID NO:3 (GPR68) and SEQ ID NO:4 (rs61745752). FIG. 10B is a set of photographs of GPR68-GFP and 336X-GFP transfected HEK293 cells. GPR68-GFP and 336X-GFP transfected HEK293 cells have no significant receptor internalization under unstimulated conditions. Upon stimulation with pH6.8 media for 5 minutes. GPR68-GFP had puncta (white arrows) in the cell, 336X-GFP did not form puncta under acidic conditions FIG. 10C is a bar graph presenting data from quantitation of the number of puncta in each cell. FIG. 10D Shows calcium flux assay of truncation variant in transfected HEK293 cells showing elevated calcium levels.

FIG. 11 is a bar graph presenting a composite of results from a serum responsive element (SRE-) luciferase assay.

FIG. 12. OGM still able to inhibit GPR68 activation in truncation variant. FIG. 12 is a bar graph.

FIG. 13A, FIG. 13B, and FIG. 13C are Kaplan-Mier plots generated in cBioportal of the breast cancer cohort carrying alterations in GPR68 (FIG. 13A), and alterations in members of the same protein family, alterations in GPR4 (FIG. 13B), and alterations in GPR65 (FIG. 13C).

FIG. 14A through FIG. 14D. GPR68 activity destabilized MCF7 spheroids. FIG. 14A is a set of photographs of MCF7 cells transfected with GFP, GPR68-GFP, and 336X-GFP, seeded in Ultra low attachment plates to form spheroids. FIG. 14B presents data from quantitation of the number of spheroids without intact outer rings. FIG. 14C is a bar graph presenting data from quantitation of the size of the out-growth from spheroids. FIG. 14D is a set of photographs allowing visualization of GFP+ cells in spheroids.

FIG. 15A is a set of representative photographs of control and OGM-treated cells. FIG. 15B shows quantitation of these data in graph form.

FIG. 17A and FIG. 17B are graphs showing growth attenuation in TMZ sensitive (FIG. 17A) and insensitive (FIG. 17B) glioblastoma models.

FIG. 18A and FIG. 18B are graphs showing growth attenuation in both TMZ sensitive (FIG. 18A) and insensitive (FIG. 18B) glioblastoma models.

FIG. 19A is a photograph of tumor spheroids treated with DMSO, or OGM. FIG. 19B is a graph showing growth stimulation in 3D tumoroid culture in glioblastoma models over time when treated with DMSO, Ogerin or OGM.

FIG. 20A and FIG. 20B. GPR68 inhibition increases cell death. FIG. 20A is a set of photographs showing 2D cancer cell assays. FIG. 20B is a set of photographs showing 3D tumor spheroid assays.

FIG. 21A is a set of photographs showing treated tumor spheroids. FIG. 21B is a bar graph showing data for tumor spheroids treated at the indicated pH.

FIG. 22 is a photograph of a six-well plate containing U87 cells treated with increasing concentrations of OGM2.

FIG. 23 is a graph showing cells treated with OGM2 at the indicated concentrations.

FIG. 24A is a graph showing the effect of high doses of OGM on PAN02 pancreatic cancer cells. FIG. 24B is a set of photographs showing reduction of migration by OGM in PAN02 pancreatic cancer cells. FIG. 24C is a photograph of a six-well plate containing PANC02 cells treated with increasing concentrations of OGM2.

FIG. 25A is a graph showing the effect of high doses of OGM on A549 lung cancer cells. FIG. 25B is a photograph of a six-well plate containing A549 cells treated increasing concentrations of OGM2.

FIG. 26A is a graph showing that lower GPR68 expression correlates to better prognosis of multiple cancer cell types. FIG. 26B is a graph showing that OGM2 reduces the viability of Prostate and breast cancer cells.

FIG. 27A is a graph showing data for viability of U87 cells treated with increasing concentrations of TMZ, with or without OGM2. FIG. 27B is a set of photographs of wells containing irradiated PANC02 cells treated with OGM2.

FIG. 28A through FIG. 28F. OGM inhibits acid induced Mucin production. FIG. 28A and FIG. 28B are dot blots and corresponding western blots to detect Mucin-5AC and alpha tubulin, respectively. FIG. 28A shows that acidification increases Mucin production.

FIG. 28B shows that OGM inhibits Mucin production. FIG. 28C and FIG. 28D are photomicrographs showing A549 cells in culture stained to detect mucins. FIG. 28E is a schematic of cas9 mediated endogenous tagging of MU5AC genetic locus with nano-luciferase in A549 cells. FIG. 28F is a bar graph showing data for Muc5ac-Luc cell lysates assayed for luciferase activity.

FIG. 29 is a drawing showing negative effects of GPR68 activation in certain pulmonary disease conditions.

DETAILED DESCRIPTION

1. Definitions

Figure 1A:
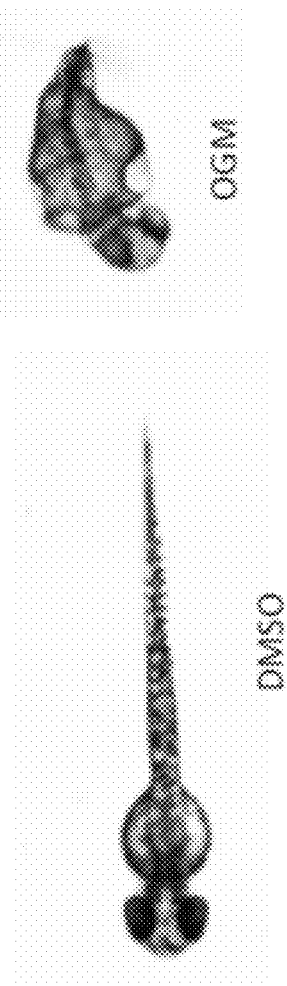
FIG. 1A through FIG. 1E. Discovery of Ogremorphin (OGM).

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

The term "about," as used herein, means plus or minus 20 percent of the recited value, so that, for example, "about 0.125" means 0.125±0.025, and "about 1.0" means 1.0±0.2.

As used herein, the term "subject" or "patient" refers to any mammal (preferably a human) which is diagnosed with a malignancy or an autoimmune/inflammatory condition, is suspected of suffering from a malignancy or an autoimmune/inflammatory condition, or is at risk for developing a malignancy or an autoimmune/inflammatory condition.

As used herein, the term "mammal" refers to any mammalian species, including humans, laboratory animals, zoo animals, farm animals, companion animals, service animals, and the like. In particular, humans, and animals such as apes, monkeys, rodents, bovines, equines, caprines, canines, felines are included in the definition of "mammal" as known in the art of biology.

As used herein, the terms "treating," "treatment," and their cognates, refers to an action taken to obtain a desired pharmacologic and/or physiologic therapeutic effect. "Treatment," therefore, includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; (c) relieving, alleviating or ameliorating the condition or disease or symptom thereof, such as, for example, causing regression of the condition or disease or symptom thereof, and (d) reducing the amount or frequency of standard drugs needed to treat the condition on a continuing basis.

As used herein, the terms "prevent," "prevention," and their cognates, refers to complete prevention of a disease or condition such that the disease or condition does not occur, and also includes decreasing the likelihood of a subject contracting or developing the disease or condition, causing the disease or condition to occur less frequently or with less severity in a subject or in a population, and shortening the duration of a disease or condition in a subject or a population.

As used herein, the terms "malignancy," "malignant," and "cancer" refer to a hyperproliferative disorder, disease, or condition with the presence of cancerous cells. Malignancies or cancer generally are characterized by anaplasia, invasiveness, and/or metastasis, but these do not occur in all cases. Examples of diseases and conditions falling under the definition of cancer include, but are not limited to, carcinomas, sarcomas, lymphomas and leukemias, germ cell tumors, and blastomas. Specifically included are cancers of the blood, kidney, lung, skin, pancreas, brain, breast, prostate, ovary, glioblastoma, medulloblastoma, and the like, such as neuroendocrine prostate cancer, and melanoma.

As used herein, the term "autoimmune/inflammatory condition" refers to any disease or condition known as autoimmune diseases in the art and as inflammatory diseases in the art. These two groups of conditions overlap to a degree and are grouped together here. In general, an "autoimmune disease" is a condition arising from an abnormal immune response of the body which attacks itself. Major autoimmune diseases include, celiac disease, diabetes type 1, Graves' disease, inflammatory bowel disease, multiple sclerosis, psoriasis, rheumatoid arthritis, and systemic lupus erythematosus.

Inflammatory disorders and conditions broadly are those involving inflammation and are often mediated by the immune system. Such disorders include cancer, ischemic heart disease, atherosclerosis, asthma, chronic obstructive pulmonary disease (COPD), osteoporosis, chronic inflammatory disease, inflammatory pain syndrome, celiac disease, colitis, diverticulitis, inflammatory bowel disease, hypersensitivities, rheumatic fever, rheumatoid arthritis, sarcoidosis, vasculitis, and the like. Thus, any of these type of diseases and conditions are contemplated for treatment and prevention by embodiments of this invention. In particular, autoimmune diseases such as type 1 diabetes (T1D), rheumatoid arthritis (RA) and multiple sclerosis (MS), irritable bowel disease (IBS), are part of this invention, as well as allergic conditions such as seasonal pollen allergy, pet dander or mold, or infectious or hyperproliferative disorders. For asthma, an inhibitor or antagonist of GPR68 could be administered to a mammal, including a human subject with controlled asthma, in an amount effective to reduce the likelihood of exacerbations and to reduce the amount of standard of care intranasal corticosteroids necessary for asthma control. Conditions and diseases of this type that are amenable to treatment by the invention which define an appropriate subject or patient will be discerned easily by the person of skill in the art based on the disclosures herein.

As used herein, the term "anticancer agent" refers to a therapeutic agent that has the effect of killing, decreasing the size of, preventing metastasis of, reducing metastasis of, halting the growth of, reducing the speed of growth of, or ameliorating a symptom of a cancer.

As used herein, the term "anti-inflammatory agent" refers to a therapeutic agent that has the effect of preventing, ameliorating, reducing the severity of, reducing the likelihood of, or ameliorating a symptom of an autoimmune/inflammatory condition as discussed here, particularly those relating to inflammation of/injury to the lung, and various types of pneumonia.

As used herein, the terms "administer," "administration," and their cognates, refers to contacting a subject with a therapeutic compound or composition. As used herein, "administering" and its cognates refers to introducing an agent to a subject, and can be performed using any of the various methods or delivery systems for administering agents and pharmaceutical compositions known to those skilled in the art. Modes of administering include, but are not limited to oral administration or intravenous, subcutaneous, intramuscular or intraperitoneal injections, rectal administration by way of suppositories or enema, or local administration directly into or onto a target tissue (such as the pancreas or skin), or administration by any route or method that delivers a therapeutically effective amount of the drug or composition to the cells or tissue to which it is targeted.

As used herein, the term "therapeutic agent" refers to any compound that exerts a "therapeutic effect" (or pharmaceutical composition that contains such a compound). A "therapeutic effect" is a pharmacological or physiological effect of preventing, curing, delaying, ameliorating, improving, shortening the duration of, decreasing the likelihood of, decreasing the symptoms of, and the like, a disease or condition in a subject.

2. Overview

Embodiments of this invention relate to Ogremorphin, a first-in-class inhibitor of proton-sensing GPCR GPR68. Discovered from a chemical genetic zebrafish screen, Ogremorphin perturbs neural crest migration. Furthermore, Ogremorphin inhibits migration in a number of human melanoma lines which derive from the neural crest. Phenome-wide association study identified a natural variant that is ectopically active and is associated with metastasis of common cancers. The GPR68 activity is associated with an increased ability for cancer cell migration and contributes to metastasis, making the compounds according to this invention suitable for treatment of hyperproliferative and autoimmune or chronic inflammatory conditions.

3. Embodiments of the Invention

An inhibitor of the proton-sensing GPCR (G protein-coupled receptor), GPR68, which modulates migratory behavior of melanoma cells in vitro and in vivo was identified. Targeting proton dynamics, and the dysregulation of pH has emerged as a possible therapeutic avenue for cancer and GPR68 has been implicated in the regulation of cancer in diverse and even divergent ways. GPR68, when overexpressed in PC3 prostate cancer cells has significantly reduced metastasis. Furthermore, in ovarian cancer cells HEY1, overexpression of GPR68 reduced cell migration and increased cell adhesion. However, in medulloblastoma GPR68 activation increases TRPC4 activity which enhances tumor cell migration. GPR68 has been identified as a regulator of cancer-associated fibroblasts in colon cancer and pancreatic cancer and may play a critical role in regulating cancer progression.

Figures 16A, 16B, 16C:
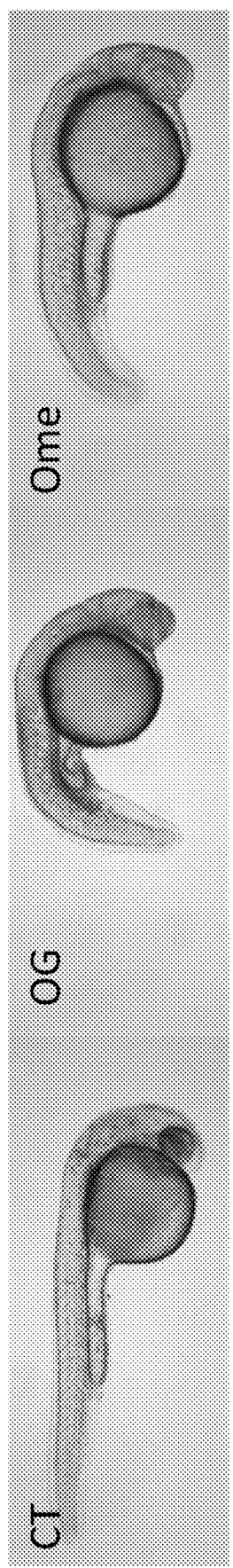
FIG. 16A through FIG. 16C. Proton efflux machinery inhibition phenocopies OGM treatment. These figure are representative images of DMSO control (FIG. 16A), OGM treatment (FIG. 16B), and omeprazole treated (FIG. 16C) embryos.

The results presented here demonstrate that Ogremorphin (OGM) is a reversible GPR68 inhibitor, a first-in-class negative regulator of this molecule. Additionally, embodiments of this invention relate to a role for GPR68 in zebrafish development. Previous studies have shown that GPR68 is expressed during the early development of zebrafish, and responds to acidification like its mammalian homolog. Inhibition of GPR68 during neural crest migration affects the development of pigmentation and craniofacial cartilage formation is demonstrated here. In Xenopus, v-atpase regulates pH in a regional manner to affect craniofacial morphogenesis; recent studies of GPR68 have shown that the receptor senses flow and stretch. However, both of these stimuli are dependent on mildly acidic conditions. While it is still not clear if GPR68 is sensing protons in neural crest cells or the surrounding tissues, this is the first data that suggests that there could be proton mediated signaling events that are critical for normal development in zebrafish. Notably, treatment of zebrafish with some proton efflux machinery phenocopies OGM treatment while others do not. See FIG. 16, which provides representative images of DMSO control (FIG. 16A), OGM treatment (FIG. 16B), and omeprazole treated (FIG. 16C) embryos.

Recent studies have focused on the mechanisms through which the acidification and pH modulation affects cancer cell behavior through proton-sensing receptors such as GPR4, GPR65, and GPR68. In both in vitro and in vivo models, acidification promotes melanoma cell migration. Consistent with this observation, the studies presented here with OGM suggest that melanoma cells sense acidification through GPR68 to modulate their migration. Furthermore, using a functional genomics approach, the data presented here show that rs61745752, which results in a truncation of the c-terminal tail of GPR68 upstream of a putative β-arrestin binding domain, causes a loss of receptor internalization and an aberrant receptor activation, and is associated with increased risk of cancer.

Preferred compounds identified here as GPCR68 inhibitors include, but are not limited to:

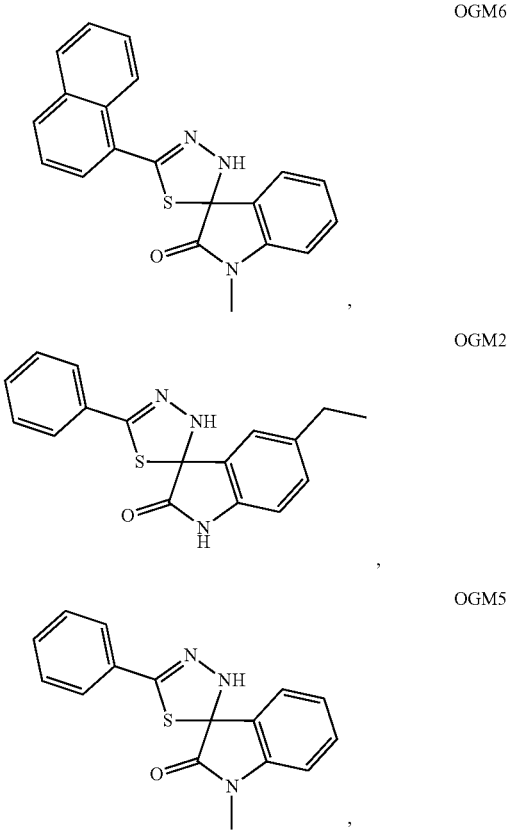

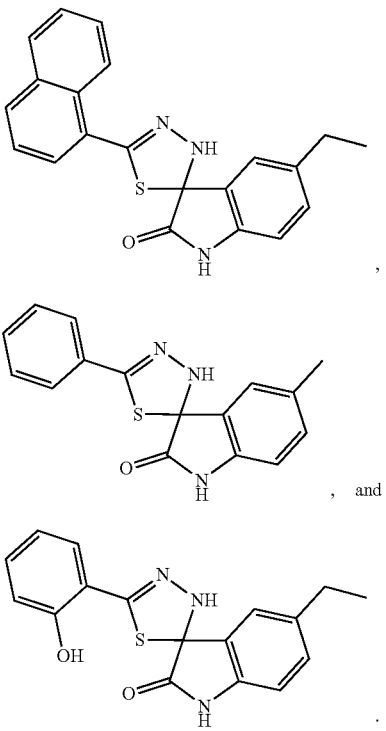

Other compounds suitable for use with embodiments of the invention are described below. Embodiments of the invention include the compounds disclosed here.

The compounds of the invention include the base, and any pharmaceutically acceptable hydrate, solvate, acid or salt, and can be amorphous or in any crystalline form, or as an oil or wax. Any pharmaceutically acceptable salt can be used, as may be convenient. Generally, these salts are derived from pharmaceutically and biologically acceptable inorganic or organic acids and bases or metals. Examples of such salts include, but are not limited to: acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts.

The compounds also include any or all stereochemical forms of the therapeutic agents (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more atom is replaced by, for example, deuterium, tritium, $^{13}C$, $^{14}C$ (or any isotopic labels as commonly used in the art such as phosphorus, calcium, iodine, chlorine, bromine, or any other convenient element for isotopic labeling) are within the scope of this invention.

Further embodiments of the invention include pharmaceutical compounds that include one or more compounds according to the invention, combined with one or more pharmaceutical carriers or vehicles as known in the art. Also, in preferred method embodiments, the compounds described herein are formulated and are administered as a pharmaceutical composition that includes a pharmaceutically acceptable carrier and one or more pharmaceutical or therapeutic agent, including one or more of the inventive compounds described herein, and optionally including one or more additional agents.

A pharmaceutically acceptable carrier refers to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art. A suitable carrier depends on the route of administration contemplated for the pharmaceutical composition. Routes of administration are determined by the person of skill according to convenience, the health and condition of the subject to be treated, and the location and stage of the condition to be treated.

Such routes can be any route which the practitioner deems to be most effective or convenient using considerations such as the patient, the patient's general condition, and the specific condition to be treated. For example, routes of administration can include, but are not limited to: local or parenteral, including: oral, intravenous, intraarterial, intrathecal, subcutaneous, intradermal, intraperitoneal, rectal, vaginal, topical, nasal, local injection, buccal, transdermal, sublingual, inhalation, transmucosal, wound covering, direct injection into a tumor or the area surrounding a tumor, and the like. The administration can be given by transfusion or infusion, and can be administered by an implant, an implanted pump, or an external pump, a nebulizer, an inhaler, or any device known in the art. Preferably, the administration according embodiments of the invention is oral, inhalation, intramuscular, topical, intratumoral, or intravenous.

Therefore, the forms which the pharmaceutical composition can take will include, but are not limited to: tablets, capsules, caplets, lozenges, dragees, pills, granules, oral solutions, powders for dilution, powders or fluids for inhalation, vapors, gases, sterile solutions or other liquids for injection or infusion, transdermal patches, buccal patches, inserts and implants, rectal suppositories, vaginal suppositories, creams, lotions, oils, ointments, topical coverings (e.g., wound coverings and bandages), suspensions, emulsions, lipid vesicles, and the like. Preferred compositions take the form of tablets, capsules, and preparations for injection or inhalation.

Treatment regimens include a single administration or a course of administrations lasting two or more days, including a week, two weeks, several weeks, a month, two months, several months, a year, or more, including administration for the remainder of the subject's life. The regimen can include multiple doses per day, one dose per day or per week, for example, or a long infusion administration lasting for an hour, multiple hours, a full day, or longer.

Dosage amounts per administration include any amount determined by the practitioner, and will depend on the size of the subject to be treated, the state of the health of the subject, the route of administration, the condition to be treated or prevented, and the like. In general, it is contemplated that for the majority of subjects, a dose in the range of about 0.01 mg/kg to about 100 mg/kg is suitable, preferably about 0.1 mg/kg to about 50 mg/kg, more preferably about 0.1 mg/kg to about 10 mg/kg, and most preferably about 0.2 mg/kg to about 5 mg/kg are useful. This dose can be administered weekly, daily, or multiple times per day. A dose of about 0.1 mg, 0.2 mg, 0.25 mg, 0.5 mg, 1 mg, 5 mg, 10 mg, 20 mg, 40 mg, 80 mg, 100 mg, 250 mg, 500 mg, or 1000 mg can be administered.

A549 lung cancer cells produce the predominant airway and lung mucin, Mucin5AC, at low pH. Inhibition of GPR68 inhibits Mucin 5AC in a dose-dependent manner. See Example 24.

In certain embodiments, the invention is contemplated for use in malignancies (cancer), as discussed. The methods of these embodiments include treatment and/or prevention of cancer, such as glioblastoma, pancreatic cancer, lung cancer, medulloblastoma, prostate cancer (e.g., neuroendocrine prostate cancer), skin cancer (e.g., melanoma), breast cancer, ovarian cancer, and kidney cancer.

GPR68 is expressed on bronchial airway epithelial cells, on bronchial airway smooth muscle cells, and on bronchial airway dendritic cells. Therefore, inhibitors or antagonists of GPR68 can be useful in asthma, in either a prophylactic context (control) or the treatment of acute exacerbations (rescue) of the disease. Furthermore, GPR inhibitors can target all three cardinal pathogenic processes in asthma. No current standard of care medication can address all three cardinal processes in asthma. In some aspects, embodiments of the invention include treatment of a subject with asthma that is poorly controlled during an exacerbation. The inhibitor or antagonist could be administered in combination with standard of care beta adrenergic agonists, anticholinergic compounds, leukotriene modulators, and/or systemic corticosteroids in an amount effective to improve pulmonary function and end the exacerbation.

Therefore, in certain other embodiments, the invention is contemplated for use in autoimmune/inflammatory disease and conditions, as discussed. Preferably, the methods of these embodiments include treatment and/or prevention of conditions such as asthma, chronic obstructive pulmonary disease (COPD), chronic bronchitis, aspiration pneumonia, viral pneumonia, coronavirus pneumonia and lung injury (e.g., COVID-19), acute lung injury (ALI), acute respiratory distress syndrome (ARDS), cystic fibrosis, osteoporosis, diabetes type 1, inflammatory bowel disease, atherosclerosis and other inflammatory cardiovascular conditions, multiple sclerosis, inflammatory pain syndrome, chronic inflammatory disease, or other autoimmune or inflammatory diseases.

One well-established experimental model of ALI/ARDS is acid (HCl) instillation into animal's lungs. In this model chemical injury of lung tissue caused by HCl incites the disease process. This model was used to interrogate the pulmonary pathogenesis of the SARS virus (SARS CoV). The SARS CoV receptor is shared by SARS CoV-2 (the etiologic agent of COVID-19), namely angiotensin converting enzyme-2 (ACE2). Recombinant SARS CoV spike protein was administered to animals with acid induced ARDS. Spike-Fc protein localized to bronchial epithelial cells, inflammatory exudates and alveolar pneumocytes. Notably, Spike-Fc primarily localized to severe lesions and SARS-CoV Spike protein enhanced the severity of acute lung injury including inflammatory infiltrates and interstitial edema.

While this study did not specifically measure oxygen levels in the mice, the pathological changes which included marked inflammatory infiltrates and interstitial edema are consistent with changes that would result in hypoxia. Thus, as with aspiration pneumonia, the model of hypoxia induced GPR68 expression derived from IBD can be applied to ARDS broadly, and specifically to coronavirus associated ARDS.

In addition, a model of hypoxia induced GPR68 expression derived from IBD can be applied to aspiration pneumonia. Aspiration of gastric acid (hydrochloric acid; HCL) causes chemical lung injury and initial inflammation. This initial inflammation leads to hypoxia and acidification of the microenvironment. HIF-1 alpha is induced and stabilized, and HIF-1 alpha binds to the GPR68 promoter, leading to transcription and translation of GPR68, which in turn exacerbates inflammation, hypoxia, and acidification. This positive feedforward loop ultimately results in ARDS.

Therefore, the invention includes administration of an inhibitor or an antagonist of GPR68 to a subject for treatment of acute lung injury/ARDS of various etiologies including but not limited to sepsis, pancreatitis, trauma, bacterial or viral pneumonia, and inhalation of toxins. This treatment can attenuate the inflammation and edema associated with these conditions, thus preventing acute respiratory failure as well as the chronic and even long-term sequelae associated with survival of ARDS, including lung fibrosis. The invention specifically includes treatment of lung injury or inflammation in a subject infected with a coronavirus, including but not limited to SARS CoV-2, to attenuate the inflammation and edema associated with these infections, to prevent acute respiratory failure, and to reduce the long-term sequelae associated with survival of ARDS, including lung fibrosis.

The invention also specifically relates to methods of treatment with an inhibitor or antagonist of GPR68 of subjects with COPD, especially with chronic bronchitis, in an amount effective to reduce airway mucous secretions.

In further embodiments, the compounds according to the invention can be administered in conjunction with the drug, Temozolomide, either in a single combined dosage form or in separate compositions to be administered sequentially or concomitantly.

The compounds according to the invention also can be administered along with other treatments such as radiation treatments.

4. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1: Methods and Materials

A. Chemical Screening

A chemical screen for small molecules that perturb dorsoventral axis was performed as previously described (see Chen et al., 2009; Hao et al., 2013; Williams et al., 2015; Yu et al., 2008)). Briefly, pairs of WT zebrafish were mated, and fertilized eggs were arrayed in 96-well microtiter plates (5 embryos/well) containing 100 1 E3 water. At 4 hours post fertilization (pf), a small molecule library from Vanderbilt High Throughput Screening Facility was added to each well to a final concentration of 10M. Embryos were incubated at 28.5 C until 24 and 48 hours pf, when they were examined for gross morphologic changes indicative of dorsalization of the embryonic axis. A total of 30,000 compounds were screened.

B. Alcian Blue Staining

Staged embryos and larvae were anesthetized with Tricaine and killed by immersion in 4% formaldehyde (prepared from paraformaldehyde, and buffered to pH 7 in phosphate-buffered saline (PBS)). The fixed animals were rinsed in acid-alcohol (0.37% HCl, 70% EtOH), and stained overnight in Alcian blue (Schilling et al., 1996a). After destaining in several changes of acid-alcohol, the preparations were rehydrated. Following rinsing and clearing in a solution of 50% glycerol and 0.25% KOH, the cartilages were visualized under a stereo microscope.

C. Whole-Mount Zebrafish In Situ Hybridization

In situ hybridization was performed as previously described (Westerfield, 2000). Zebrafish foxD3 probes were synthesized as previously described (Stewart et al., 2006).

D. Target Profiling Assays for GPCR

GPCR profiling assays were performed by Millipore (St. Louis, MO) using in cells expressing G$\alpha$15, a promiscuous G protein that enhances GPCR coupling to downstream Ca2+ signaling pathways.

E. Zebrafish Injections

OGR1 morpholino 5'-TTTTTCCAACCA-CATGTTCAGAGTC-3' (SEQ ID NO:5) and Mismatch morpholino 5'-CCTCTTACCTCAGTTACAATTTATA-3 (SEQ ID NO:6) was synthesized by Genetools™. Morpholino and mRNA was injected as previously described (Westerfield, 2000).

F. RT-PCR

Melanoma cell lines were collected and RNA isolated with the RNeasy kit (Qiagen™ Valencia, CA). After subsequent cDNA amplification using Superscript III (Invitrogen™ Carlsbad, CA), samples were visualized in an agarose gel. Primer sequences are found in Table 1, below.

TABLE 1

GPR Primers.

| Gene | Forward Primer | Reverse Primer | SEQ ID NO |
|---|---|---|---|
| GPR4 | CCCTCCTGTCATAATTCCATCC | TGGTCTACAGGGAAGAGATGAG | 7, 8 |
| GPR65 | TGGCTGTTGTCTACCCTTTG | CCACAACATGACAGCATTGAAG | 9, 10 |
| GPR68 | GTTTGAAGGCGGCAGAAATG | GTGGAATGAGGAGGCATGA | 11, 12 |
| GPR132 | TTCAGGAGCATCAAGCAGAG | CGAAGCAGACTAGGAAGATGAC | 13, 14 |

TABLE 1-continued

GPR Primers.

| Gene | Forward Primer | Reverse Primer | SEQ ID NO |
|---|---|---|---|
| GAPDH | GTTTGAAGGCGGCAGAAATG | GTGGAATGAGGAGGCATGA | 15, 16 |

G. Cell Culture and Transfection

HCT116, U87, U138, HEK293, HEK293T, MeWo, A2058 and MCF7 cells were cultured in DMEM supplemented with 10% FBS (GIBCO™) and 1% penicillin-streptomycin (Cellgro™). WM115 cells were cultured in DMEM/F12 supplemented with 10% FBS (GIBCO™) and 1% penicillin-streptomycin (Cellgro™)

H. Luciferase Assay Transfection 12-well plates of cells were transfected with 1 µg DNA using Lipofectamine 3000 with sre:luciferase and either GFP, GPR68-GFP or 336X-GFP. After 3 days, these cells were then lysed, and cell extracts were subjected to Steady-Glo luciferase assay (Promega™) according to the manufacturer's instructions. The results were normalized to cell titer, as determined using Cell Titer-Glo luminescence assay (Promega™).

I. 336X-GFP Plasmid Generation

A deletion between amino acid 336 and the beginning of GFP was generated from the MCSV:GPR68-GFP plasmid using the Q5 mutagenesis kit (NEB).

J. Agarose Drop Assay

WM115 cells were trypsinized and resuspended at 100,000 cells per mL in low melt agarose. A 10 µl drop of the cell mixture was added to 12-well plate. After solidifying Normal culture media was added with either DMSO 0.5% or OGM 5 µM. The area around the agarose drop was visualized manually with light microscopy. The cells were incubated for 5 days and visualized. Cells outside of the agarose drop were visualized and quantitated.

K. Scratch Assay

Cells were grown to confluence and the cells were denuded with a P200 tip. A medium change was done to add fresh medium, remove loose cells and add compounds OGM (5 µM) and EIPA (10 µM). The area of the scratch was observed 20 hours later.

L. Chem-1 OGR1/GPR68 Recovery Assay

Chem-1 OGR1/GPR68 cells from Millipore™ (St. Louis, MO) were plated in 96-well format and stained with Fluo-8. Using the Lionheart FX (Biotek™) a baseline for 3 seconds was observed before the medium was acidified using an automated injector to reach pH 6.8. Cells then were dynamically monitored and change in fluorescence was quantified using Gen5 software (Biotek™). Pretreatment of 10 µM OGM2 for 4 hours was used. Each well was only assayed once at the correct time interval after inhibitor removal.

Example 2: Chemical Schemes and Structures

A. General Synthetic Scheme

Below is the general scheme for synthesis of compounds according to embodiments of the invention. The scheme refers to the following reagents and conditions: i) dry THF, 0° C.-room temperature; ii) chloroacetic acid, NaHCO$_3$·H$_2$O, 1 hour, room temperature; iii) 1N NaOH, NH$_2$NH$_2$·H$_2$O, 1 hour, room temperature; iv) EtOH, 40° C.

$R_1$ is —H, —CH$_3$, —Cl, —F, or —OCH$_3$; $R_2$ is —H, —C$_2$H$_5$, —Cl, —F, or —OCH$_3$.

B. Exemplary Procedure for the Synthesis of 5-fluoro-5'-(quinolin-6-yl)-1,2-dihydro-3'H-spiro[indole-3,2'-[1,3,4]thiadiazol]-2-one; OGM45

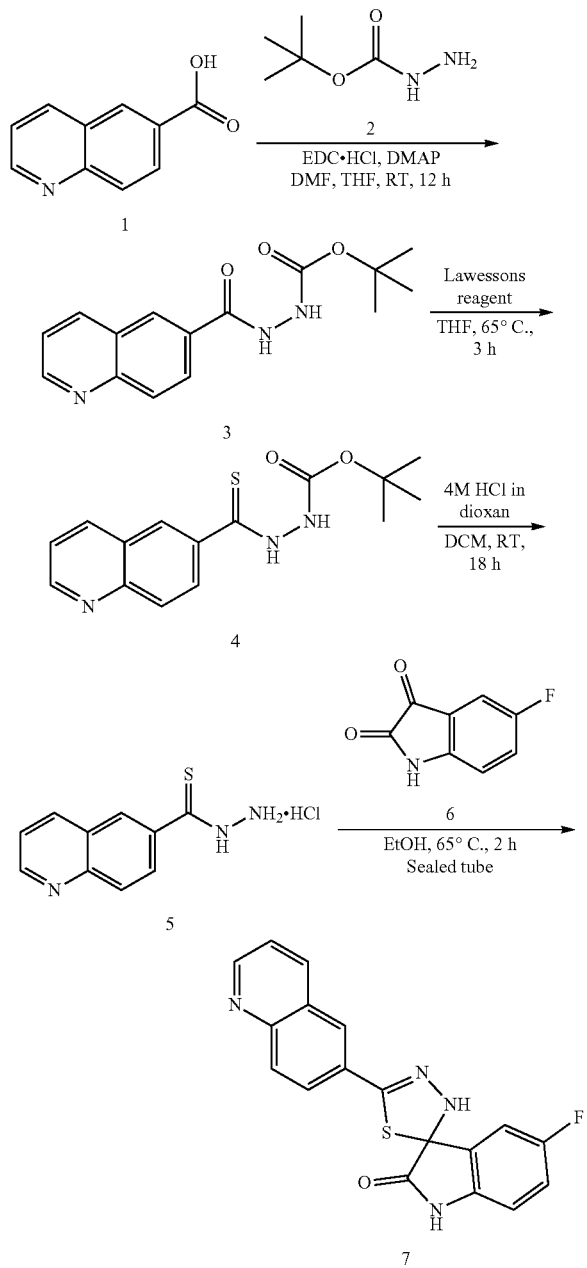

1. Synthesis of tert-butyl 2-(quinoline-4-carbonyl)hydrazine-1-carboxylate (3)

Procedure: To a stirred solution of quinoline-4-carboxylic acid (2.00 g, 11.5 mmol, 1.0 eq) in 30 mL of a mixture of DMF and THF (1:1) were added (tert-butoxy)carbohydrazide (1.68 g, 12.7 mmol, 1.1 eq), EDC·HCl (2.66 g, 13.9 mmol, 1.2 eq) and 4-(dimethylamino)pyridin-1-ium (0.021 g, 0.173 mmol, 0.015 eq). After 10 min, the mixture became homogeneous and stirring was continued for 3 h. Reaction was monitored by TLC. The reaction mixture was poured into ice and extracted with ethyl acetate (3×30 mL). The combined organic layer was washed with water (20 mL), brine (20 mL), dried over anhydrous sodium sulfate and concentrated under reduced pressure to give crude product. The crude product was purified by flash column chromatography over silica gel by using a combiflash purifier with 5% Methanol in DCM as eluent to give tert-butyl 2-(quinoline-4-carbonyl)hydrazine-1-carboxylate (1.8 g, 54%) as white solid. LCMS: m/z=288.2 [M+H]+.

2. Synthesis of Tert-butyl 2-(quinoline-6-carbonothioyl)hydrazine-1-carboxylate (4)

Procedure: To a stirred solution of N'-[(tert-butoxy)carbonyl]quinoline-6-carbohydrazide (1.3 g, 4.52 mmol, 1.0 eq) in THF (20 mL) was added Lawsson's Reagent (1.83 g, 4.52 mmol, 1.0 eq) at RT. The reaction mixture was heated to 65° C. and stirred for 3 h. Reaction was monitored by TLC and LCMS. The reaction mixture was cooled to RT and quenched with saturated sodium bicarbonate (20 mL) and extracted with ethyl acetate (2×10 mL). The combined organic layer was washed with water (10 mL), brine (10 mL), dried over anhydrous sodium sulphate and evaporated under reduced pressure to give crude product. The crude product was purified by flash column chromatography over silica gel by using a combiflash purifier with 6% MeOH in DCM as eluent to give tert-butyl 2-(quinoline-6-carbonothioyl)hydrazine-1-carboxylate (1.0 g, 73%) as yellow solid compound. LCMS: m/z=304.1 [M+H]+.

3. Synthesis of quinoline-6-carbothiohydrazide hydrochloride (5)

Procedure: To a stirred solution of tert-butyl 2-(quinoline-6-carbonothioyl)hydrazine-1-carboxylate (1.0 g, 3.30 mmol, 1.0 eq) in DCM (10 mL) was added 4M HCl in dioxane (10 mL) at 0° C. and stirred at room temperature for 18 h. Progress of the reaction was monitored by TLC (MeOH/DCM=5:95). After 12 hours the reaction was complete and the reaction mixture was concentrated to give residue. It was washed with diethyl ether (30 mL) and dried to give quinoline-6-carbothiohydrazide hydrochloride (0.7 g, 89%) as light yellow solid compound. LCMS: m/z=204.2 [M+H]+.

4. Synthesis of 5-fluoro-5'-(quinolin-6-yl)-1,2-dihydro-3'H-spiro[indole-3,2'-[1,3,4]thiadiazol]-2-one (7) (OGM45)

Procedure: To a sealed tube vial, N-aminoquinoline-6-carbothioamide hydrochloride (0.1 g, 0.41 mmol, 1.0 eq), 5-fluoro-2,3-dihydro-1H-indole-2,3-dione (0.069 g, 0.417 mmol, 1.0 eq) and ethanol (5 mL) were added and heated to 65° C. for 2 h. Reaction was monitored by TLC and LCMS. After completion of the starting material, reaction was cooled to RT and the solvent was concentrated to give the residue. It was diluted with EtOAc (10 mL) and washed with saturated bicarbonate (10 mL). Aqueous layer was extracted in to EtOAc (3×5 mL). Combined organics were washed with brine (10 mL), water (10 mL) and dried over Na$_2$SO$_4$, filtered and concentrated to give crude product. The crude product was purified by flash column chromatography by using combiflash purifier with 5-10% MeOH in DCM as eluent. Pure fractions were concentrated to give 5-fluoro-5'-(quinolin-6-yl)-1,2-dihydro-3'H-spiro[indole-3,2'-[1,3,4]

thiadiazol]-2-one as brown solid (0.018 g, 12%). LCMS (ES) m/z=351.0 [M+H]+; 1H NMR (400 MHz, DMSO d6) δ=10.70 (s, 1H), 9.11 (s, 1H), 8.91 (s, 1H), 8.45 (d, J=8.0 Hz, 1H), 8.10-8.02 (m, 2H), 7.95 (s, 1H), 7.58-7.55 (m, 1H), 7.41-7.39 (m, 1H), 7.16 (t, J=8.8 Hz, 1H), 6.88-6.86 (m, 1H), HPLC purity: 97.11% at 240 nm.

5. Exemplary Compounds

See Table 2, below for exemplary compounds synthesized using the general procedure outlined above for compound OGM45.

TABLE 2

Selected Exemplary Compounds.

| Compound Number | Compound Structure | Analytical Data |
|---|---|---|
| OGM37 | 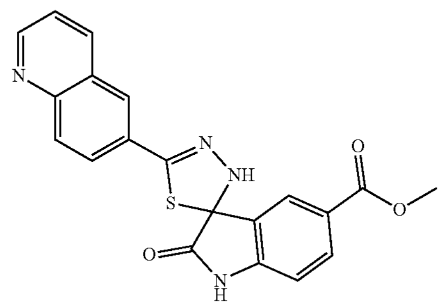 [SMILES: COC(=O)c1ccc2c(c1)C1(NN=C(c3ccc4ncccc4c3)S1)C(=O)N2] | LCMS (ES) m/z = 391.1 [M + H]+; 1H NMR (400 MHz, DMSO d6) δ = 11.00 (s, 1H), 9.11 (s, 1H), 8.91 (s, 1H), 8.46 (d, J = 8.4 Hz, 1H), 8.11-8.09 (m, 2H), 8.05-7.95 (m, 3H), 7.59-7.56 (m, 1H), 7.00 (d, J = 8.4 Hz, 1H), 3.79 (s, 3H); HPLC purity: 99.59% at 254 nm |
| OGM38 | 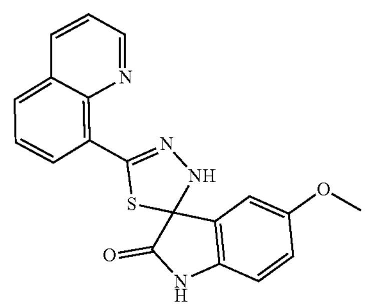 [SMILES: COc1ccc2c(c1)C1(NN=C(c3cccc4cccnc34)S1)C(=O)N2] | LCMS (ES) m/z = 363.2 [M + H]+; 1H NMR (400 MHz, DMSO d6) δ = 10.14 (s, 1H), 8.83-8.78 (m, 2H), 8.42 (d, J = 8.0 Hz, 1H), 8.37 (d, J = 7.6 Hz, 1H), 8.02 (d, J = 8.0 Hz, 1H), 7.67 (t, J = 8.0 Hz, 1H), 7.59-7.56 (m, 1H), 7.08 (s, 1H), 6.84 (d, J = 8.0 Hz, 1H), 6.75 (d, J = 8.4 Hz, 1H), 3.70 (s, 3H); HPLC purity: 97.87% at 254 nm. |
| OGM39 | 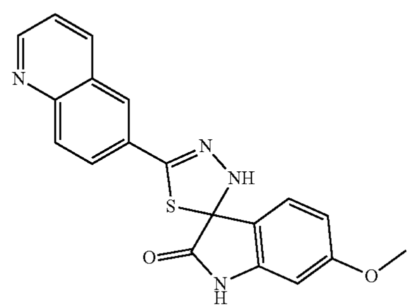 [SMILES: COc1ccc2c(c1)NC(=O)C21NN=C(c2ccc3ncccc3c2)S1] | LCMS (ES) m/z 363.1 [M + H]+; 1H NMR (400 MHz, DMSO d6) δ = 10.5 (s, 1H), 8.99 (s, 1H), 8.90 (s, 1H), 8.46-8.44 (m, 2H), 8.09-8.01 (m, 1H), 7.99 (m, 1H), 7.57-7.55 (m, 1H), 7.44-7.42 (m, 1H), 6.61-6.59 (s, 1H), 6.40 (m, 1H), 3.89 (s, 3H); HPLC purity: 98.7% at 254 nm. |
| OGM40 | 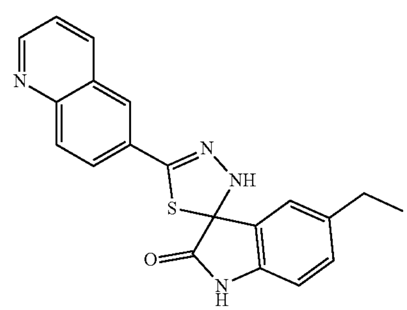 [SMILES: CCc1ccc2c(c1)C1(NN=C(c3ccc4ncccc4c3)S1)C(=O)N2] | LCMS (ES) m/z = 361.3 [M + H]+; 1H NMR (400 MHz, DMSO d6) δ = 10.42 (s, 1H), 9.09 (s, 1H), 8.94 (s, 1H), 8.53 (d, J = 7.6 Hz, 1H), 8.13-8.11 (m, 1H), 8.06 (m, 1H), 8.04-7.97 (m, 1H), 7.63-7.62 (m, 1H), 7.37 (s, 1H), 7.15-7.13 (m, 1H), 6.78-6.76 (m, 1H), 2.56-2.48 (m, 2H), 1.14-1.10 (m, 3H); HPLC purity: 99.56% at 254 nm. |

TABLE 2-continued

Selected Exemplary Compounds.

| Compound Number | Compound Structure | Analytical Data |
|---|---|---|
| OGM41 | 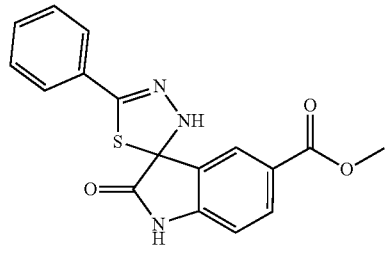 [SMILES: COC(=O)c1ccc2c(c1)C1(NN=C(c3ccccc3)S1)C(=O)N2] | LCMS (ES) m/z = 340.0 [M + H]+; 1H NMR (400 MHz, DMSO-d$_6$) 1H NMR (400 MHz, DMSO-d6) δ = 10.95 (s, 1H), 8.90 (s, 1H), 7.96-7.93 (m, 2H), 7.56-7.55 (m, 2H), 7.45-7.44 (m, 3H), 6.98-6.96 (d, J = 8.4 Hz, 1H), 3.79 (s, 3H). HPLC purity: 96.50% at 254 nm. |
| OGM42 | 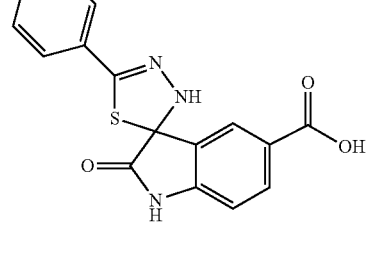 | LCMS (ES) m/z = 326.1 [M + H]+; 1H NMR (400 MHz, DMSO-d$_6$) δ 12.93 (s, 1H), 10.89 (s, 1H), 8.83 (s, 1H), 7.97-7.90 (m, 2H), 7.69 (d, J = 7.6 Hz, 1H), 7.55-7.44 (m, 3H), 7.22 (t, J = 7.2 Hz, 1H), 6.94 (d, J = 7.6 Hz, 1H). HPLC purity: 99.79% at 254 nm. |
| OGM43 | 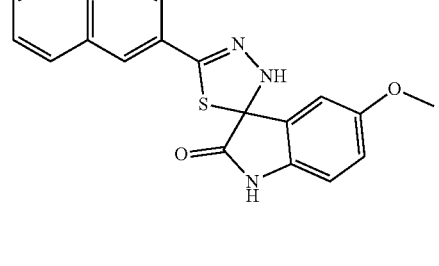 | LCMS (ES) m/z = 363.1 [M + H]+; 1H NMR (400 MHz, DMSO-d$_6$) δ 10.37 (s, 1H), 9.10-9.08 (m, 2H), 8.50 (d, J = 8.0 Hz, 1H), 8.11 (d, J = 7.2 Hz, 1H), 8.04 (d, J = 7.2 Hz, 1H), 7.96 (s, 1H), 7.59-7.52 (m, 1H), 7.11 (s, 1H), 6.88 (d, J = 8.4 Hz, 1H), 6.78 (d, J = 7.2 Hz, 1H), 3.70 (s, 3H). HPLC purity: 98.04% at 254 nm. |
| OGM44 | 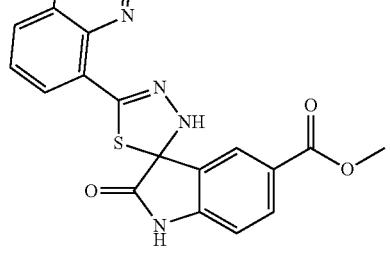 | LCMS (ES) m/z = 391.1 [M + H]+; 1H NMR (400 MHz, DMSO-d$_6$) δ 10.79 (s, 1H), 8.83 (s, 1H), 8.44 (d, J = 7.6 Hz, 1H), 8.38 (d, J = 7.6 Hz, 1H), 8.05-8.00 (m, 2H), 7.92 (d, J = 7.6 Hz, 1H), 7.69 (t, J = 8.0 Hz, 1H), 7.60-7.57 (m, 1H), 6.96 (d, J = 8.0 Hz, 1H), 3.79 (s, 3H). HPLC purity: 97.07% at 254 nm. |
| OGM46 | 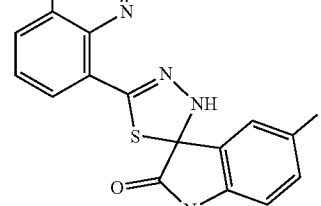 | LCMS (ES) m/z = 351.1 [M + H]+; 1H NMR (400 MHz, DMSO d6) δ = 10.36 (s, 1H), 8.83 (s, 2H), 8.43 (d, J = 8.4 Hz, 1H), 8.37 (d, J = 6.8 Hz, 1H), 8.03 (d, J = 8.0 Hz, 1H), 7.68 (t, J = 7.6 Hz, 1H), 7.59-7.58 (m, 1H), 7.34-7.33 (m, 1H), 7.08 (t, J = 8.0 Hz, 1H), 6.83-6.82 (m, 1H); HPLC purity: 98.44% at 254 nm. |

TABLE 2-continued

Selected Exemplary Compounds.

| Compound Number | Compound Structure | Analytical Data |
| --- | --- | --- |
| OGM47 | 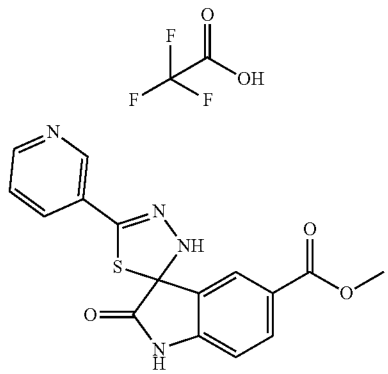 [SMILES: O=C(O)C(F)(F)F ; COC(=O)c1ccc2c(c1)C1(NN=C(c3cccnc3)S1)C(=O)N2] | LCMS (ES) m/z = 341.1 [M + H]+; 1H NMR (400 MHz, DMSO-d$_6$) δ 10.96 (s, 1H), 9.11 (s, 1H), 8.76 (s, 1H), 8.62-8.61 (m, 1H), 7.98-7.94 (m, 1H), 7.53 (t, J = 7.2 Hz, 3H), 6.98 (d, J = 7.6 Hz, 1H), 3.79 (s, 3H). HPLC purity: 99.05% at 254 nm. |
| OGM48 | 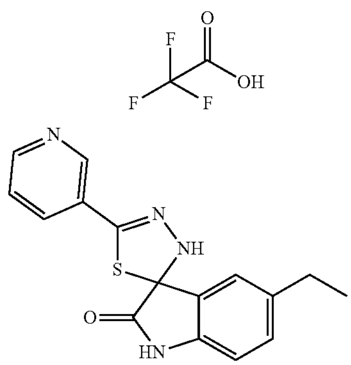 [SMILES: O=C(O)C(F)(F)F ; CCc1ccc2c(c1)C1(NN=C(c3cccnc3)S1)C(=O)N2] | LCMS (ES) m/z 311.1 [M + H]+; 1H NMR (400 MHz, DMSO-d$_6$) δ 10.43 (s, 1H), 9.11 (bs, 1H), 8.74 (s, 1H), 8.60 (d, J = 4.0 Hz, 1H), 7.94 (d, J = 7.6 Hz, 1H), 7.51 (t, J = 5.2 Hz, 1H), 7.35 (s, 1H), 7.13 (s, 1H), 7.13 (d, J = 8.0 Hz, 1H), 6.76 (d, J = 8.0 Hz, 1H), 2.58-2.52 (m, 2H), 1.12 (t, J = 7.2 Hz, 3H). HPLC purity: 99.46% at 254 nm. |
| OGM50 | 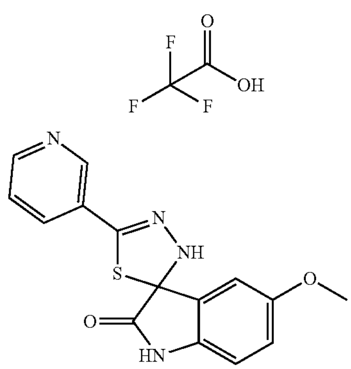 [SMILES: O=C(O)C(F)(F)F ; COc1ccc2c(c1)C1(NN=C(c3cccnc3)S1)C(=O)N2] | LCMS (ES) m/z = 313.1 [M + H]+; 1H NMR (400 MHz, DMSO-d$_6$) δ 10.35 (s, 1H), 9.10 (s, 1H), 8.75 (s, 1H), 8.61 (d, J = 8.0 Hz, 1H), 7.97 (d, J = 7.2 Hz, 1H), 7.54 (t, J = 5.2 Hz, 1H), 7.08 (s, 1H), 6.88 (d, J = 8.4 Hz, 1H), 6.77 (d, J = 8.4 Hz, 1H), 3.69 (s, 3H). HPLC purity: 98.43% at 254 nm. |
| OGM52 | 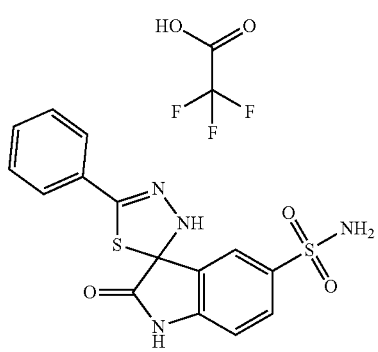 [SMILES: NS(=O)(=O)c1ccc2c(c1)C1(NN=C(c3ccccc3)S1)C(=O)N2 ; O=C(O)C(F)(F)F] | LCMS (ES) m/z = 361.0 [M + H]+; 1H NMR (400 MHz, DMSO d6) δ = 10.89 (s, 1H), 8.94 (s, 1H), 7.90 (s, 1H), 7.74 (d, J = 8.0 Hz, 1H), 7.56-7.54 (m, 2H), 7.45-7.43 (m, 3H), 7.28 (s, 2H), 6.98 (d, J = 8.4 Hz, 1H); HPLC purity: 99.29% at 254 nm. |

TABLE 2-continued

Selected Exemplary Compounds.

| Compound Number | Compound Structure | Analytical Data |
|---|---|---|
| OGM53 | (pyridin-3-yl-thiadiazole spiro-oxindole with sulfonamide; TFA salt) | LCMS (ES) m/z = 360.1 [M − H]+; 1H NMR (400 MHz, DMSO d6) δ = 10.93 (s, 1H), 9.16 (bs, 1H), 8.76 (s, 1H), 8.61-8.60 (m, 1H), 7.96 (d, J = 8.0 Hz, 1H), 7.91 (s, 1H), 7.76 (d, J = 8.0 Hz, 1H);, 7.53-7.50 (m, 1H), 7.18 (s, 2H), 6.99 (d, J = 8.4 Hz, 1H); HPLC purity: 99.67% at 254 nm. |
| OGM54 | (quinolin-6-yl-thiadiazole spiro-oxindole with carboxylic acid; TFA salt) | LCMS (ES) m/z = 377.1 [M + H]+; 1H NMR (400 MHz, DMSO d6) δ = 12.8 (bs, 1H), 10.95 (s, 1H), 9.10 (s, 1H), 8.92 (s, 1H), 8.48 (d, J = 7.6 Hz, 1H), 8.11 (d, J = 8.8 Hz, 1H), 8.04 (d, J = 8.8 Hz, 1H), 7.98 (s, 2H), 7.92 (d, J = 8.4 Hz, 1H), 7.60-7.57 (m, 1H), 6.96 (d, J = 8.4 Hz, 1H); HPLC purity: 99.1% at 254 nm. |
| OGM55 | (quinolin-6-yl-thiadiazole spiro-oxindole with sulfonamide; TFA salt) | LCMS (ES) m/z = 412.1 [M + H]+; 1H NMR (400 MHz, DMSO d6) δ = 10.95 (s, 1H), 9.18 (s, 1H), 8.95 (s, 1H), 8.54 (d, J = 7.6 Hz, 1H), 8.14 (d, J = 8.4 Hz, 2H), 8.08-8.01 (m, 1H), 7.94 (s, 1H), 7.76 (d, J = 8.0 Hz, 1H), 7.63 (s, 1H), 7.29 (s, 2H), 7.01 (d, J = 8.4 Hz, 1H); HPLC purity: 95.10% at 224 nm. |
| OGM56 | (pyridin-3-yl-thiadiazole spiro-5-fluoro-oxindole) | LCMS (ES) m/z = 301.0 [M + H]+; 1H NMR (400 MHz, DMSO d6) δ = 10.55 (s, 1H), 9.08 (s, 1H), 8.72 (s, 1H), 8.57 (s, 1H), 7.90 (d, J = 7.6 Hz, 1H), 7.48-7.45 (m, 1H), 7.37-7.36 (m, 1H); , 7.16-7.12 (m, 1H), 6.86-6.84 (m, 1H); HPLC purity: 98.88% at 220 nm. |

TABLE 2-continued

Selected Exemplary Compounds.

| Compound Number | Compound Structure | Analytical Data |
|---|---|---|
| OGM58 | 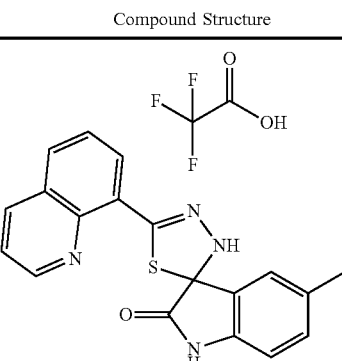 | LCMS (ES) m/z = 361.2 [M + H]+; 1H NMR (400 MHz, DMSO d6) δ = 10.36 (s, 1H), 8.83 (s, 2H), 8.43 (d, J = 8.4 Hz, 1H), 8.37 (d, J = 6.8 Hz, 1H), 8.03 (d, J = 8.0 Hz, 1H), 7.68 (m, 1H), 7.59-7.58 (m, 1H), 7.34-7.33 (m, 1H), 7.08 (s, 1H), 6.74-6.72 (m, 1H), 2.58-2.56 (m, 2H), 1.15-1.11 (m, 3H); ; HPLC purity: 98.5% at 254 nm. |
| OGM61 | 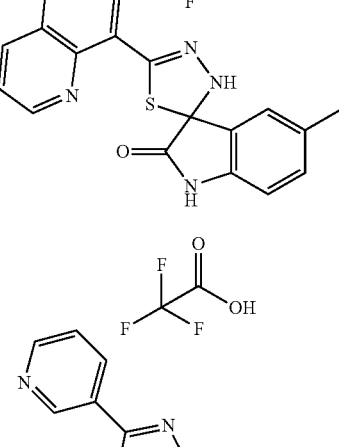 | LCMS (ES) m/z = 327.1 [M + H]+; 1H NMR (400 MHz, DMSO-$d_6$) δ 12.9 (s, 1H), 10.92 (s, 1H), 9.10 (s, 1H), 8.75 (s, 1H), 8.61 (s, 1H), 7.98-7.91 (s, 3H), 7.54-7.52 (m, 1H), 6.95 (d, J = 8.0 Hz, 1H). HPLC purity: 99.12% at 254 nm. |

C Synthesis of methyl 2,3-dioxoindoline-5-carboxylate

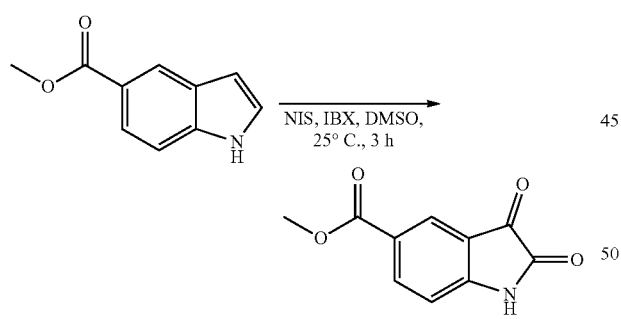

Procedure: To a stirred solution of methyl 1H-indole-5-carboxylate (3.00 g, 17.1 mmol) in 50.0 mL of DMSO were added 1-iodopyrrolidine-2,5-dione (4.62 g, 1.2 eq., 20.5 mmol) and 1-hydroxy-1-oxo-3H-1λ$^5$,2-benziodoxol-3-one (14.4 g, 3 eq., 51.4 mmol) at 25 25° C. The reaction mixture was stirred for 3 h at same temperature. Reaction was monitored by TLC. The reaction mixture was poured into ice and extracted with ethyl acetate (3×30 mL). The reaction was monitored by TLC. After completion of reaction, the reaction mixture was diluted with water (50 mL) and extracted with ethyl acetate (3×50 mL). The combined organic layer was washed with saturated $Na_2S_2O_3$ (30 mL), water (20 mL), brine (20 mL), dried over anhydrous sodium sulfate and concentrated under reduced pressure to give crude product. The crude product was purified by flash column chromatography over silica gel by using combiflash purifier with 70% ethyl acetate in heptane as eluent to give methyl 2,3-dioxoindoline-5-carboxylate as brown solid. (Yield: 2.2 g, 62%). m/z=204.0 [M+H]+.

D. Synthesis of 5-ethyl-5'-(2-methoxypyridin-4-yl)-1,2-dihydro-3'H-spiro[indole-3,2'-[1,3,4]thiadiazol]-2-one: 2,2,2-trifluoroacetic Acid (OGM49)

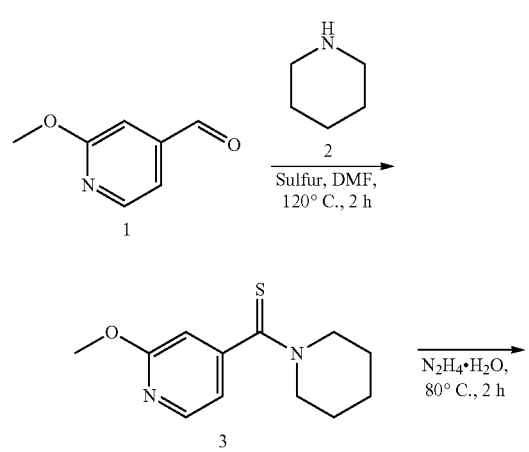

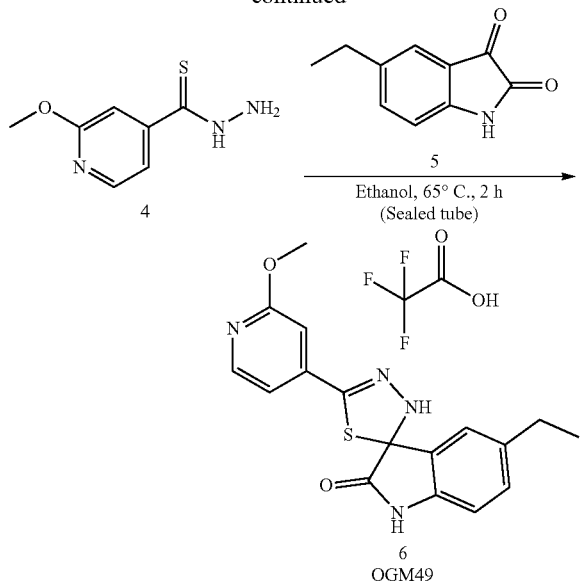

E. Synthesis of (2-methoxypyridin-4-yl) (piperidin-1-yl)methanethione

Procedure: To a stirred solution of 2-methoxypyridine-4-carbaldehyde (2.0 g, 14.6 mmol) in 10.0 mL of DMF were added piperidine (1.24 g, 14.6 mmol) and sulfur (1.87 g, 4 eq., 58.3 mmol) at room temperature. The reaction mixture was stirred for 3 h at 120° C. Reaction was monitored by TLC. The reaction mixture was poured into ice water (50 mL) and the precipitate was filtered and the solid washed with heptane and dried under vacuum to give crude (2-methoxypyridin-4-yl) (piperidin-1-yl)methanethione as yellow solid. (Yield: 3.0 g, 87%). m/z=237.2 [M+H]+.

F. Synthesis of N-amino-2-methoxypyridine-4-carbothioamide

A mixture of 2-methoxy-4-(piperidine-1-carbothioyl) pyridine (2.2 g, 9.31 mmol) and hydrazine monohydrate (10 mL) was stirred for 2 h at 80° C. The reaction was monitored by TLC and LCMS, the reaction mixture was diluted with water (30 mL) and the solution carefully adjusted to pH-6 with acetic acid. The desired product was extracted with ethyl acetate (3×50 mL), washed with water (30 mL), brine (30 mL) and the combined organic layer was dried over sodium sulphate and evaporated under reduced pressure to give crude N-amino-2-methoxypyridine-4-carbothioamide as a brown solid. (Yield: 1.0 g, crude). m/z=184.1 [M+H]+.

G. Synthesis of 5-ethyl-5'-(2-methoxypyridin-4-yl)-1,2-dihydro-3'H-spiro[indole-3,2'-[1,3,4]thiadiazol]-2-one: 2,2,2-trifluoroacetic Acid (OGM49, UMMC01-JBL-55680-P-01)

Procedure: To a stirred solution of N-amino-2-methoxy-pyridine-4-carbothioamide (0.2 g, 1.09 mmol) in ethanol (5.00 mL), was added 5-ethyl-2,3-dihydro-1H-indole-2,3-dione (0.191 g, 1.09 mmol) at room temperature. The reaction mixture was stirred for 2 h at 65° C. Reaction was monitored by TLC. The reaction mixture was poured into ice and extracted with ethyl acetate (3×30 mL). The reaction was monitored by TLC. After completion of reaction, the reaction mixture was diluted with water (50 mL) and extracted with ethyl acetate (3×50 mL). The combined organic layer was washed with water (20 mL), brine (20 mL), dried over anhydrous sodium sulfate and concentrated under reduced pressure to give crude product. The crude product was purified by flash column chromatography by using combiflash purifier with 70% ethyl acetate in heptane as eluent. Further purification was on by Preparative HPLC using 0.1% TFA in water and acetonitrile. Column: X-BridgeC-18 (250 mm×4.6 mm×5 mic) to give 5-ethyl-5'-(2-methoxypyridin-4-yl)-1,2-dihydro-3'H-spiro[indole-3,2'-[1,3,4]thiadiazol]-2-one: 2,2,2-trifluoroacetic acid as yellow solid. 1H NMR (400 MHz, DMSO-d6) δ 1H NMR (400 MHz, DMSO-d6) δ=10.43 (s, 1H), 9.21 (s, 1H), 8.17 (d, J=5.6 Hz, 1H), 7.31 (s, 1H), 7.13 (d, J=6 Hz, 2H), 6.77-6.72 (m, 2H), 3.85 (s, 3H), 2.56-2.48 (m, 2H), 1.10 (t, J=7.2 Hz, 3H). HPLC purity: 99.29% at 254 nm. m/z=341.2 [M+H]+ (yield: 0.11 g. 29%).

H. Exemplary Compounds

See Table 3, below for exemplary compounds synthesized using the general procedure outlined above for compound OGM49.

TABLE 3

Selected Exemplary Compounds.

| Compound Number | Compound Structure | Analytical Data |
|---|---|---|
| OGM51 | (structure shown) | LCMS (ES) m/z = 343.2 [M + H]+; 1H NMR (400 MHz, DMSO-d6) 1H NMR (400 MHz, DMSO-d6) δ = 10.34 (s, 1H), 9.25 (s, 1H), 8.18 (d, J = 4.4 Hz, 1H), 7.13-7.07 (m, 2H), 6.88-6.86 (m, 1H), 6.77-6.73 (m, 2H), 3.85 (s, 3H), 3.69 (s, 3H). HPLC purity: 98.47% at 254 nm. |

TABLE 3-continued

Selected Exemplary Compounds.

| Compound Number | Compound Structure | Analytical Data |
|---|---|---|
| OGM57 | (structure) | LCMS (ES) m/z = 331.2 [M + H]+; 1H NMR (400 MHz, DMSO d6) δ = 10.56 (s, 1H), 9.26 (s, 1H), 8.19-8.18 (m, 1H), 7.36 (d, J = 7.6 Hz, 1H), 7.16-7.12 (m, 2H), 6.80-6.70 (m, 1H), 6.37 (s, 1H), 3.86 (s, 3H); HPLC purity: 97.15% at 220 nm. |
| OGM59 | (structure) | LCMS (ES) m/z 313.1 [M + H]+; 1H NMR (400 MHz, DMSO d6) δ = 10.54 (s, 1H), 9.58 (s, 1H), 8.67 (d, J = 4.8 Hz, 2H), 7.63 (s, 2H), 7.41-7.38 (m, 1H), 6.60-6.58 (m, 1H), 6.39 (m, 1H), 3.85 (s, 3H); HPLC purity: 99.07% at 254 nm. |
| OGM60 | (structure) | LCMS (ES) m/z 311.2 [M + H]+; 1H NMR (400 MHz, DMSO d6) δ = 10.48 (s, 1H), 9.61 (s, 1H), 8.67 (d, J = 4.8 Hz, 2H), 7.62 (d, J = 5.2 Hz, 2H), 7.34 (s, 1H), 7.15 (d, J =7.2 Hz, 1H), 6.76 (m, 1H), 2.57-2.54 (m, 2H), 1.14-1.10 (m, 3H); HPLC purity: 95.5% at 254 nm. |
| OGM62 | (structure) | LCMS (ES) m/z = 371.1 [M + H]+; 1H NMR (400 MHz, DMSO-d6) δ 10.97 (s, 1H), 9.26 (s, 1H), 8.2 (d, J = 5.6 Hz, 1H), 7.94 (d, J = 8.0 Hz, 2H), 7.15 (d, J = 4.8 Hz, 1H), 6.97 (t, J = 8.4 Hz, 1H), 6.75 (s, 1H), 3.86 (s, 3H), 3.75 (s, 3H). HPLC purity: 99.15% at 254 nm. |

TABLE 3-continued

Selected Exemplary Compounds.

| Compound Number | Compound Structure | Analytical Data |
|---|---|---|
| OGM63 | 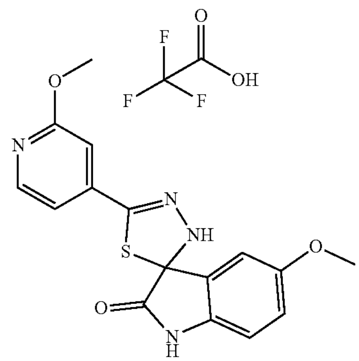 | LCMS (ES) m/z = 343.0 [M + H]+; 1H NMR (400 MHz, DMSO-d₆) δ 10.34 (s, 1H), 9.24 (s, 1H), 8.18 (d, J = 5.2 Hz, 1H), 7.13 (d, J = 5.2 Hz, 1H), 7.06 (s, 1H), 6.89-6.86 (m, 1H), 6.77-6.73 (m, 2H), 3.85 (s, 3H), 3.69 (s, 3H). HPLC purity: 99.19% at 254 nm. |
| OGM64 | 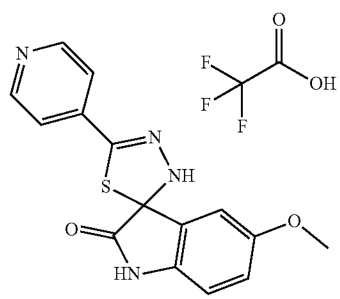 [SMILES: COc1ccc2c(c1)C1(NN=C(c3ccncc3)S1)C(=O)N2 ; O=C(O)C(F)(F)F] | LCMS (ES) m/z 313.1 [M + H]+; 1H NMR (400 MHz, DMSO d6) δ = 10.4 (s, 1H), 9.64 (s, 1H), 8.67 (d, J = 5.2, 2H), 7.63 (d, J = 5.2 Hz, 2H), 7.08 (s, 1H), 6.90-6.88 (m, 1H), 6.79-6.77 (m, 1H), 3.75-3.69 (s, 3H); HPLC purity: 98.07% at 254 nm. |
| OGM65 | 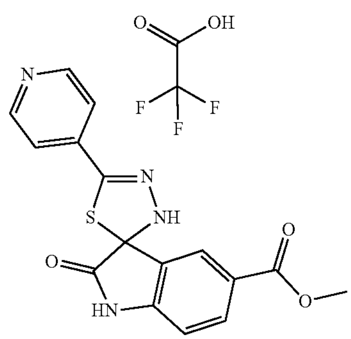 | LCMS (ES) m/z 341.0 [M + H]+; 1H NMR (400 MHz, DMSO d6) δ = 11.01 (s, 1H), 9.59 (s, 1H), 8.64 (d, J = 5.2 Hz, 2H), 7.96-7.94 (m, 2H), 7.62 (d, J = 5.2 Hz, 2H), 7.00-6.98 (m, 1H), 3.66 (s, 3H); HPLC purity: 99.87% at 254 nm. |
| OGM66 | 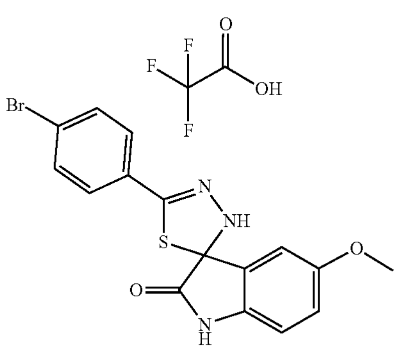 | LCMS (ES) m/z = 390.0 [M + H]+; 1H NMR (400 MHz, DMSO-d₆) δ 10.30 (s, 1H), 8.94 (s, 1H), 8.62 (d, J = 8.4 Hz, 2H), 7.46 (d, J = 8.4 Hz, 2H), 7.06 (s, 1H), 6.87-6.85 (m, 1H), 6.75 (s, 1H), 3.69 (s, 3H). HPLC purity: 99.95% at 254 nm. |

TABLE 3-continued

| Compound Number | Compound Structure | Analytical Data |
|---|---|---|
| OGM67 | 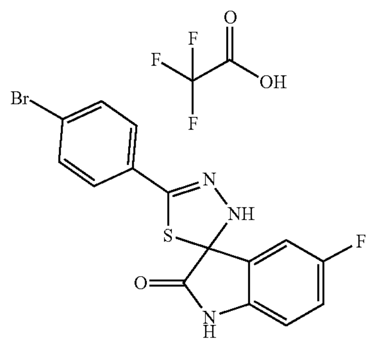 | LCMS (ES) m/z = 378.0 [M + H]+; 1H NMR (400 MHz, DMSO-d$_6$) δ 10.54 (s, 1H), 8.98 (s, 1H), 7.63 (d, J = 8.0 Hz, 2H), 7.46 (d, J = 8.4 Hz, 2H), 7.35 (d, J = 6.8 Hz, 1H), 7.13 (t, J = 7.6 Hz, 1H), 6.85-6.84 (m, 1H). HPLC purity: 99.89% at 254 nm. |
| OGM68 | 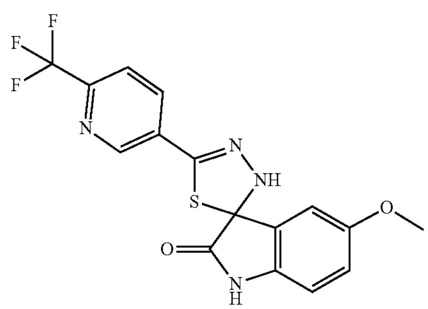 | LCMS (ES) m/z 351.0 [M + H]+; 1H NMR (400 MHz, DMSO d6) δ = 10.40 (s, 1H), 9.38 (s, 1H), 8.92 (s, 1H), 8.10 (d, J = 8.0 Hz, 1H), 7.94 (d, J = 8.0 Hz, 1H), 7.09 (s, 1H), 6.88 (d, J = 8.4 Hz, 1H), 6.77 (d, J = 8.4 Hz, 1H), 3.69 (s, 3H), HPLC purity: 99.66% at 254 nm |
| OGM69 | 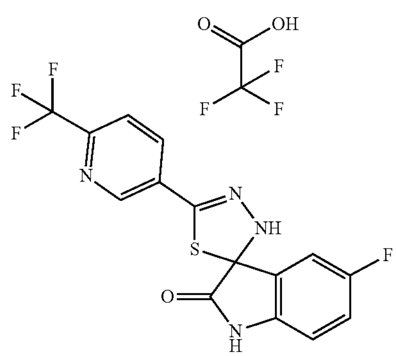 | LCMS (ES) m/z 369.2 [M + H]+; 1H NMR (400 MHz, DMSO d6) δ = 10.62 (s, 1H), 9.39 (s, 1H), 8.92 (s, 1H), 8.11 (d, J = 7.6 Hz, 1H), 7.95 (d, J = 8.0 Hz, 1H), 7.39 (d, J = 7.2 Hz, 1H), 7.15 (t, J = 8.0 Hz, 1H), 6.87-6.84 (m, 1H), HPLC purity: 98.48% at 220 nm |
| OGM70 | 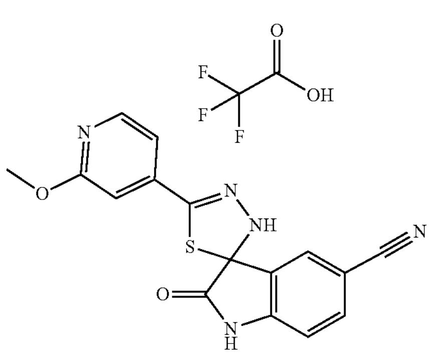 | LCMS (ES) m/z 338.3 [M + H]+; 1H NMR (400 MHz, DMSO d6) δ = 11.03 (s, 1H), 9.22 (s, 1H), 8.19 (d, J = 5.2 Hz, 1H), 7.95 (s, , 1H), 7.77 (d, J = 8.4 Hz, 1H), 7.14 (d, J = 4.8 Hz, 1H), 7.00 (d, J = 8.4 Hz, 1H), 6.75 (s, 1H), 3.86 (s, 3H); HPLC purity: 99.93% at 254 nm. |

TABLE 3-continued

Selected Exemplary Compounds.

| Compound Number | Compound Structure | Analytical Data |
|---|---|---|
| OGM71 | (structure) | LCMS (ES) m/z 379.1 [M + H]+; 1H NMR (400 MHz, DMSO d6) δ = 10.49 (s, 1H), 9.35 (s, 1H), 8.91 (s, 1H), 8.09 (d, J = 8 Hz, 1H), 7.94 (d, J = 8.4 Hz, 1H), 7.36 (s, 1H), 7.14 (d, J = 8 Hz, 1H), 6.76 (d, J = 7.6 Hz, 1H), 2.64-2.55 (m, 2H), 1.13-1.09 (m, 3H); HPLC purity: 99.61% at 254 nm. |
| OGM72 | (structure) | LCMS (ES) m/z 381.1 [M + H]+; 1H NMR (400 MHz, DMSO d6) δ = 10.53 (s, 1H), 9.29 (s, 1H), 8.90 (s, 1H), 8.08 (d, J = 7.6 Hz, 1H), 7.93 (d, J = 8.0 Hz, 1H), 7.41 (d, J = 8 Hz, 1H), 6.58 (d, J = 7.6 Hz, 1H), 6.38 (s, 1H) 3.78-3.74 (s, 3H); HPLC purity: 98.96% at 254 nm. |

Example 3: UKbiobank has Both Synonymous Variants and a Rare Stopgain in GPR68

Of 500 k individuals carriers of these variants were determined. The stop gain variant is predicted as impactful in multiple functional prediction algorithms. The stopgain variant (rs61745752, E336X) is associated with increased odds of malignant melanoma on the face, prostate cancer, secondary malignancy in the rectum and other benign neoplasms. See data in FIG. 9.

Example 4: Initial Screenings to Discover the Active Compound Ogremorphin

Figure 1B:
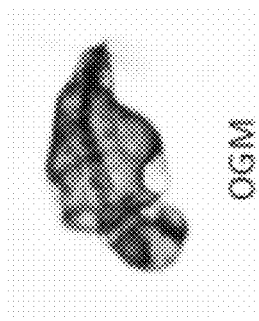
Figure 1C:
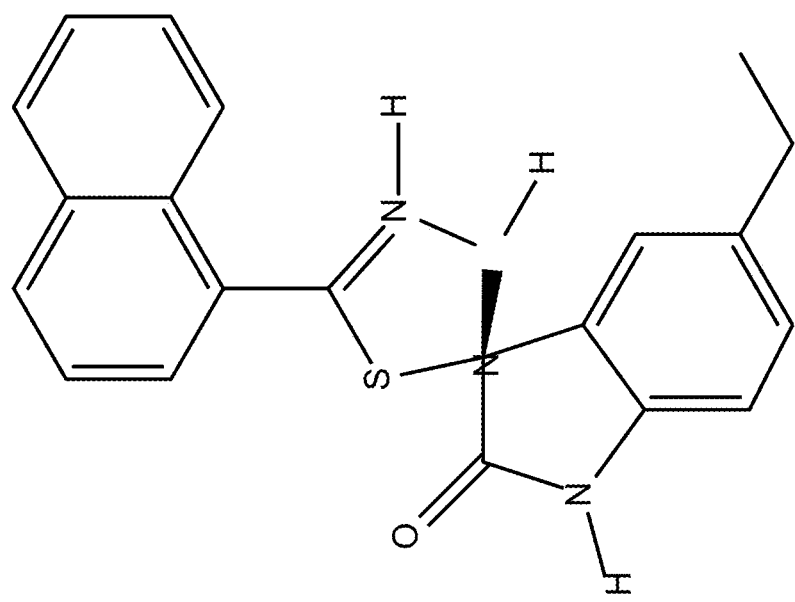

To discover novel small molecule modulators of embryonic development an unbiased screen of ~30,000 small molecules was conducted, in which the compounds were assayed for their ability to induce phenotypic changes in the morphology of zebrafish. Further information on these assays can be found in Hao et al., 2013 and Williams et al., 2015. The compound 5-ethyl-5'-naphthalen-1-ylspiro[1H-indole-3,2'-3H-1,3,4-thiadiazole]-2-one (herein referred to as Ogremorphin (OGM) (see FIG. 1A) was identified. This compound was identified based on the phenotype of aberrant pigmentation. Compare FIG. 1B and FIG. 1C, which show a dorsal view of a representative DMSO vehicle control-treated zebrafish embryo at 48 hours pf and a dorsal view of a representative OGM (10 uM)-treated zebrafish embryo at 48 hours pf. In addition to pigmentation defects, Ogremorphin reproducibly induced ventral curvature, wavy notochord, shortened body axis, craniofacial defects, and loss of retinal iridophores.

Figure 1D:
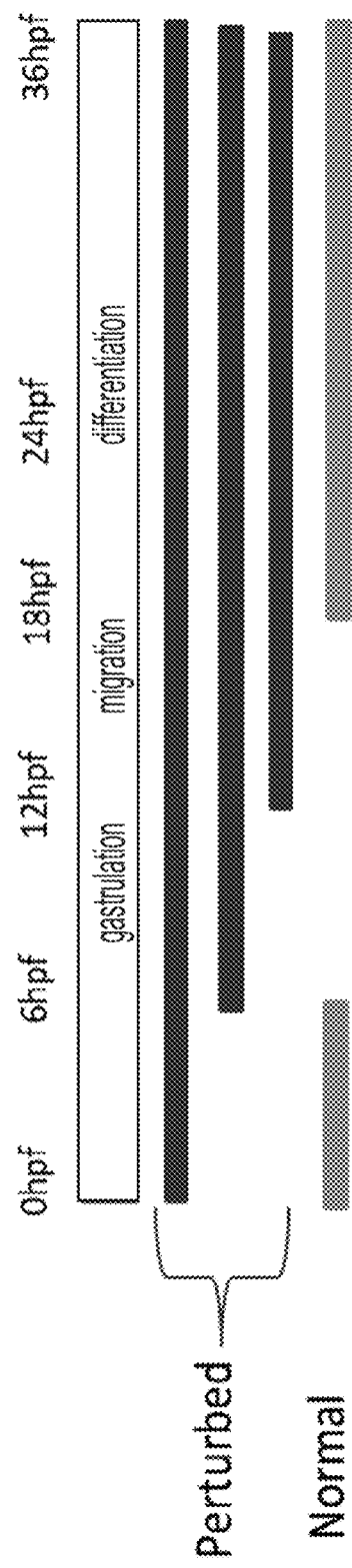

The loss of melanophores, iridophores and craniofacial cartilage are consistent with abrogation of neural crest development. Temporal phenotypic analysis was conducted. The results are shown in FIG. 1D. Pigmentation defect was dependent on treatment during the 12 hours pf-18 hours pf time window. Embryos treated throughout development (0-36 hours pf) had perturbed pigmentation. Embryos treated 6-36 hours pf and treated 12-36 hours pf also had perturbed pigmentation. Embryos treated 18-36 hours pf, however, had normal pigmentation, as well as embryos treated with a short pulse 0-6 hours pf. Thus, the time course analysis showed that pigmentation was subject to perturbation by OGM during a specific window of time correlated to neural crest migration (FIG. 1D).

Figure 1E:
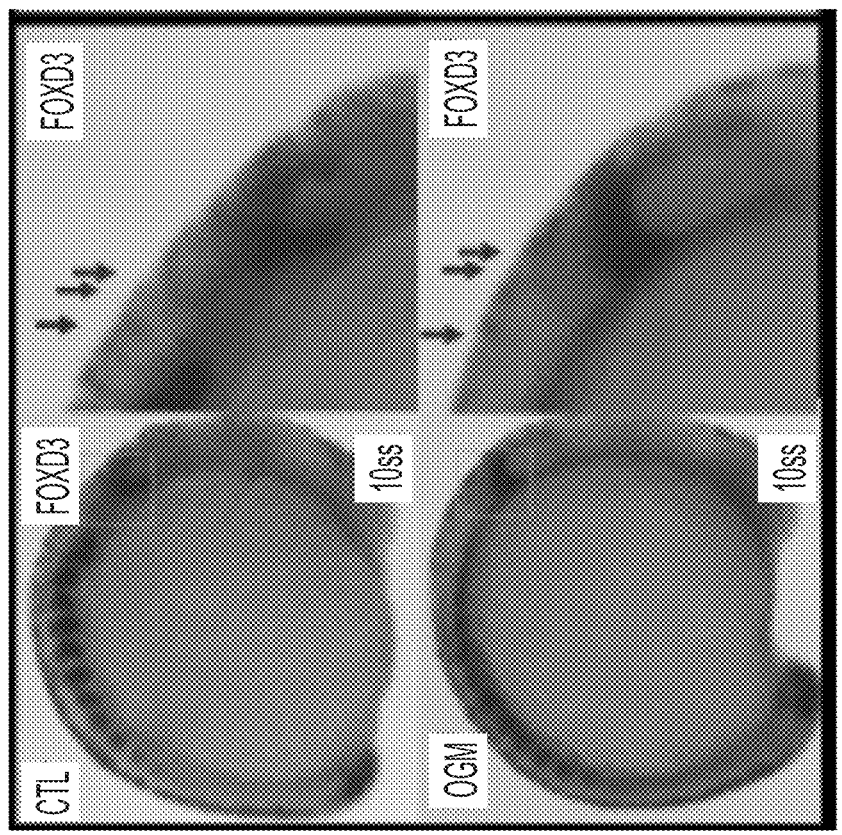

To identify if neural crest progenitors were perturbed by OGM, foxD3 staining was performed. This identified no difference. See FIG. 1E, which shows a lateral view of control and OGM-treated zebrafish after in situ hybridization of FOXD3. The views on the right show a magnification of the indicated area, with arrows showing positive staining along the dorsal ridge of the embryo. This suggests that the target of OGM plays a role affecting pigment cells after the formation of neural crest progenitors.

Example 5: Medicinal Chemistry

The compounds in Table 4, below, were tested for inhibition of GPR68/OGR1 using CHEM1-OGR1 cells. Briefly, the methods were: On the day before the assay 20,000 cells per well of CHEM1-OGR1 cells were plated in 10% DMEM containing 10% FBS and 1% Pen/Strep into a 96 well plate. After 24 hours media was removed and cells were stained with 80 uL Fluo-8 calcium indicator dye according to manufacturer's protocol. After staining cells were treated with 20 uL of 4× concentration of test compounds. Using kinetic imaging in the Lionheart HCS fluorescence intensity was continuously measure at 10 frames per second, for 5 seconds before 100 µL of acidified media was added to the well resulting in a pH of 6.4. A ratio of fluorescence intensities prior to addition and at peak were calculated and averaged. The resulting data were platted and using a 4 parameter logistic regression EC50 for each test compound was determined. The EC50 of each compound is provided in the table.

TABLE 4

Medicinal Chemistry Data.

| Compound Number | Compound Structure | EC50 (μM) |
| --- | --- | --- |
| OGM2 | 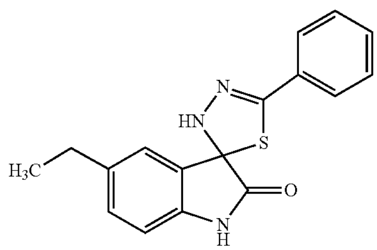 [SMILES: CCc1ccc2c(c1)C1(NN=C(c3ccccc3)S1)C(=O)N2] | 1.347 |
| OGM1 | 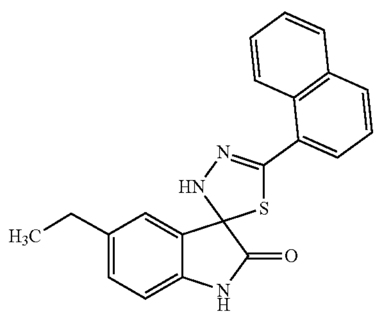 [SMILES: CCc1ccc2c(c1)C1(NN=C(c3cccc4ccccc34)S1)C(=O)N2] | 0.17 |
| OGM7 | 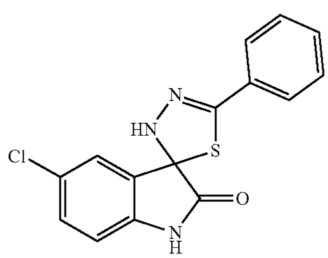 [SMILES: O=C1Nc2ccc(Cl)cc2C12NN=C(c1ccccc1)S2] | 1.62 |
| OGM8 | 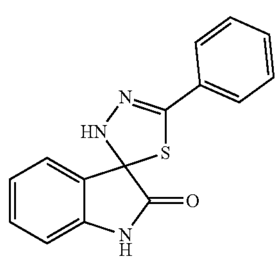 [SMILES: O=C1Nc2ccccc2C12NN=C(c1ccccc1)S2] | 2.744 |
| OGM9 | 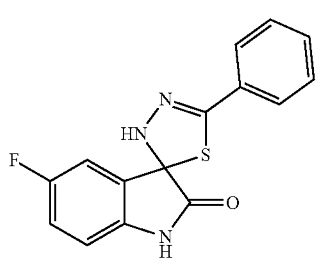 [SMILES: O=C1Nc2ccc(F)cc2C12NN=C(c1ccccc1)S2] | 2.839 |

TABLE 4-continued

Medicinal Chemistry Data.

| Compound Number | Compound Structure | EC50 (μM) |
| --- | --- | --- |
| OGM10 | 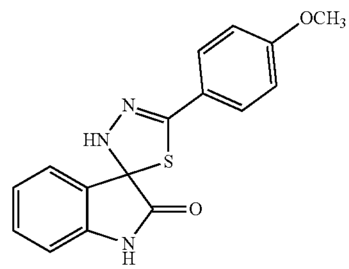 [SMILES: COc1ccc(C2=NNC3(S2)C(=O)Nc2ccccc23)cc1] | 1.44 |
| OGM12 | 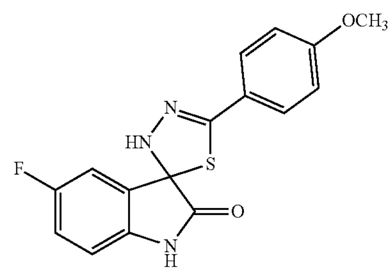 [SMILES: COc1ccc(C2=NNC3(S2)C(=O)Nc2ccc(F)cc23)cc1] | 0.756 |
| OGM13 | 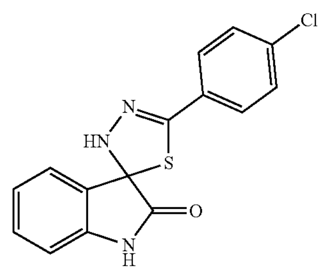 [SMILES: O=C1Nc2ccccc2C12NN=C(c1ccc(Cl)cc1)S2] | <0.4 |
| OGM14 | 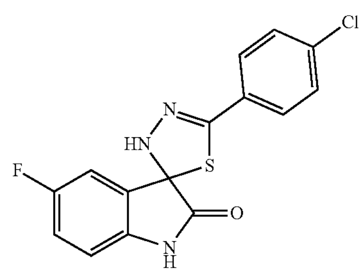 [SMILES: O=C1Nc2ccc(F)cc2C12NN=C(c1ccc(Cl)cc1)S2] | 1.831 |
| OGM15 | 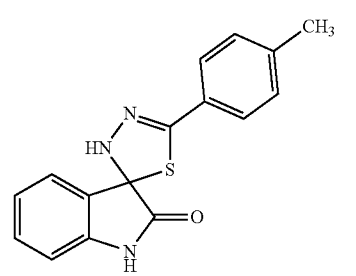 [SMILES: Cc1ccc(C2=NNC3(S2)C(=O)Nc2ccccc23)cc1] | 1.06 |

TABLE 4-continued

Medicinal Chemistry Data.

| Compound Number | Compound Structure | EC50 (μM) |
|---|---|---|
| OGM16 | 5-Cl-indolin-2-one spiro-thiadiazoline with 4-methylphenyl | 0.785 |
| OGM17 | 5-methoxy-indolin-2-one spiro-thiadiazoline with 4-methoxyphenyl | 0.9 |
| OGM18 | 5-F-indolin-2-one spiro-thiadiazoline with 4-methylphenyl | 0.985 |
| OGM19 | 5-Cl-indolin-2-one spiro-thiadiazoline with 4-chlorophenyl | <0.4 |
| OGM20 | indolin-2-one spiro-thiadiazoline with 4-fluorophenyl | 3.997 |
| OGM21 | 5-Cl-indolin-2-one spiro-thiadiazoline with 4-fluorophenyl | 0.796 |
| OGM22 | 5-methoxy-indolin-2-one spiro-thiadiazoline with 4-chlorophenyl | <0.4 |
| OGM23 | 5-Cl-indolin-2-one spiro-thiadiazoline with 1-naphthyl | 5.036 |
| OGM24 | 5-Cl-indolin-2-one spiro-thiadiazoline with 6-methoxy-2-naphthyl | 45.868 |
| OGM26 | 5-F-indolin-2-one spiro-thiadiazoline with 6-methoxy-2-naphthyl | 0.708 |

TABLE 4-continued
Medicinal Chemistry Data.
| Compound Number | Compound Structure | EC50 (μM) |
|---|---|---|
| OGM27 | 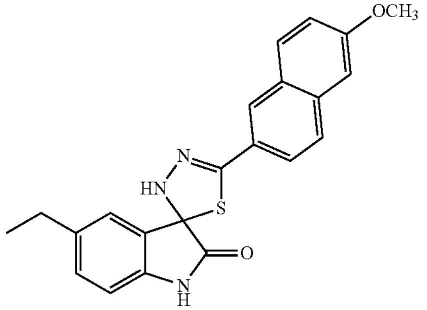 [SMILES: CCc1ccc2c(c1)C1(NN=C(c3ccc4cc(OC)ccc4c3)S1)C(=O)N2] | >10 |
| OGM28 | 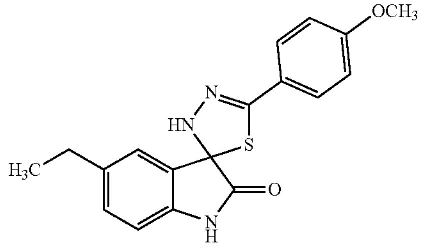 [SMILES: CCc1ccc2c(c1)C1(NN=C(c3ccc(OC)cc3)S1)C(=O)N2] | >10 |
| OGM29 | 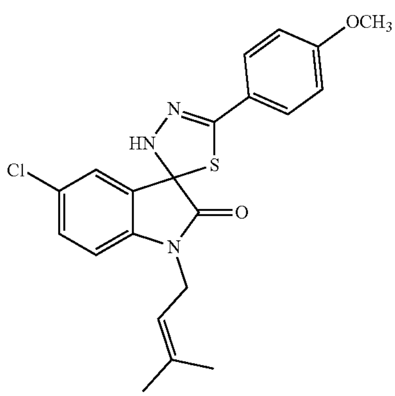 [SMILES: COc1ccc(C2=NNC3(S2)C(=O)N(CC=C(C)C)c2ccc(Cl)cc23)cc1] | >10 |
| OGM30 | 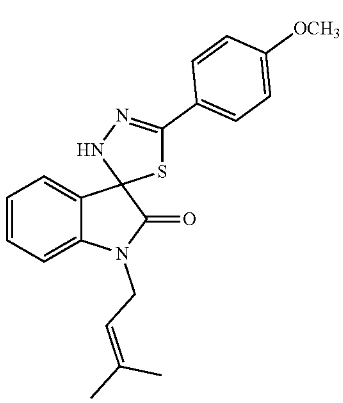 [SMILES: COc1ccc(C2=NNC3(S2)C(=O)N(CC=C(C)C)c2ccccc23)cc1] | >10 |
| OGM31 | | 9.082 |
| OGM32 | | >10 |
| OGM33 | | >10 |
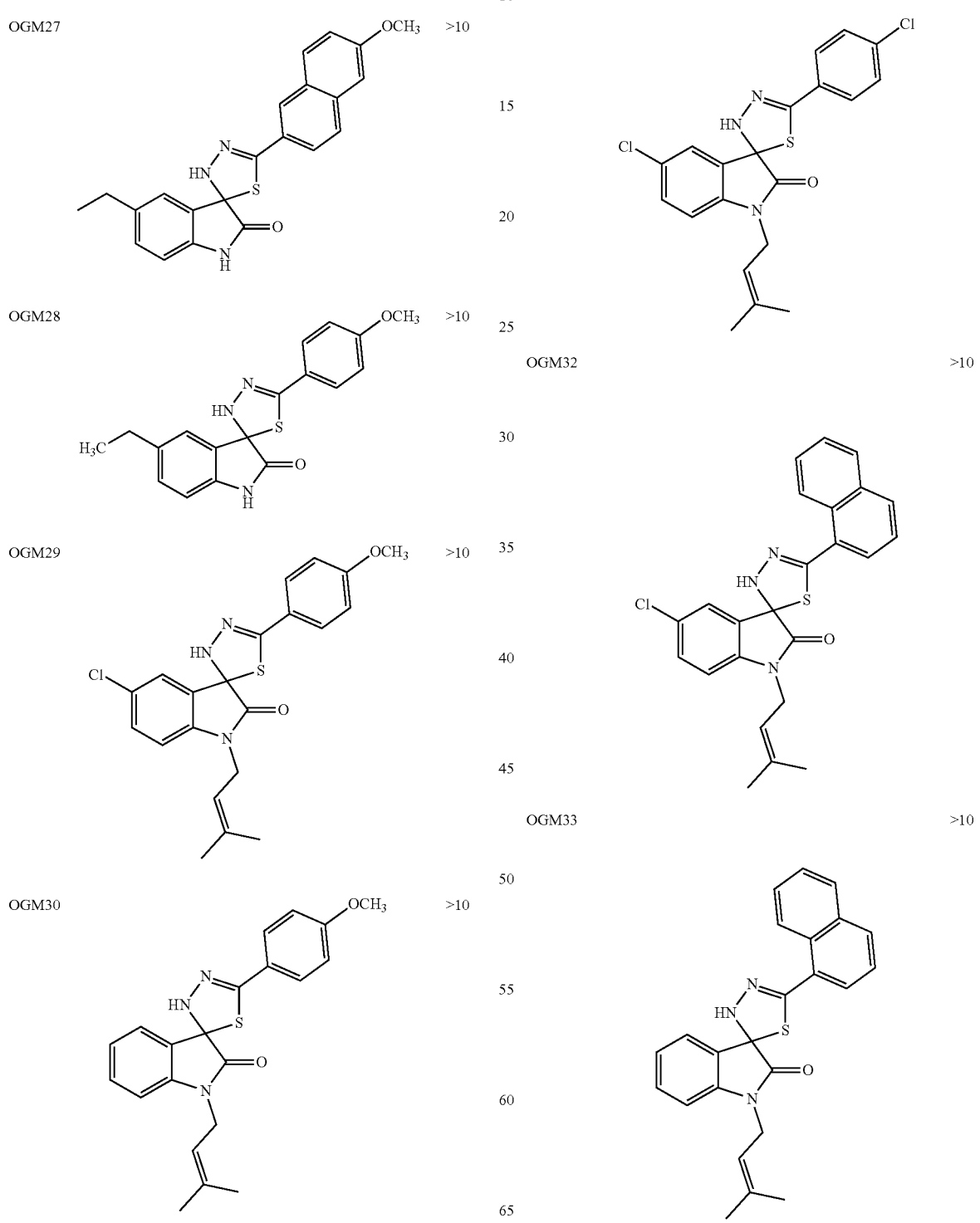

TABLE 4-continued

Medicinal Chemistry Data.

| Compound Number | Compound Structure | EC50 (μM) |
|---|---|---|
| OGM34 | 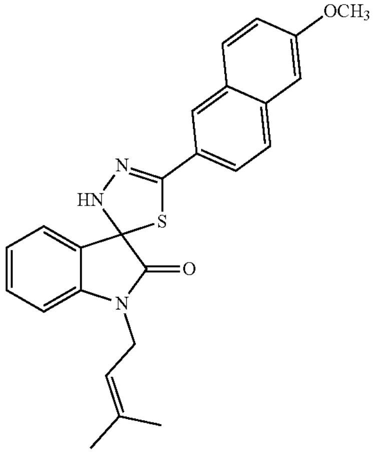 [SMILES: COc1ccc2cc(C3=NNC4(S3)C(=O)N(CC=C(C)C)c3ccccc34)ccc2c1] | >10 |
| OGM35 | 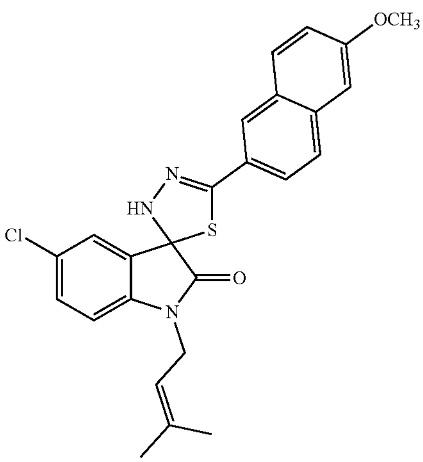 [SMILES: COc1ccc2cc(C3=NNC4(S3)C(=O)N(CC=C(C)C)c3ccc(Cl)cc34)ccc2c1] | >10 |
| OGM38 | 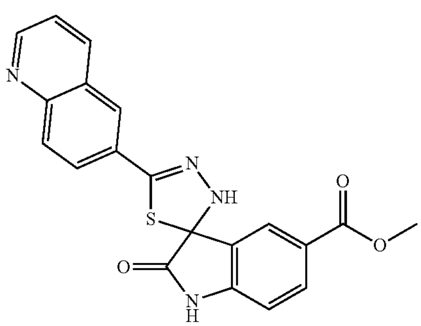 [SMILES: COC(=O)c1ccc2c(c1)C1(NN=C(c3ccc4ncccc4c3)S1)C(=O)N2] | 3.69 |
| OGM41 | 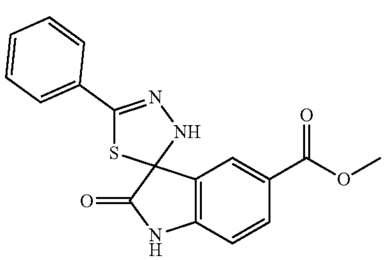 [SMILES: COC(=O)c1ccc2c(c1)C1(NN=C(c3ccccc3)S1)C(=O)N2] | 2.263 |
| OGM43 | 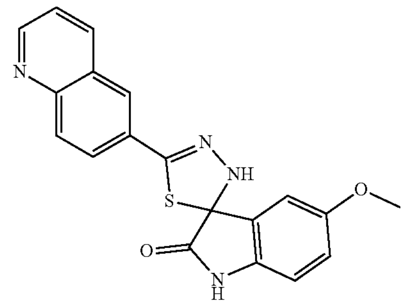 [SMILES: COc1ccc2c(c1)C1(NN=C(c3ccc4ncccc4c3)S1)C(=O)N2] | >10 |
| OGM44 | 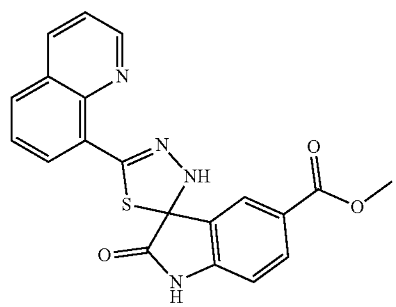 [SMILES: COC(=O)c1ccc2c(c1)C1(NN=C(c3cccc4cccnc34)S1)C(=O)N2] | 2.915 |
| OGM45 | 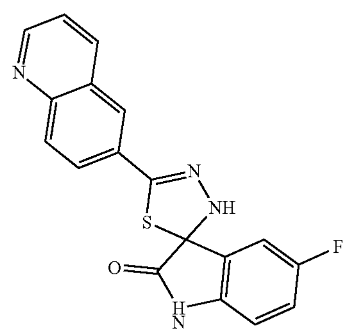 [SMILES: O=C1Nc2ccc(F)cc2C12NN=C(c1ccc3ncccc3c1)S2] | 10 |
| OGM46 | 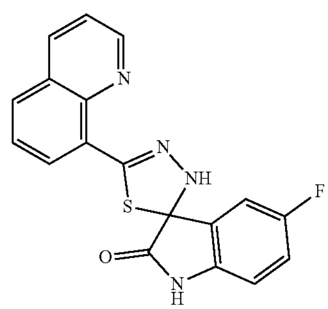 [SMILES: O=C1Nc2ccc(F)cc2C12NN=C(c1cccc3cccnc13)S2] | 1.466 |

TABLE 4-continued

Medicinal Chemistry Data.

| Compound Number | Compound Structure | EC50 (μM) |
|---|---|---|
| OGM47 | 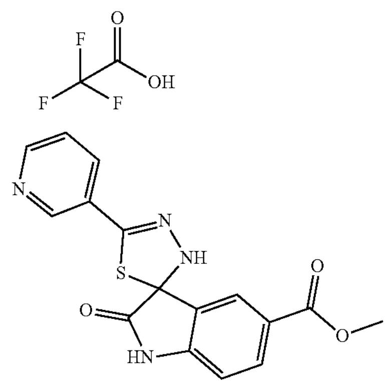 | >10 |
| OGM48 | 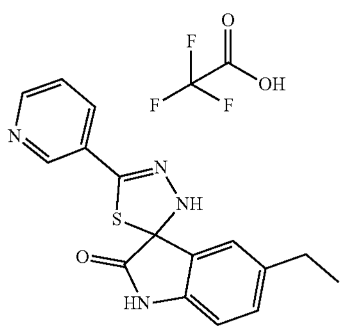 | >10 |
| OGM49 | 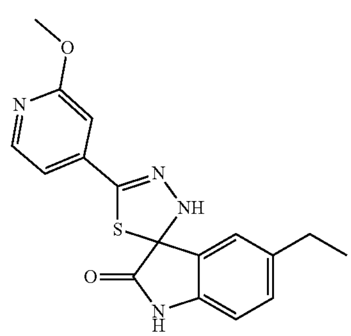 [SMILES: CCc1ccc2c(c1)C1(NN=C(c3ccnc(OC)c3)S1)C(=O)N2] | 1.089 |
| OGM50 | 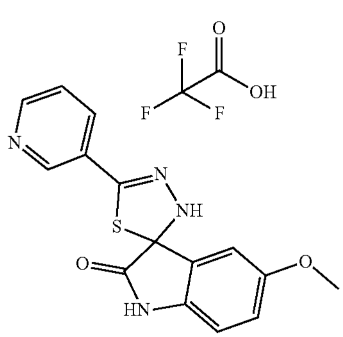 | 1.858 |
| OGM51 | 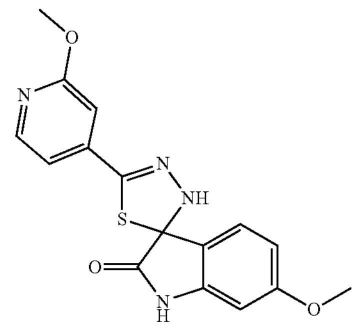 [SMILES: COc1ccc2c(c1)NC(=O)C21NN=C(c2ccnc(OC)c2)S1] | 1.436 |
| OGM52 | 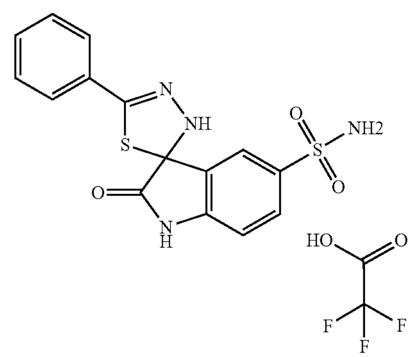 | 0.822 |
| OGM53 | 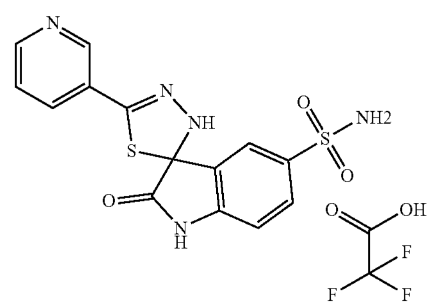 | 0.9 |
| OGM84 | 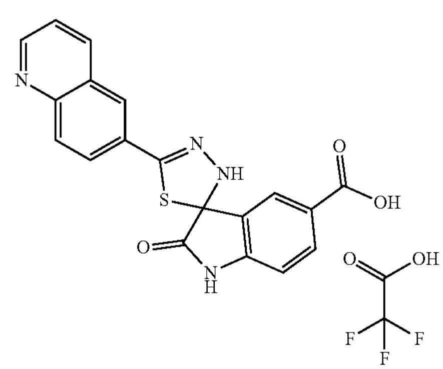 | 4.77 |

TABLE 4-continued

Medicinal Chemistry Data.

| Compound Number | Compound Structure | EC50 (μM) |
|---|---|---|
| OGM56 | (structure) | 3.582 |
| OGM57 | (structure) | 0.805 |
| OGM58 | (structure) | <0.4 |
| OGM60 | (structure) | <0.4 |
| OGM63 | (structure) | 3.52 |

Example 6: GPCR Activity Based on Chemical Structure

Figure 2C:
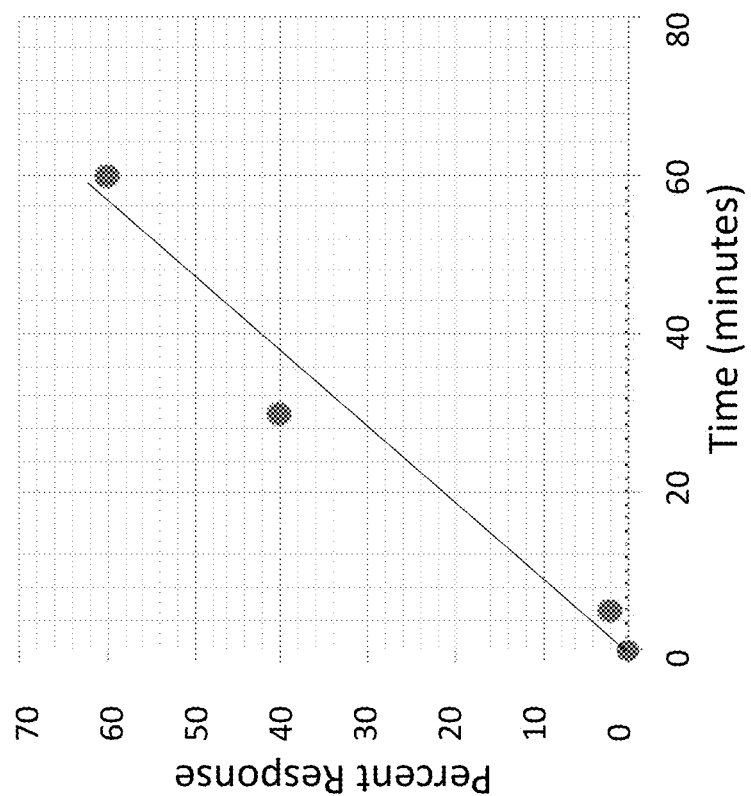
Figure 2B:
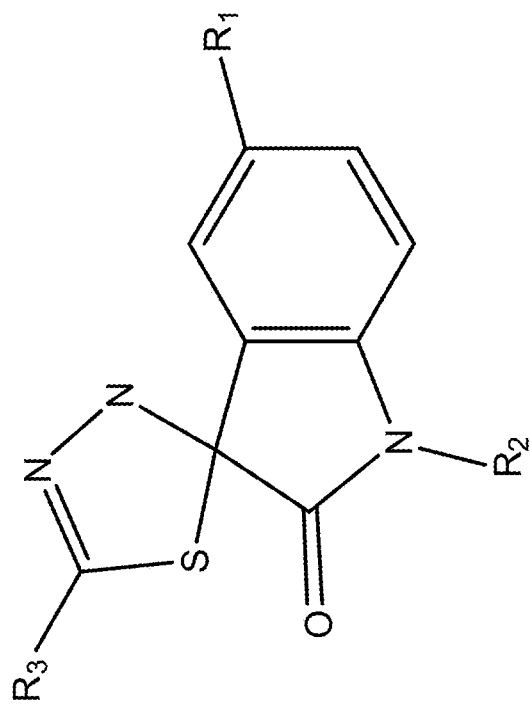

Since GPCRs represent >30% of targets for FDA-approved small molecules and are known to modulate cell migration, activity against 158 GPCRs was assessed based on their chemical structures. GPCRs (158) were tested for agonist and antagonist activity at 10 μM. Only GPR68, LPA1 and GPR14 (UT2R) showed significant activity against LPAR1, UT2R, and GPCR68. See FIG. 2A. Chemical segregation analysis of zebrafish phenotype was conducted to further identify the inhibitory activity responsible for the zebrafish phenotype. Commercially available inhibitors of LPAR1 (Ki16425) and GPR14 (SB657510) were both assayed and failed to induce a noticeable phenotype at concentrations up to 200× the IC50. A small scale structure-activity relationship study around the core pharmacophore of OGM (see FIG. 2B, showing the core scaffold for OGM derivatives) generated molecules that were similar to OGM but did not have LPAR1 activity. The identities of the R groups in FIG. 2B are shown below in Table 5.

Figure 2D:
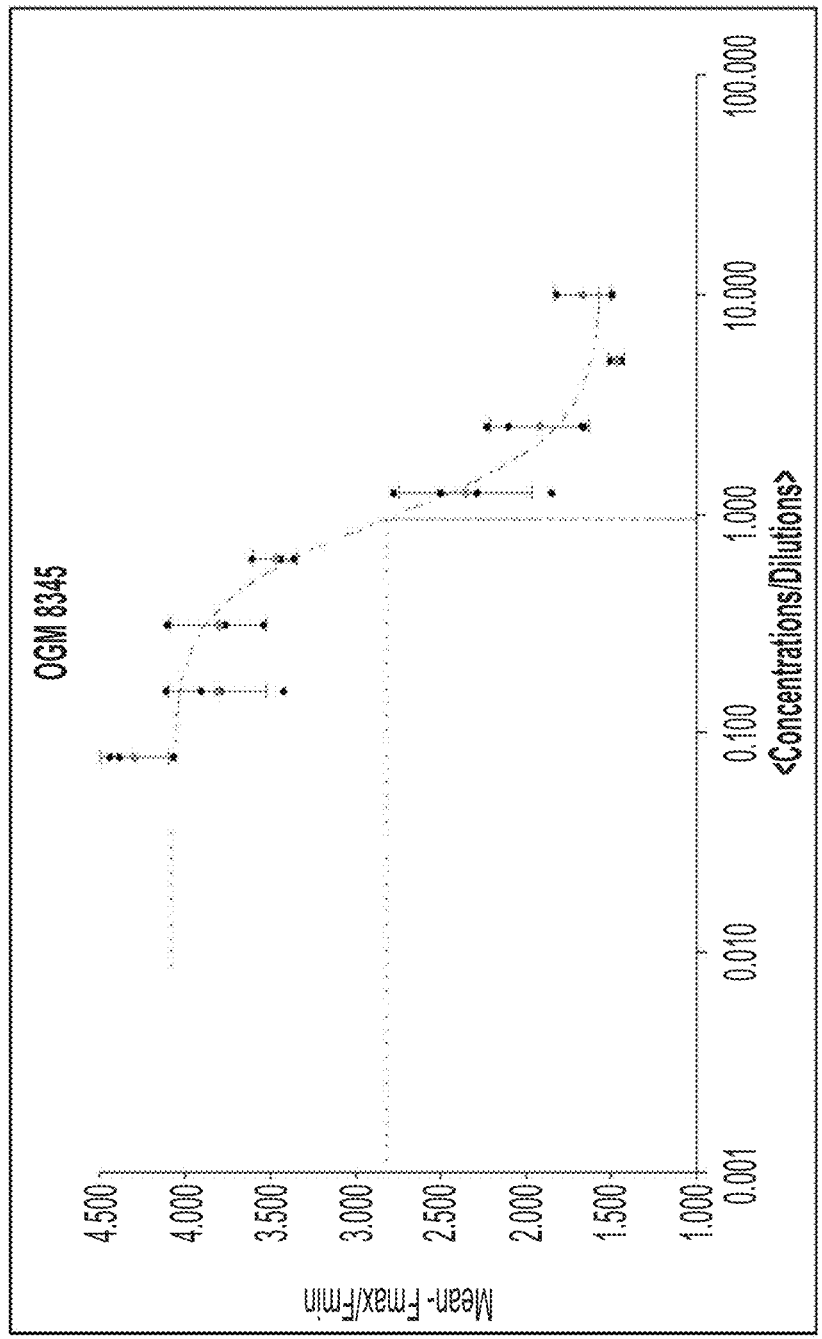

Chemical Linkage analysis was used to show that loss of LPA activity did not correlate with loss of phenotype in zebrafish. Commercial inhibitors of UT2R (SB657510, Sigma™) and LPA1R (Ki16425, Sigma™) did not recapitulate phenotype. See FIG. 2C, which shows the results of the Millipore GPCR screen. Chem1-GPR68 reporter cells were treated with 20 uM OM8345 for 2 hours and then rinsed with HBSS. These cells were then assayed for GPR68 at different increments of time, revealing the reversible inhibition of GPR68. The GPR68 inhibitory activity of OGM analogs segregated with the ability of the molecule to induce the phenotype in zebrafish. Neural crest progenitors labeled with In situ hybridization of FoxD3 show normal formation of the progenitor pool. See FIG. 2D.

TABLE 5

Selected Compounds of interest.

| ID | R1 | R2 | R3 | Phenotype | GPR68 (μm) | Lpa1 (μm) |
|---|---|---|---|---|---|---|
| OGM5 | H | Methyl | Benzyl | Y | 0.81 | — |
| OGM3 | Methyl | H | Benzyl | Y | 0.76 | 6.4 |
| OGM2 | Ethyl | H | Benzyl | Y | 0.71 | — |
| OGM4 | Ethyl | H | 2-phenyl | Y | 3.4 | 1.4 |
| OGM6 | H | Methyl | Naphthyl | Y | 1.5 | — |

TABLE 5-continued

Selected Compounds of interest.

| ID | R1 | R2 | R3 | Phenotype | GPR68 (µm) | Lpa1 (µm) |
|---|---|---|---|---|---|---|
| OGM1 | Ethyl | H | Naphthyl | Y | 0.16 | 8.7 |
| LPAi | — | — | — | N | — | 0.25 |
| UT2i | — | — | — | N | — | — |

Figure 3A:
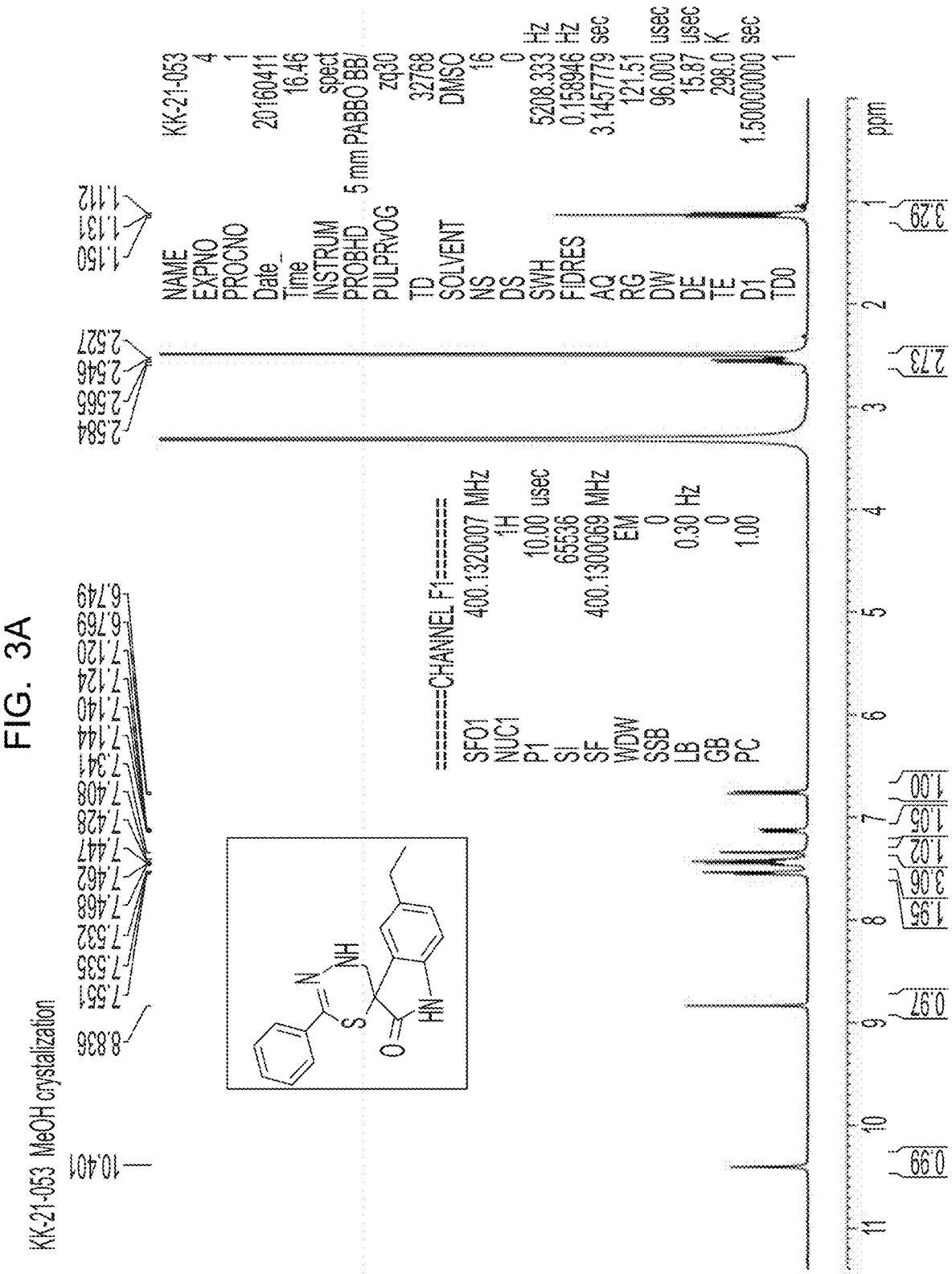
FIG. 3A and FIG. 3B. HNMR and LCMS of resynthesis of OGM2.
Figure 3B:
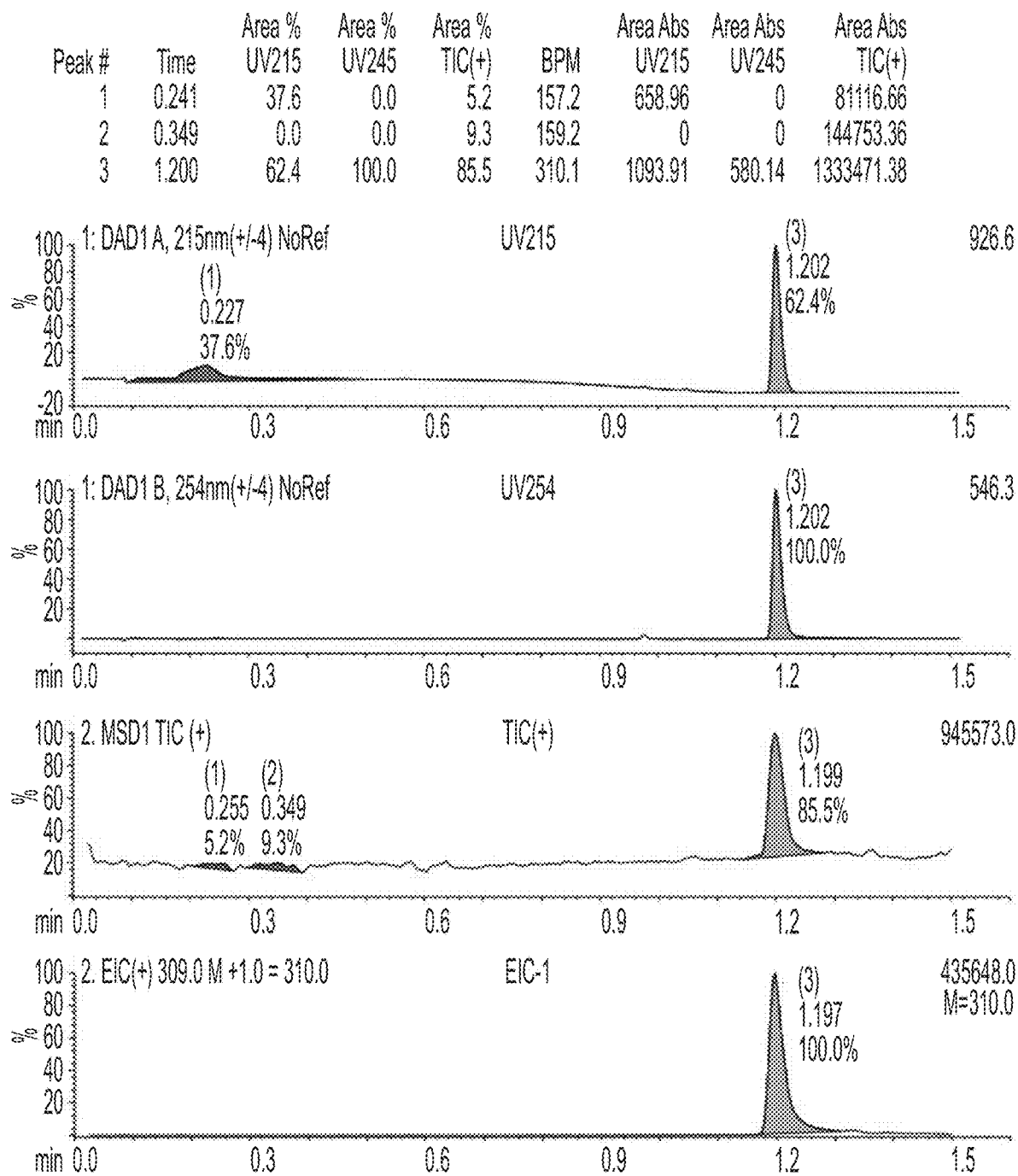

Additional experiments, OGM2 resynthesized and used (due to its submicromolar potency and GPR68 specificity) were performed. See FIG. 3A (HNMR of resynthesis of OGM2) and FIG. 3B (LCMS of resynthesis of OGM2). To test the possibility of OGM2 being an irreversible inhibitor, Chem1-OGR1 cells (Millipore™) were incubated with 10 µM OGM2 for 4 hours, and after removing the compound stimulated with pH 6.4 medium. GPR68 activity is restored rapidly after washout of inhibitor. Time till 50% max ~52 minutes. The signal returned back towards baseline uninhibited levels in a rapid and time-dependent manner. Taken together, these data suggest that OGM2 is a reversible and highly specific inhibitor of GPR68.

Example 7: GPR68 Knockdown Recapitulated OGM Induced Zebrafish Phenotype

Zebrafish GPR68 and human GPR68 have a high degree of homology, with 58.3% identity and 75.2% similarity (see Table 6, below), which shows the identity and similarity between human and zebrafish orthologs). Compared to this, in zebrafish the proton-sensing GPCR family members GPR4 and GPR65 are 41.45% and 28.04% similar, respectively (see Table 7, below), which shows similarity of acid-sensing GRCRs in zebrafish). To determine if the loss of GPR68 activity causes neural crest defects in zebrafish we knocked down GPR68 using morpholino oligonucleotides. We found that the neural crest-specific phenotypes of iridophores, melanocyte, and craniofacial cartilage were all disrupted in a dose-dependent manner using 1.5 ng and 3 ng morpholino, the same amount of mismatch morpholino did not recapitulate the result. Additionally, the wavy notochord which is not known to be a neural crest-related phenotype was recapitulated in morphants as well. Taken together, the data suggest that the phenotypes seen in OGM treatment are due to loss of GPR68 activity and include causes defective neural crest development and wavy notochord formation.

TABLE 6

Degree of Homology.

|  | Identity % (AA) | Similarity % (AA) |
|---|---|---|
| Hs. GPR65 vs zfGPR65 | 39 | 58.8 |
| Hs. GPR68 vs zfGPR68 | 58.3 | 75.2 |
| Hs. GPR4 vs zfGPR4 | 74.1 | 85.2 |

TABLE 7

Similarity of GPCR Family Members.

|  | zfGPR65 | zfGPR68 | zfGPR4 |
|---|---|---|---|
| zfGPR65 | 100 | 28.04 | 30.61 |
| zfGPR68 | 28.04 | 100 | 41.15 |
| zfGPR4 | 30.61 | 41.45 | 100 |

Figure 4A:
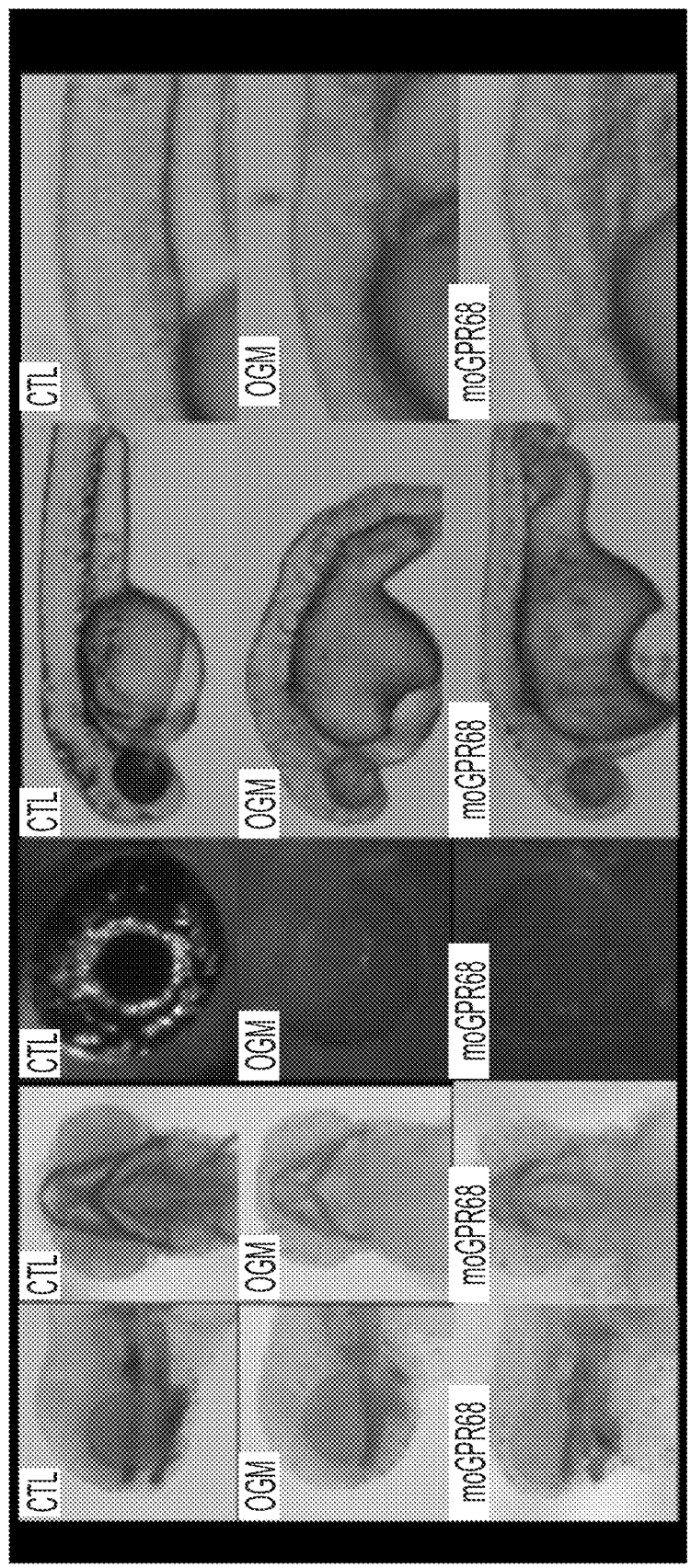
FIG. 4A through FIG. 4D. GPR68 Knockdown recapitulated OGM induced zebrafish phenotype.
Figures 4B, 4C, 4D:
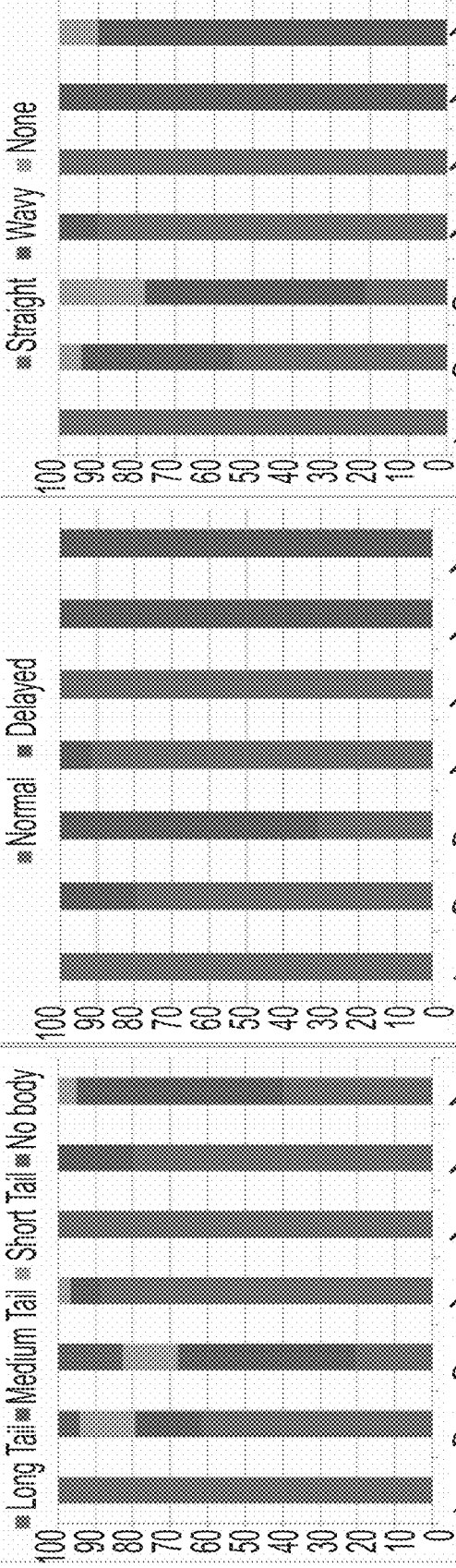

FIG. 4 shows data from a sample dose-response assay of OGM2 (Chem1-GPR68 assay) that shows that morpholino knockdown of GPR68 induces craniofacial dysmorphogenesis, loss of iridophores, disrupted pigmentation, and wavy notochord. An alcian blue stain of craniofacial cartilage seen laterally and dorsally show abnormalities: loss of iridophores (left), abnormal pigmentation (middle), and undulating/kinked notochord (right). See FIG. 4A. Doses of 3 ng Morpholino injections into zebrafish induced more embryos with phenotype than 1.5 ng. The 3 ng dose of mismatch morpholino had little effect. These phenotypes are consistent with 10 µM and 20 µM OGM treatments. See FIG. 4A, FIG. 4B, FIG. 4C, and FIG. 4D, which show that the genetic loss of GPR68 activity phenocopies the phenotype generated by OGM2 treatment. The phenotype is the consequence of loss of GPR68 activity in vivo.

Example 8: Gene Profiling Datasets Show that GPR68 Expression Correlates with Worse Prognosis and U87 Cells Respond to Acid Through GPR68

Figure 5A:
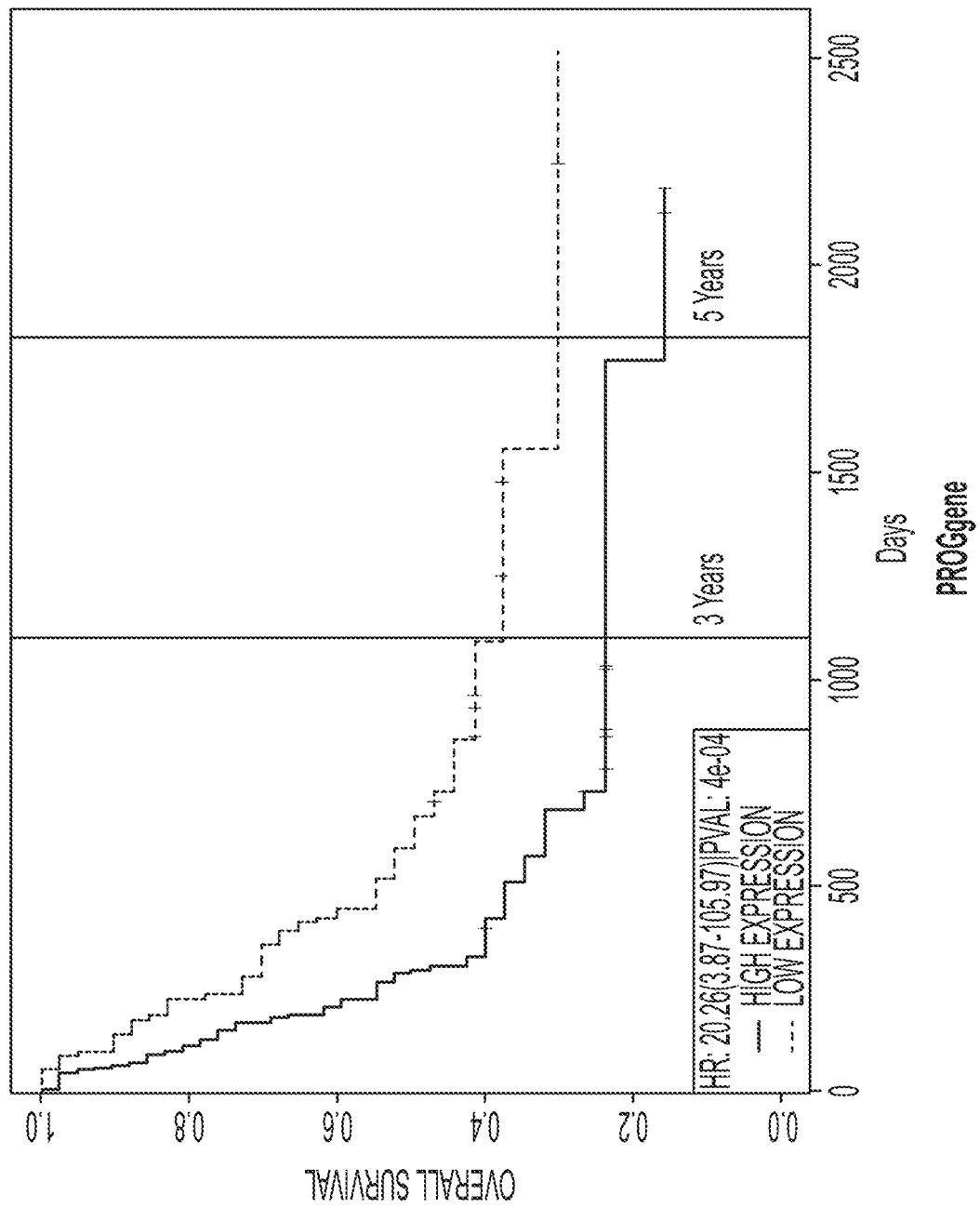
FIG. 5A and FIG. 5B. Gene profiling datasets.

Transcriptional profiling has been applied to 85 gliomas from 74 patients to investigate glioma biology, prognosticate survival, and define tumor sub-classes. All patients undergoing surgical treatment at the University of California, Los Angeles for primary brain cancers between 1996 and 2003 were invited to participate in this Institutional Review Board approved study. Seventy-four of the patients participating in this broad protocol were analyzed as part of this study if their initial tumor was diagnosed as a grade III (n=24) or IV (n=50) glioma of any histologic type on initial surgical treatment and fresh frozen material was obtained. Only grade III and IV gliomas were included in this study as the distinction between these grades is subtle and prone to misclassification. The time in days elapsed from resection to the day of death, or if the patient has remained alive, to the current day was recorded for all samples studied. Patient ages at diagnosis varied from 18 to 82 years. There were 46 females and 28 males. Probes were prepared using standard Affymetrix™ protocols, and hybridized to Affymetrix™ HG-U133A and HG-U133B arrays. The cohort was separated by High and low expression of GPR68 by above or below the median expression level. Survival of the cohort post-resection is plotted and found to be significantly different. See FIG. 5A.

Figure 5B:
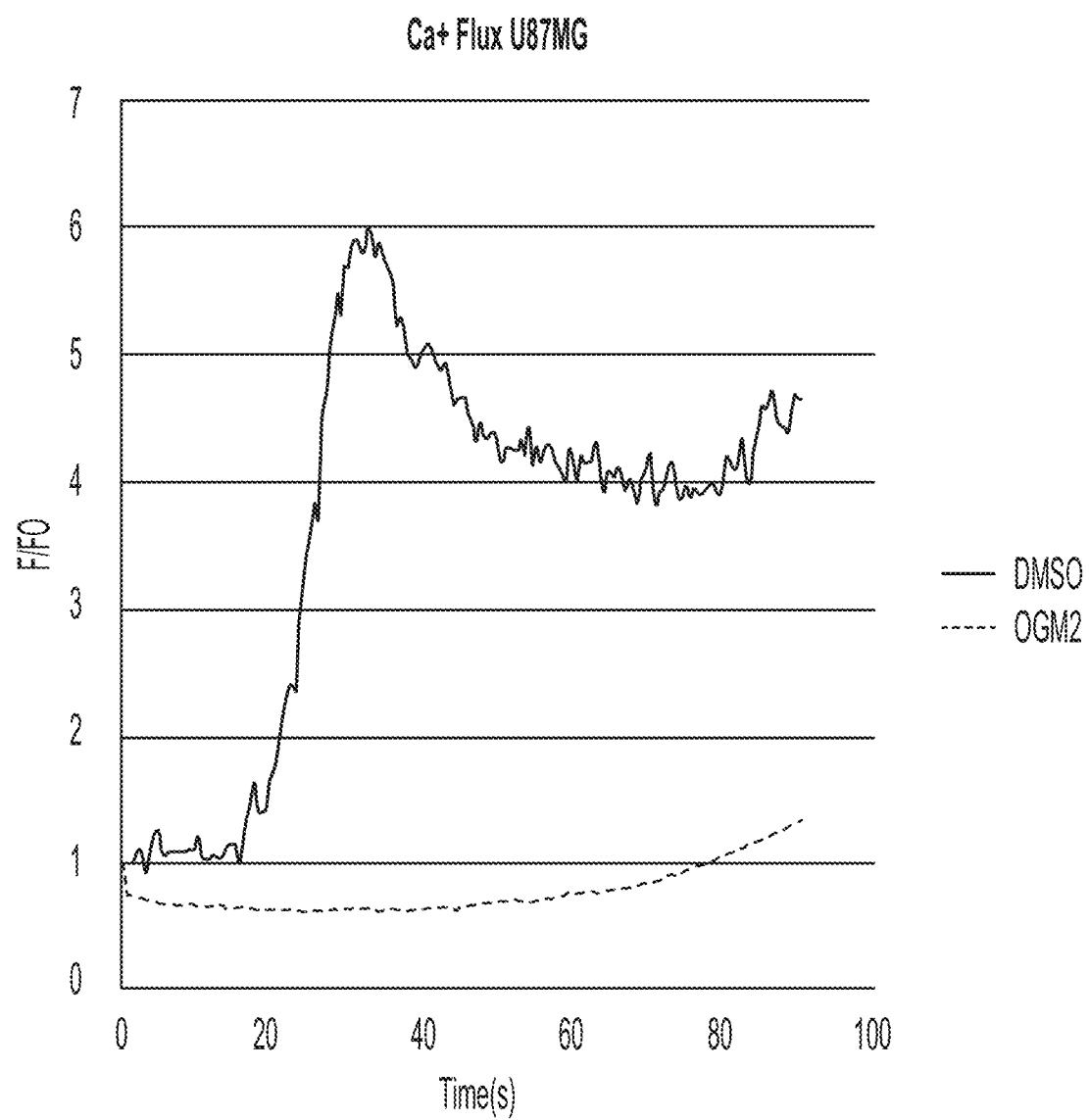

GPR68 is known to signal through Gq which results in a calcium flux out of the Endoplasmic reticulum. U87 glioblastoma cells were stained, using a calcium-sensitive vital dye Fluo-8, and stimulated with acidification of the media to pH6.4. The cells respond to the acidification with a burst of calcium release, this is inhibited by OGM2. See FIG. 5B.

Example 9: OGM Inhibits Human Melanoma Migration

Since there are numerous parallels are found between neural crest cells and cancer during migration, we examined whether OGM could inhibit the migration of cells in human melanoma cell lines (Oppitz et al., 2007; Schriek et al., 2005; Sinnberg et al., 2018). In a scratch assay for migration of 3 human melanoma cell lines A2058, MeWo, and WM115, OGM2 (5 uM) treated cells migrated significantly less than the vehicle treated cells. A2058, MeWo and WM115 cells were grown to confluence and a stripe of cells were denuded with a p200 pipette tip "scratch" and rinsed with PBS. Cells were treated with OGM or EIPA, or DMSO and incubated in low serum media. Imaging was done at 30 minutes after "scratch" and then 20 hours afterwards. Areas were then measured and normalized to the initial area. FIG. 6A shows representative images of WM115 cells used in the scratch assay; OGM and EIPA both prevent wound closure compared to DMSO (CTL).

Figure 6B:
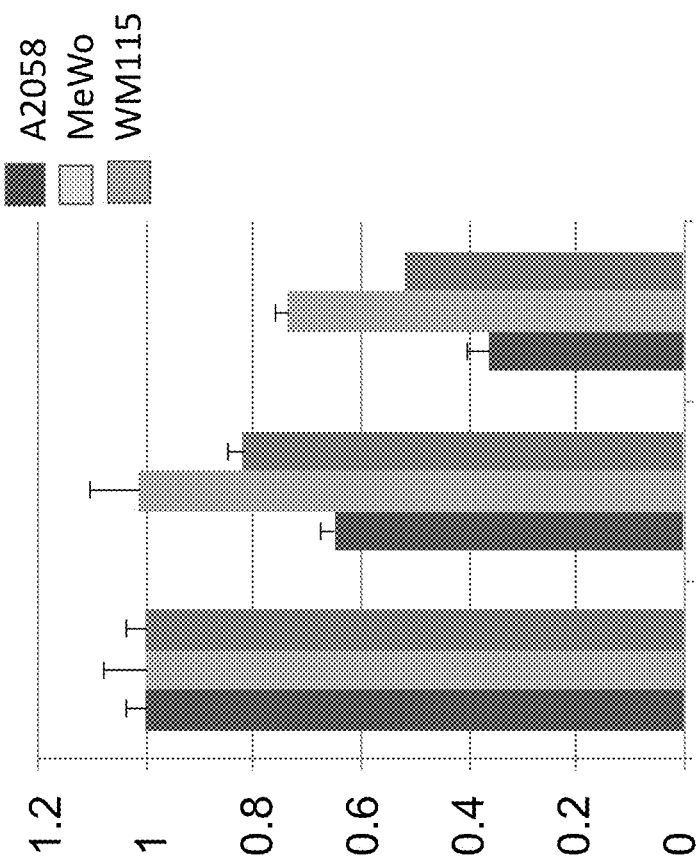
Figure 6A:
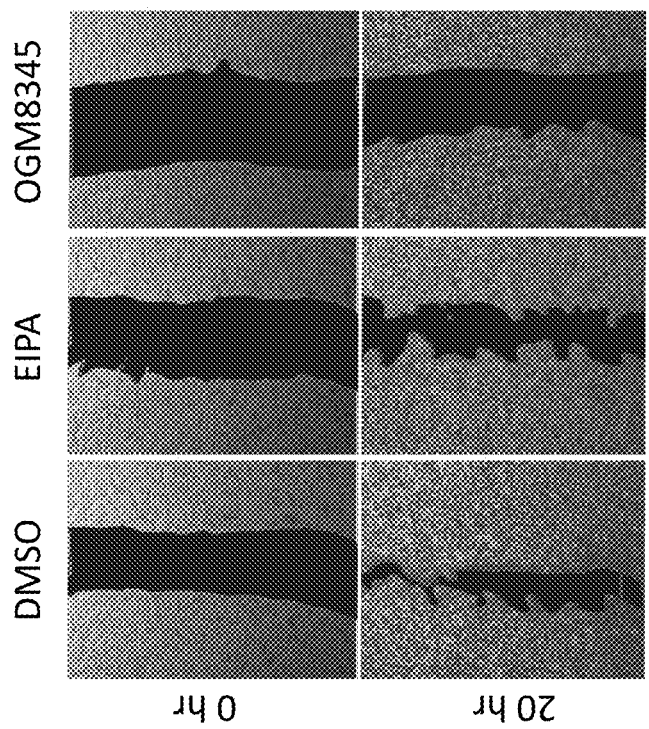
FIG. 6A is a set of photographs of a morpholino knock down experiment, showing that knock down of GPR68 in zebrafish recapitulate phenotypes of GPR68 inhibition by OGM molecules.
Figure 7:
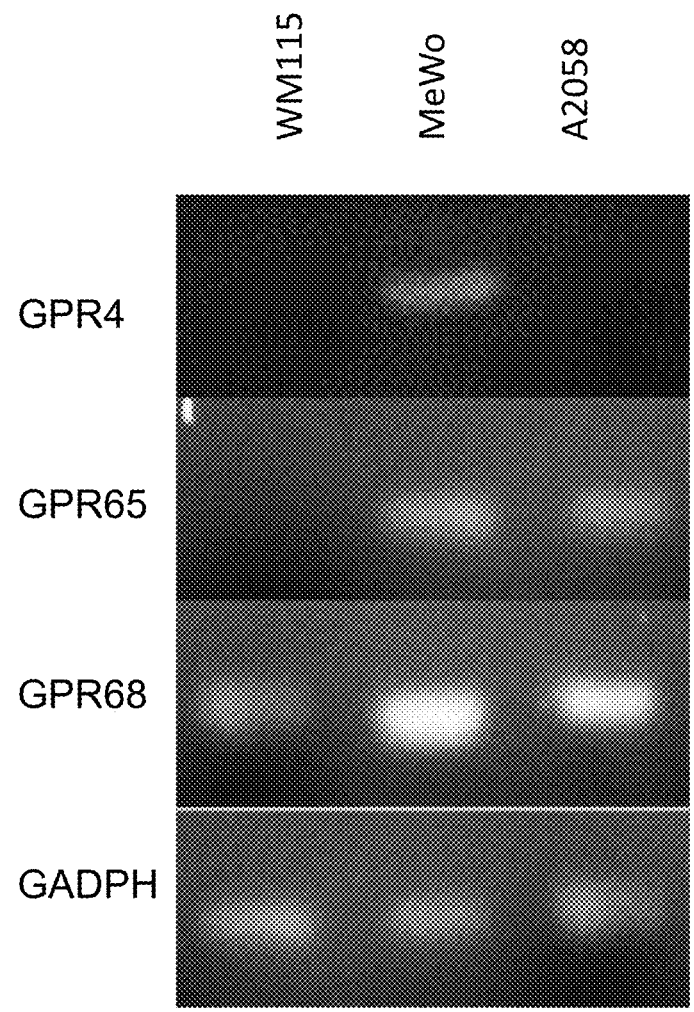
FIG. 7. RT PCR of proton-sensing GPCRs in human melanoma cell lines.
Figure 8D:
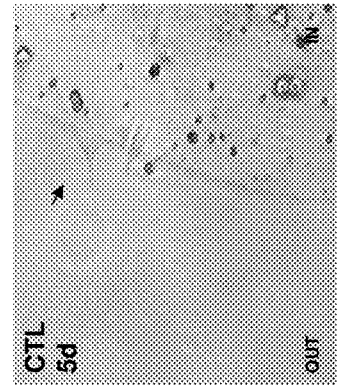
FIG. 8A through FIG. 8G.
Figure 8C:
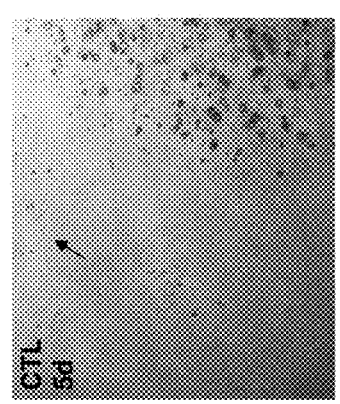
Figure 8F:
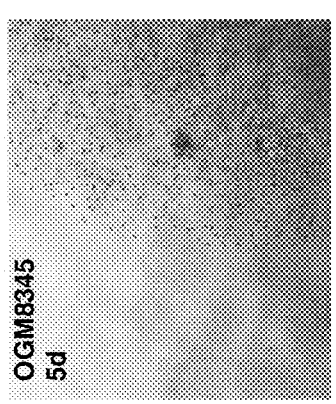
Figure 8B:
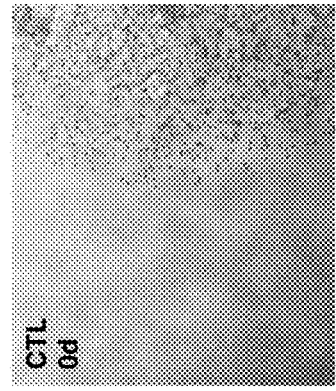
Figure 8E:
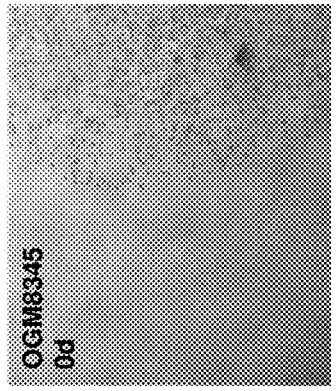
Figure 8A:
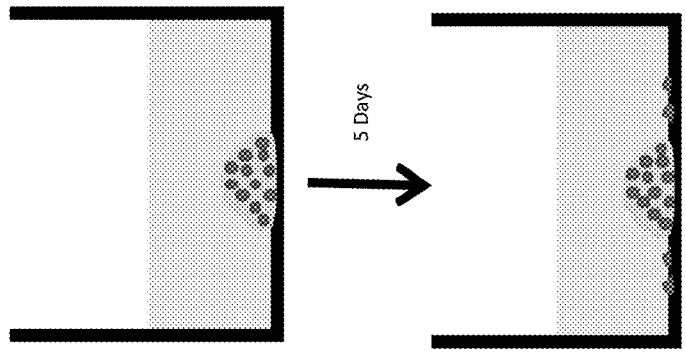
Figure 8G:
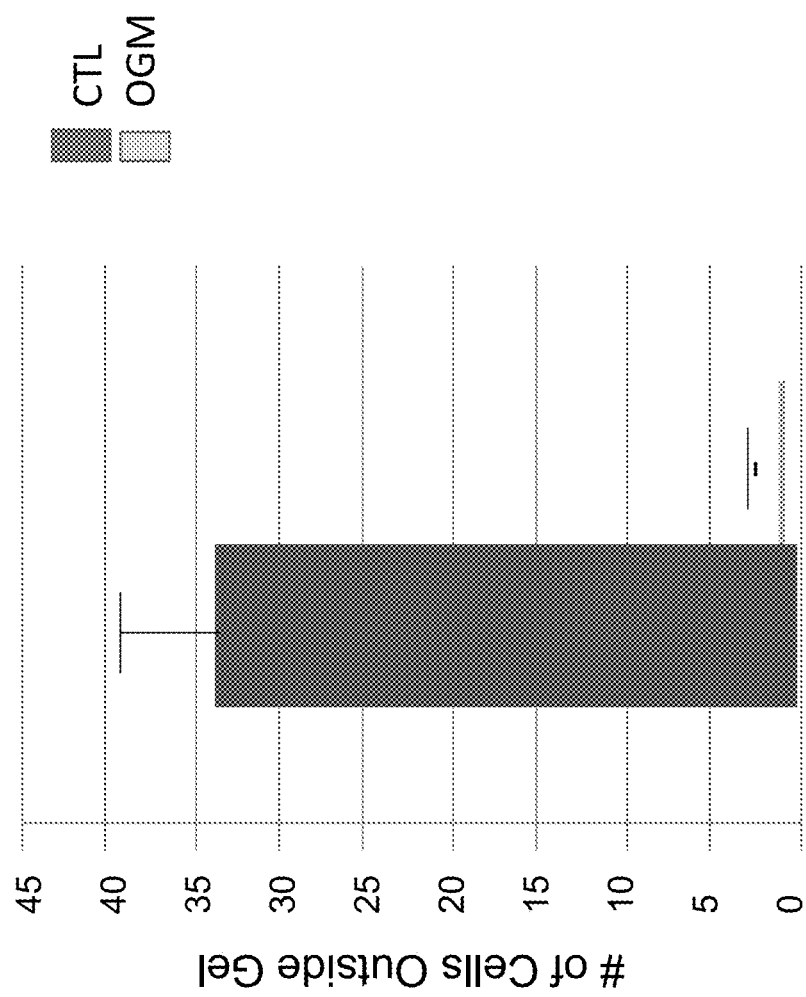

FIG. 6B shows quantification of inhibition in scratch assays across three melanoma lines. OGM inhibited migration in WM115, A2050 and MEWO cell lines. EIPA inhibited migration in WM115 and A2058 but not MeWo lines. Previous studies with the MV3 melanoma cell line have shown that disruption of proton efflux with EIPA inhibition of NHE1 can also reduce melanoma motility (Ludwig et al., 2013; Schneider et al., 2009; Stock et al., 2007, 2005; Stüwe et al., 2007). Here, the data show that, although this effect is significant in A2058 and WM115, MeWo appears refractory to the inhibition (FIG. 6B). Although the expression of GPR68 and other proton-sensing receptors have been characterized in various skin cancers (Merkel cell carcinoma, dermatofibrosarcoma protuberans, atypical fibroxanthoma, and pleomorphic dermal sarcoma), expression in melanoma cell lines has not investigated (Nassios et al., 2019). All three of these melanoma cell lines express GPR68, but only WM115 cells did not express GPR4 or GPR65. See FIG. 7.

Furthermore, in a 3D model of melanoma extravasation, OGM treated WM115 cells migrated significantly less than the vehicle treated cells (see FIG. 8). FIG. 8A is a schematic of the agarose drop assay. WM115 cells were mixed into a low melt agarose solution and single 10 μL drops were seeded onto cell culture plates. After solidifying, media containing OGM (5 μM) or CTL (DMSO 005%) was added and wells were observed 5 days later. Immediately after media addition no cells are on the plate outside of the agarose gel in CTL or OGM. Five days after seeding cells are observed outside of the gel (Black arrows) in CTL but not in OGM. Close observation of CTL reveals cells crossing out of the gel drop (Black Arrowheads). Quantification on the number of cells that escaped from an average of 5 gel drop replicates. FIG. 8B through FIG. 8F show the cells after media addition. No cells are on the plate outside of the agarose gel in CTL or OGM. Five days after seeding, cells are observed outside of the gel (arrows) in CTL but not in OGM. Close observation of CTL reveals cells crossing out of the gel drop (arrowheads). FIG. 8G shows the quantification on the number of cells that escaped from an average of 5 gel drop replicates. Taken together this data suggests that GPR68 plays a critical role in melanoma migration in vitro.

Example 10: Variant Rs61745752 is a Functional c-Terminal Truncation

Given the association of rs61745752 with cancer (Table 7), we sought to determine the functional consequence of the variant which causes truncation after amino acid 335 (E336X). Mutations in the C-terminal tail of GPCRs can have a number of consequences, including loss of desensitization, and inactivation. GPCR desensitization is modulated through beta-arrestin binding to domains that are defined by GIRK phosphorylation.

Prediction of putative binding sites for beta-arrestin binding identified a putative beta-arrestin binding site in the C-terminal cytosolic tail of the receptor, downstream of the early termination site (see FIG. 10A, a phosphocode prediction of beta-arrestin binding site downstream of amino acid 335). The sequence aligned with known beta-arrestin interaction domains of Rhodopsin and Vasopressin 2.

Figures 10B, 10C:
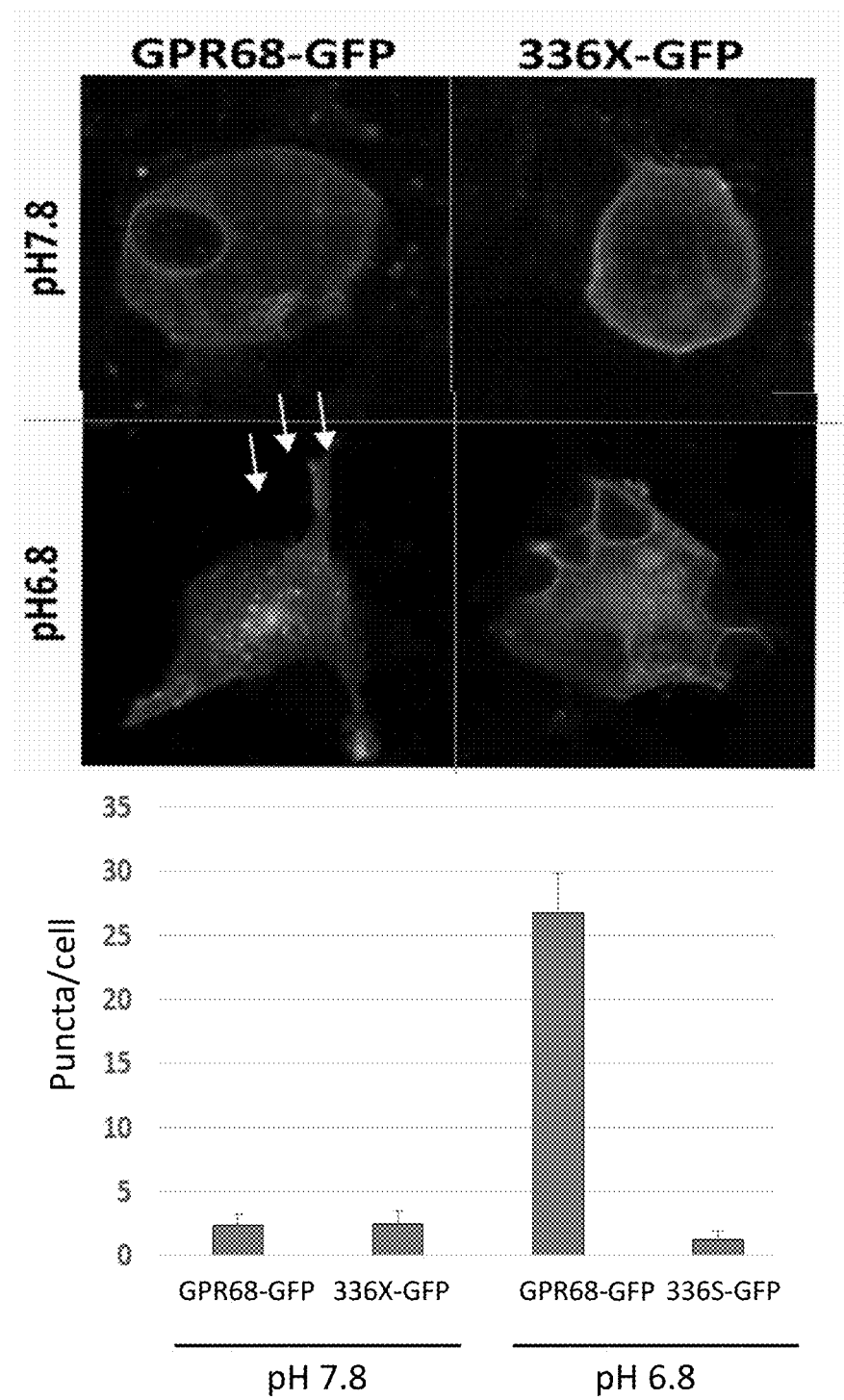

Transfection of native GFP-tagged (GPR68-GFP) and truncated GFP-tagged GPR68 (336X-GFP) in HEK293T revealed that the variant (335X-GFP) fails to internalize in response to stimulation, while the full-length (GPR68-GFP) internalizes in response to stimulation. See FIG. 10B and FIG. 10C. For the data shown in FIG. 10B, GPR68-GFP and 336X-GFP transfected HEK293 cells were stimulated with pH 6.8 media for 5 minutes. GPR68-GFP had puncta (white arrows) in the cell, but 336X-GFP did not form puncta under acidic conditions. FIG. 10C shows the quantitation of the number of puncta in each cell (n=20).

Figure 10D:
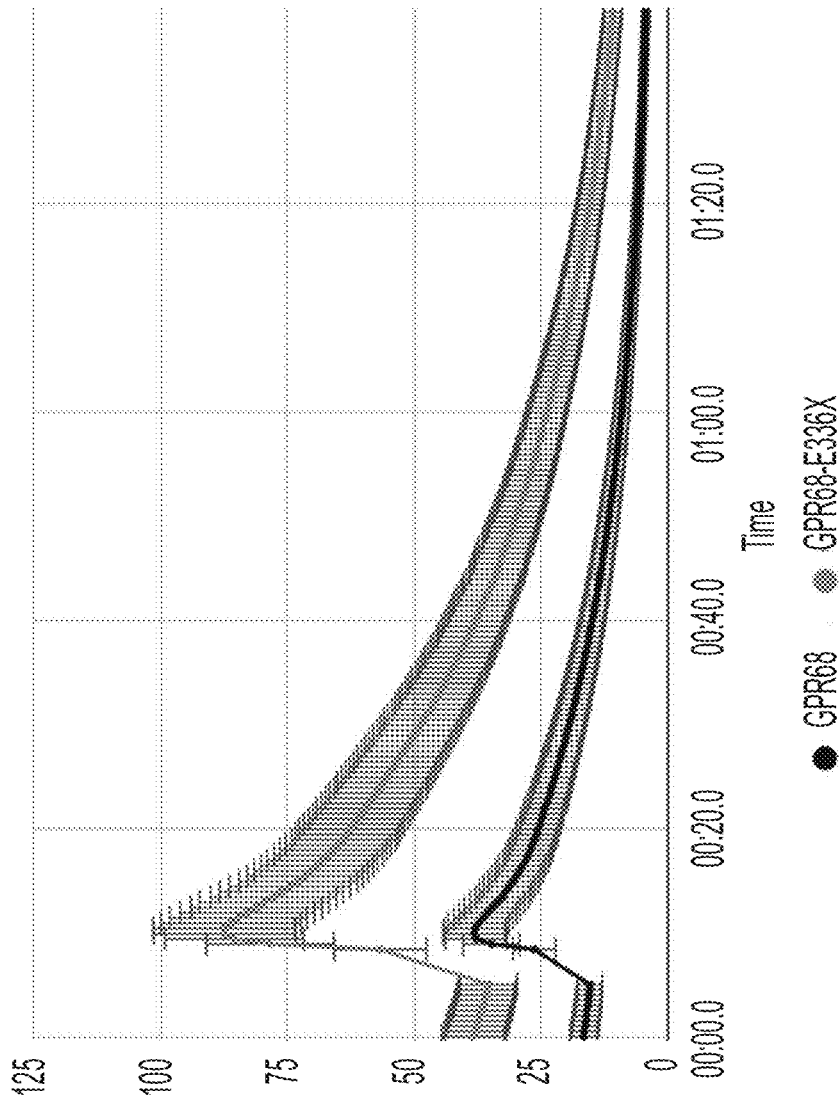

293T cells were transfected with GPR68 and or E336X variant, 24 hours later cells were stained with fluo8 calcium indicator. Kinetic imaging was conducted with Lionheart HCS with a 5 second baseline reading prior to stimulation with acidification. See FIG. 10D. The variant has higher baseline levels of calcium in the cytosol which are increased upon stimulation.

Figure 11:
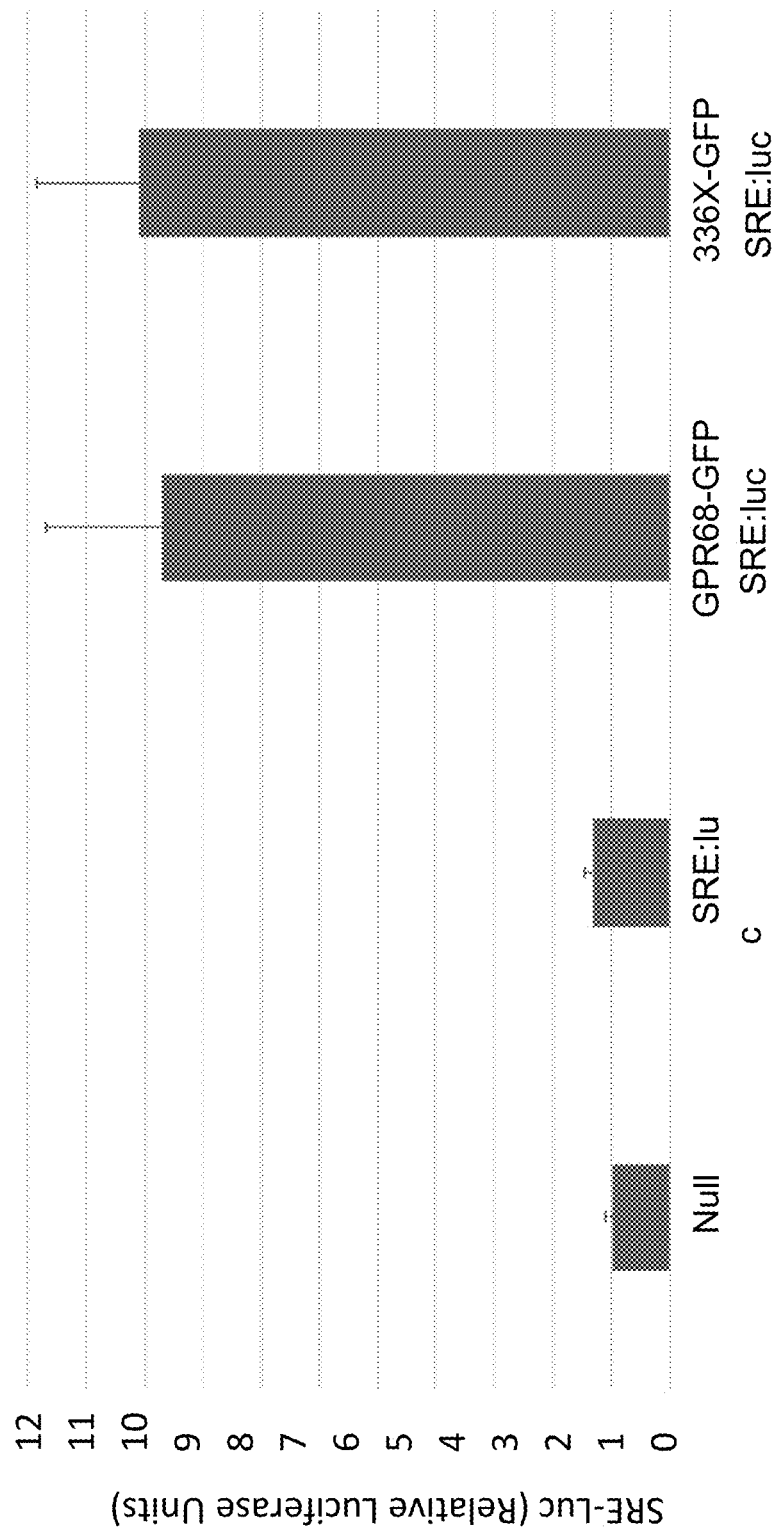
FIG. 11. E336X-GFP plasmid is still active in SRE-luciferase assay.

Loss of internalization can indicate loss of activity or loss of the ability to internalize through beta-arrestin. We assessed the activity of the truncation variant (336X-GFP) and found that the truncation variant still retained activity in a SRE (serum response element) responsive luciferase assay, which is activated by GPCR stimulation, particularly those coupled with Gi and Gq, through activation of the MAPK pathway. See FIG. 11, which shows that the E336X-GFP plasmid is still active in SRE-luciferase assay. The composite of results from the Serum responsive element (SRE-) luciferase assay showed low levels of activity in HEK293T cells. Compared to GFP controls, GPR68-GFP and 336X-GFP transfected cells had higher levels of activity. (n=3 biological replicates done in triplicate). Furthermore, the activity of the truncation variant was still inhibited by OGM. FIG. 12 shows representative results from a serum responsive element (SRE-) luciferase assay. The SRE shows low levels of activity in HEK293T cells. Compared to GFP controls, GPR68-GFP and 336X-GFP transfected cells had higher levels of activity. Incubation with OGM 10 μM reduced the level of luciferase activity in both GPR68-GFP and 336X-GFP conditions (n=3, technical replicates). Taken together the data suggests that rs61745752 is aberrantly active through the loss of desensitization.

Example 11: GPR68 Activity Destabilized MCF7 Spheroids

Figure 13A:
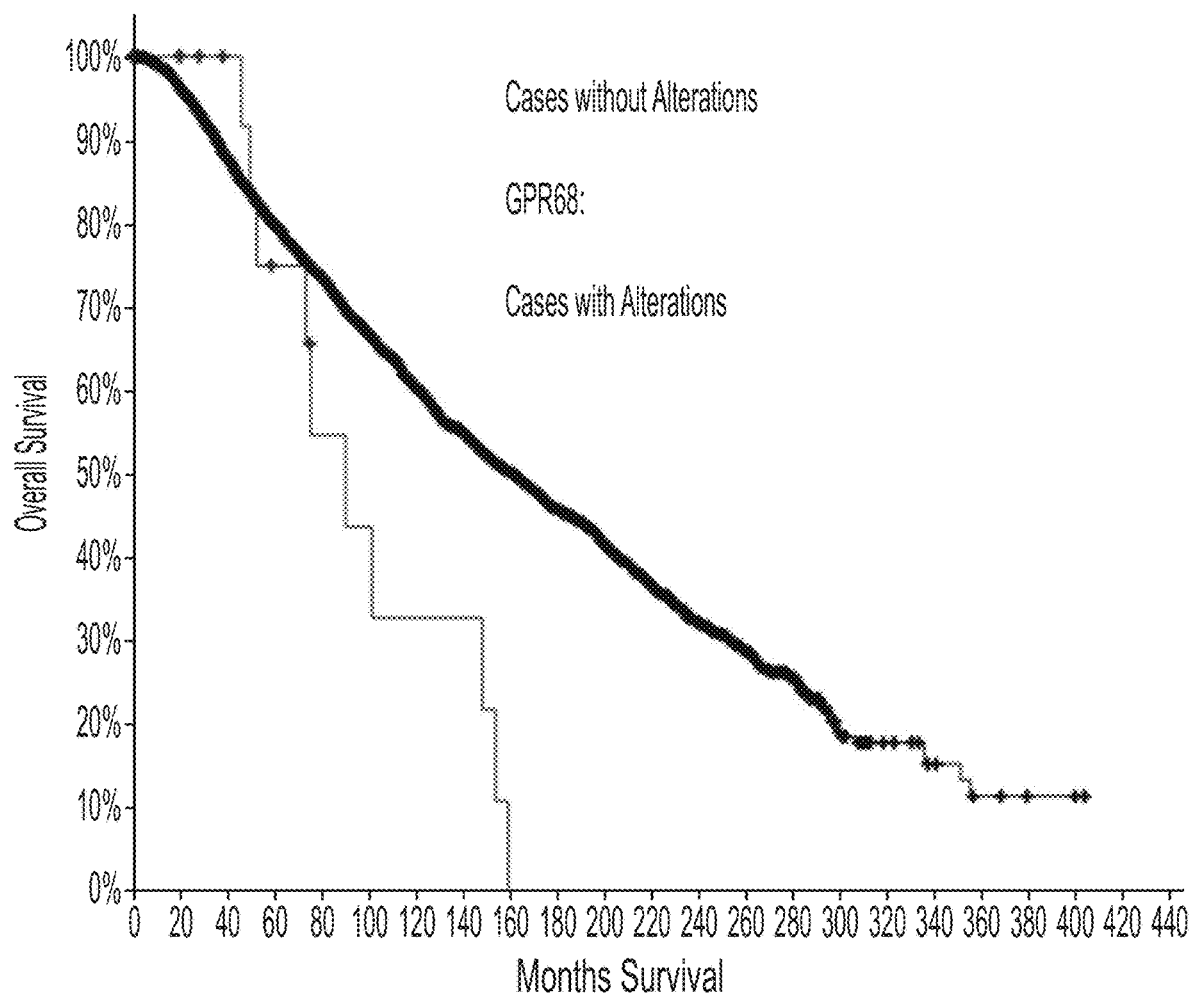
FIG. 13A through FIG. 13C. Mutations in GPR68 correlate with poor prognosis in breast cancer.
Figure 13B:
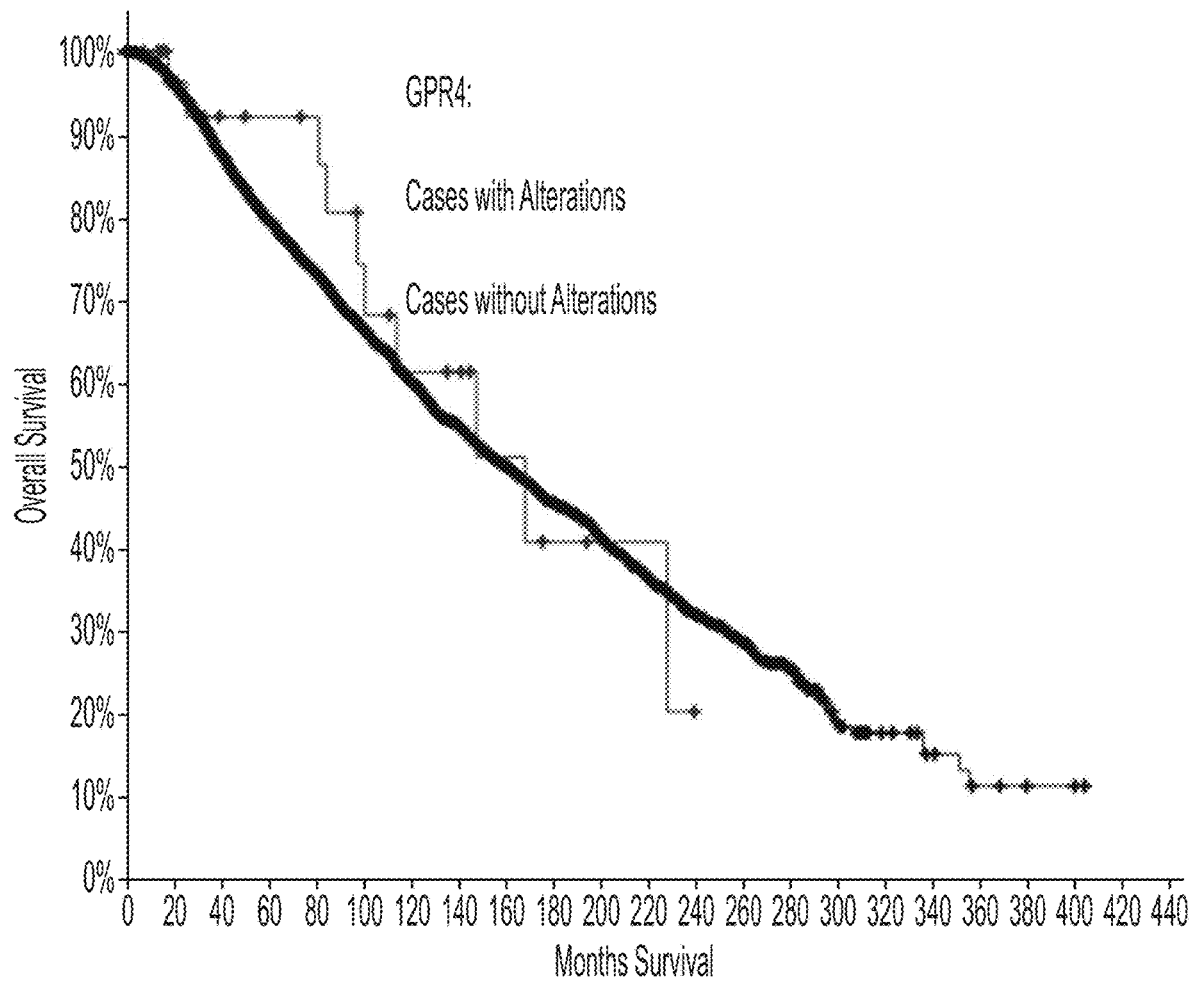
Figure 13C:
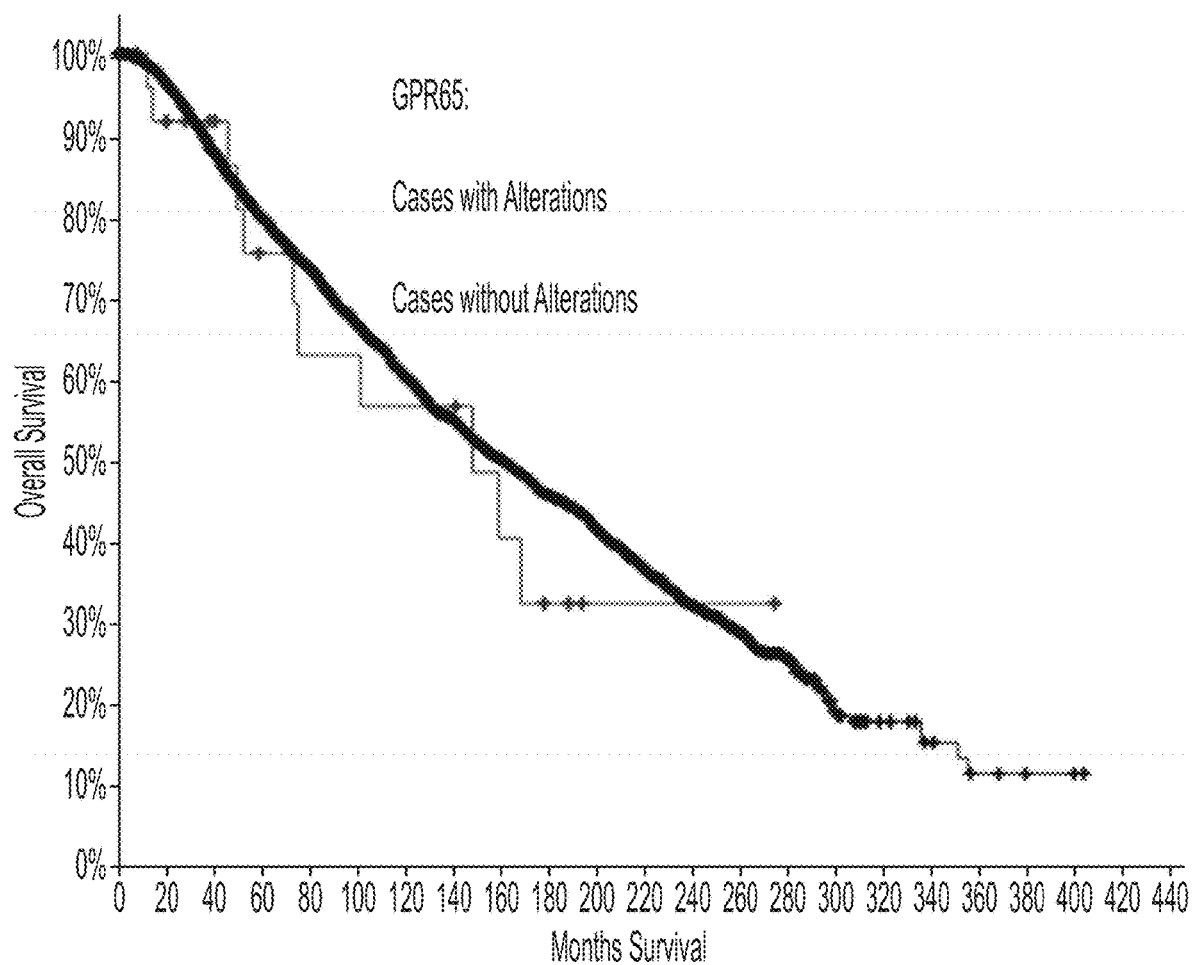

Finally, given the association of rs61745752 with cancer (FIG. 9), we investigated mutational burden and survival in the cBioPortal cohort. To ascertain if GPR68 and its variant could modulate metastatic potential in breast cancer in vitro we utilized spheroid integrity and invasion assay as described in Gayan et al., 2017 and Jung et al., 2019. MCF7 cells transfected with GFP, GPR68-GFP, and 336X-GFP were seeded in Ultra low attachment plates to form spheroids. At 48 hours 1:4 geltrex matrix was added. The variant E336X-GFP expressing spheroids were less stable than those expressing the wildtype sequence of GPR68. Mutations in GPR68 correlated with poor prognosis in breast cancer. FIG. 13 provides Kaplan-Mier plots generated in cBioportal of Breast cancer cohort carrying alterations in GPR68 (p=0.013), alterations in GPR4 (p=0.785), and alterations in GPR65 (p=0.612). Breast cancer patients harboring mutations in GPR68 had worse overall survival than those without. By contrast, the closely related members of the proton-sensing GPCR family GPR4 and GPR65 did not have similar effects on overall survival. See also Table 8, Table 9, and Table 10, below.

TABLE 8

Breast Cancer Patients; alterations in GPR68.

|  | Number of Cases, Total | Number of Cases, Deceased | Median Months Survival |
|---|---|---|---|
| Cases with Alterations in GPR68 | 18 | 10 | 89.96 |
| Cases without Alterations in GPR68 | 6447 | 1879 | 161.7 |

TABLE 9

Breast Cancer Patients; alterations in GPR4.

|  | Number of Cases, Total | Number of Cases, Deceased | Median Months Survival |
|---|---|---|---|
| Cases with Alterations in GPR4 | 32 | 10 | 168.2 |
| Cases without Alterations in GPR4 | 6433 | 1879 | 160.3 |

TABLE 10

Breast Cancer Patients; alterations in GPR65.

|  | Number of Cases, Total | Number of Cases, Deceased | Median Months Survival |
|---|---|---|---|
| Cases with Alterations in GPR65 | 27 | 11 | 148.1 |
| Cases without Alterations in GPR65 | 6438 | 1878 | 160.4 |

Figure 14B:
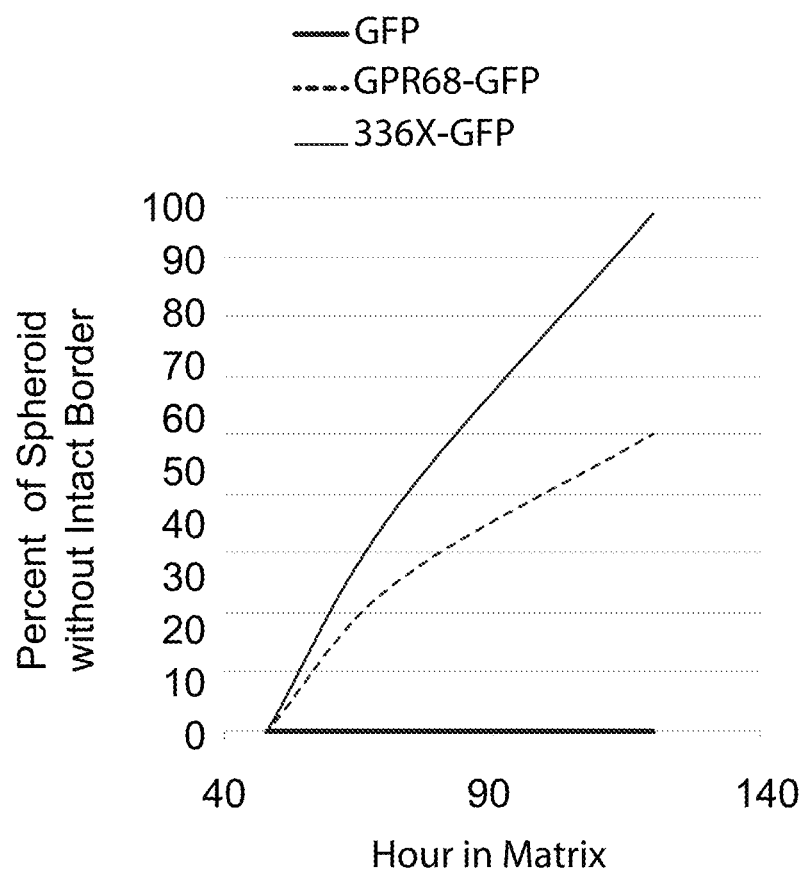

Transient transfection in MCF7 cells of GFP, GPR68-GFP, 336X-GFP revealed that, 3 days post matrix addition, the continuity of the outer ring of cells becomes disrupted by the inner core in GPR68-GFP and 336X-GFP transected spheroids. MCF7 cells transfected with GFP, GPR68-GFP, and 336X-GFP were seeded in Ultra low attachment plates to form spheroids. At 48 hours, 1:4 geltrex matrix was added. GFP transfected spheroids have the typical structure of outer proliferative ring with an inner quiescent core GPR68-GFP and 336X-GFP expressing spheroids have an irregular structure with the outer proliferative ring no longer intact on day 3. See FIG. 14A. On day 5 GPR68-GFP and 336X-GFP spheroids show outgrowths from where the outer ring is not intact. The cells of the inner core then extrude out into the matrix increasingly over 5-7 days post matrix addition. See FIG. 14A.

Figure 14C:
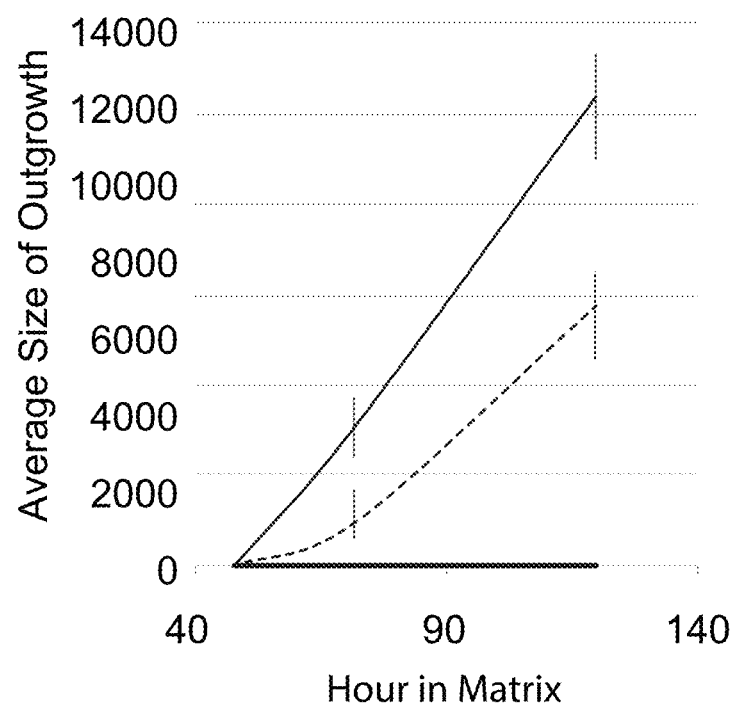
Figure 14D:
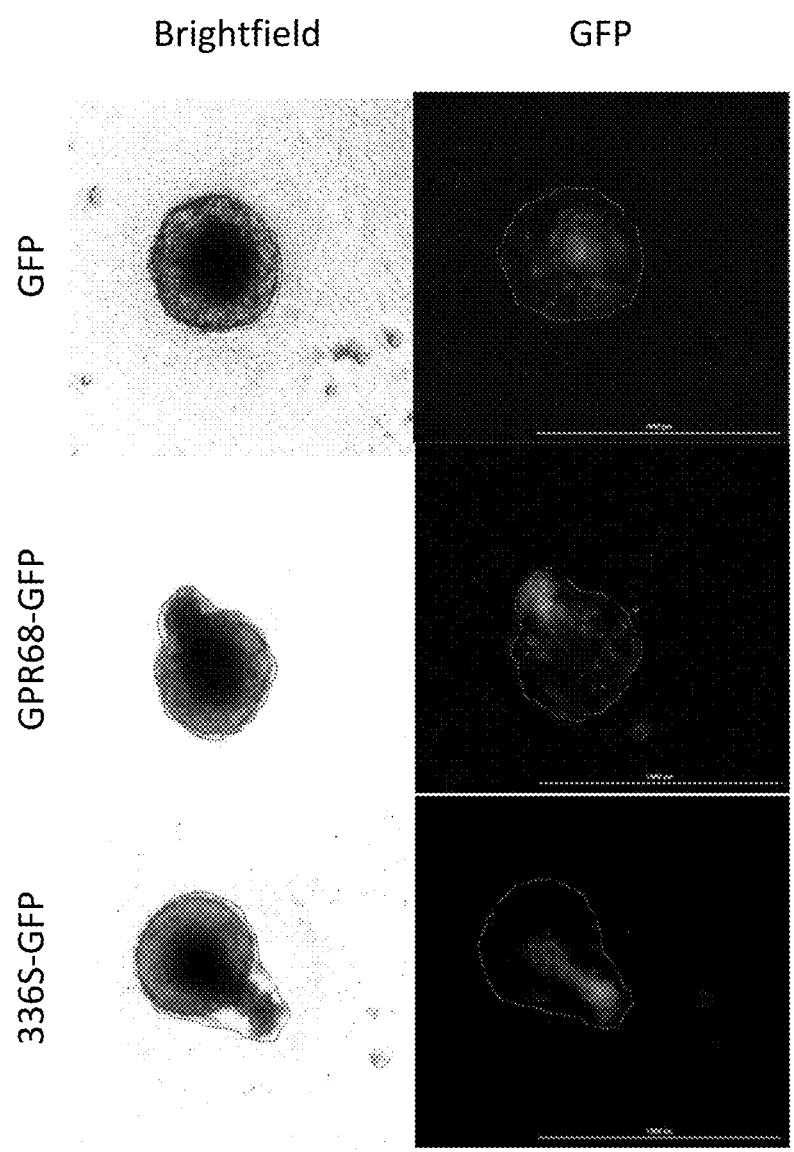

Furthermore, the degree of invasion in the 336X-GFP spheroids was greater than that of GPR68-GFP. See FIG. 14B and FIG. 14C, which show quantitation of the number of spheroids without intact outer rings (n=8) and quantitation of the size of the outgrowth from spheroids, respectively. Notably, the invasive cells from the inner core were primarily GFP+. See also FIG. 14D, which FIG. 14D presents an image of GFP+ cells in spheroids, revealing that GFP+ cells are the primary component of the spheroid outgrowths. Taken together, these data suggest that GPR68 and its variant rs61745752 are sufficient to induce a more invasive phenotype in noninvasive breast cancer MCF7 cells.

Example 12: Matrix Invasion in U87 Glioblastoma Spheroids

Figure 15A:
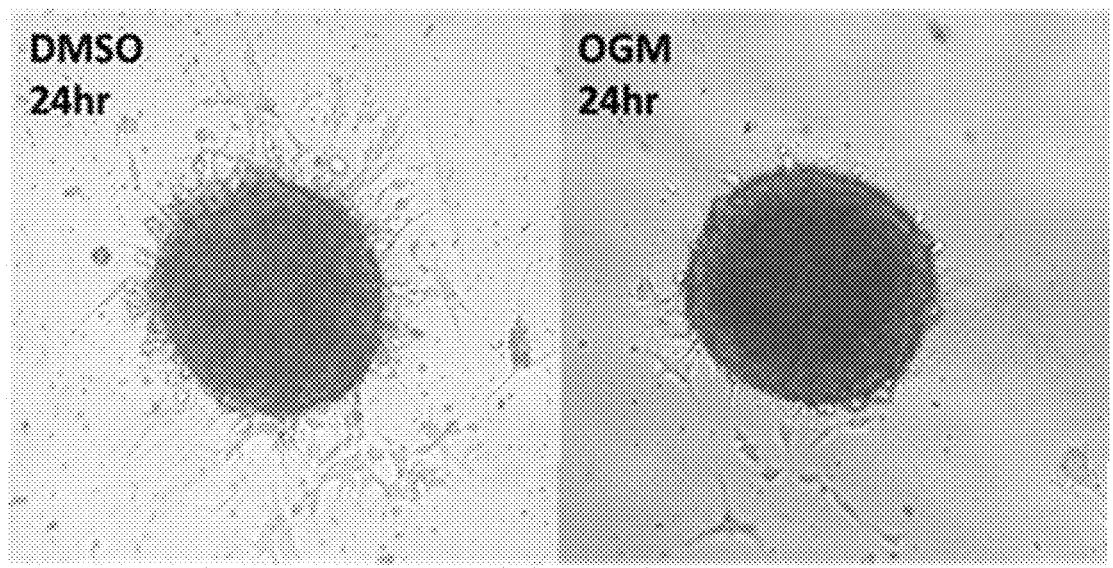
FIG. 15A and FIG. 15B. Relative matrix invasion of U87 (glioblastoma) cells in Matrigel™.
Figure 15B:
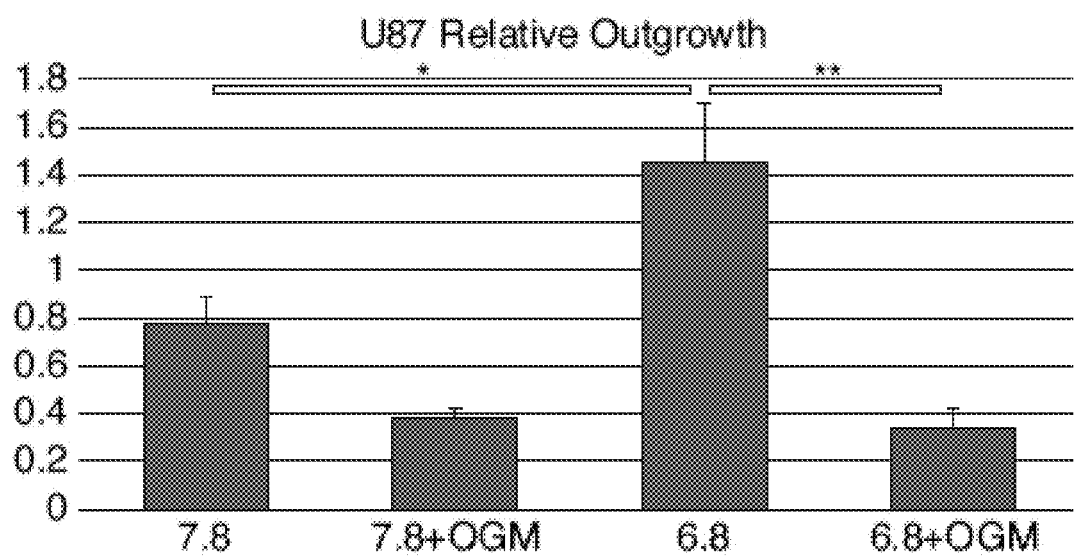

U87 glioblastoma spheroids were formed in low attachment round bottom plates for 3 days. Spheroids were then covered in Matrigel™, which was allowed to polymerize before treatment with acidified media with or without OGM2. Acidification increased the degree of matrix invasion which is attenuated by OGM2. See FIG. 15.

Figure 17A:
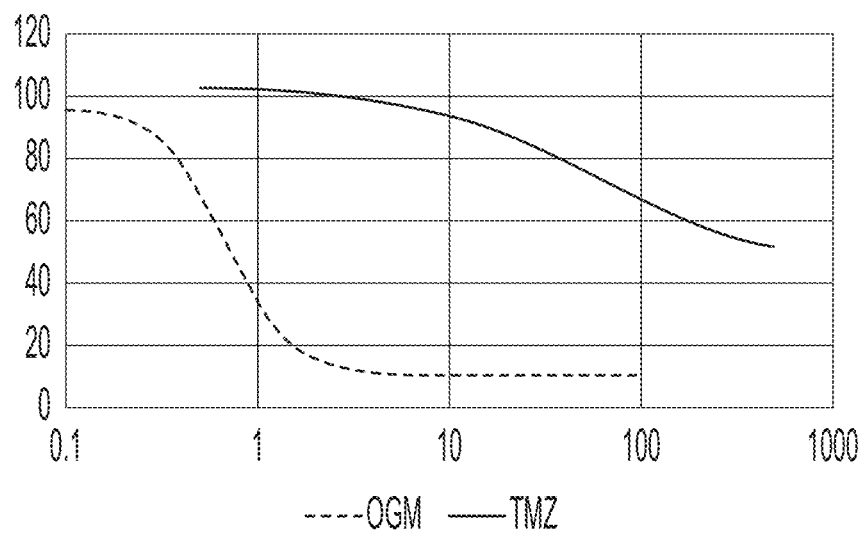
FIG. 17A and FIG. 17B. GPR68 inhibition of Glioblastoma growth in monolayer culture.
Figure 17B:
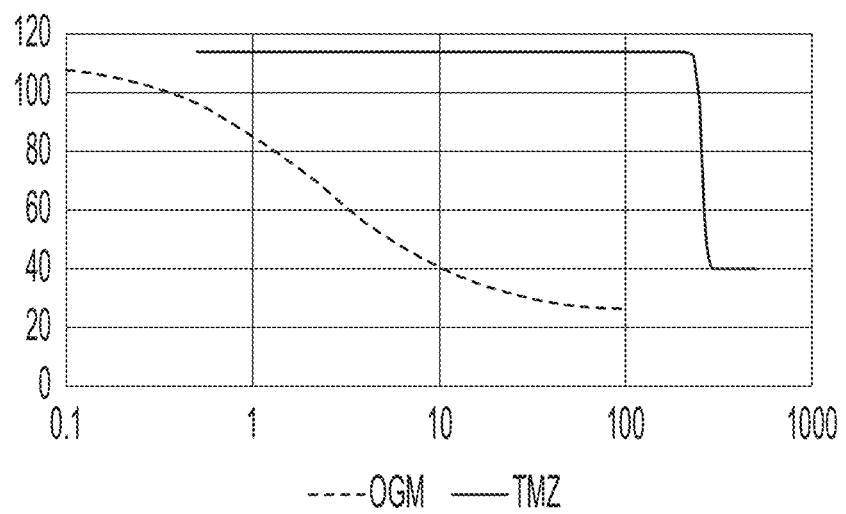

Example 13: GPR68 Inhibition Attenuates Growth in 2D Cell Culture in Both TMZ Sensitive (U87) and Insensitive (U138) Glioblastoma Models Temozolomide is the standard of care for glioblastoma but only works on 30% of patients. Temozolomide sensitive U87 (FIG. 17A) and Temozolomide insensitive U138 (FIG. 17B) glioblastoma cell lines were plated in 96-well plates and exposed to increasing doses of either Temozolomide or OGM2. The viability of cells was assayed using cell titer blue after 72 hours, and data was normalized to DMSO vehicle control. See results in FIG. 17. OGM was more effective than Temozolomide in this test.

Figure 18A:
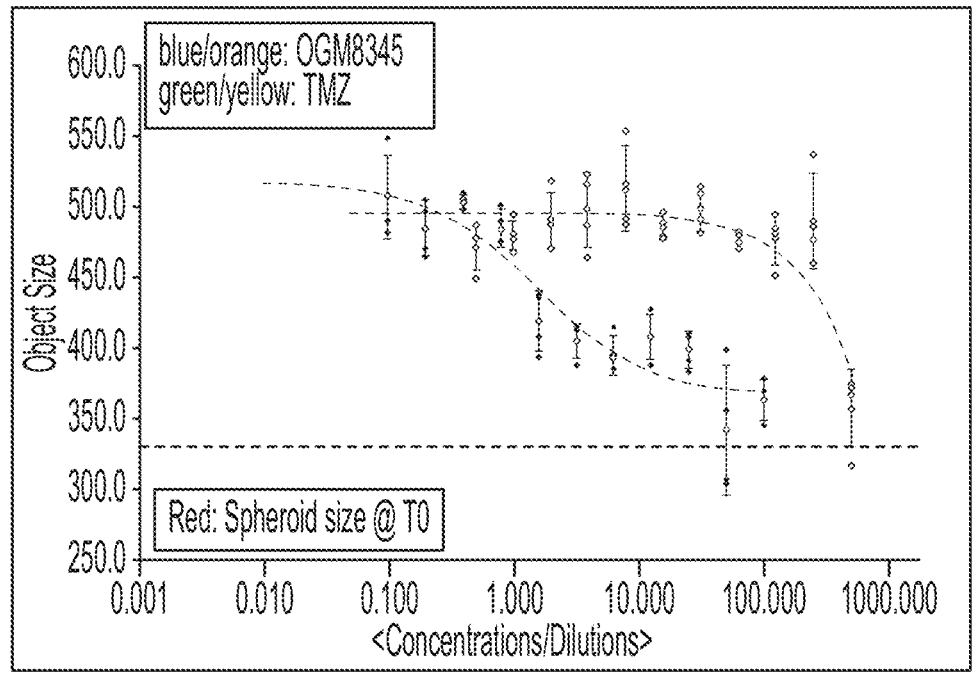
FIG. 18A and FIG. 18B. GPR68 inhibition of Glioblastoma growth in spheroid culture.
Figure 18B:
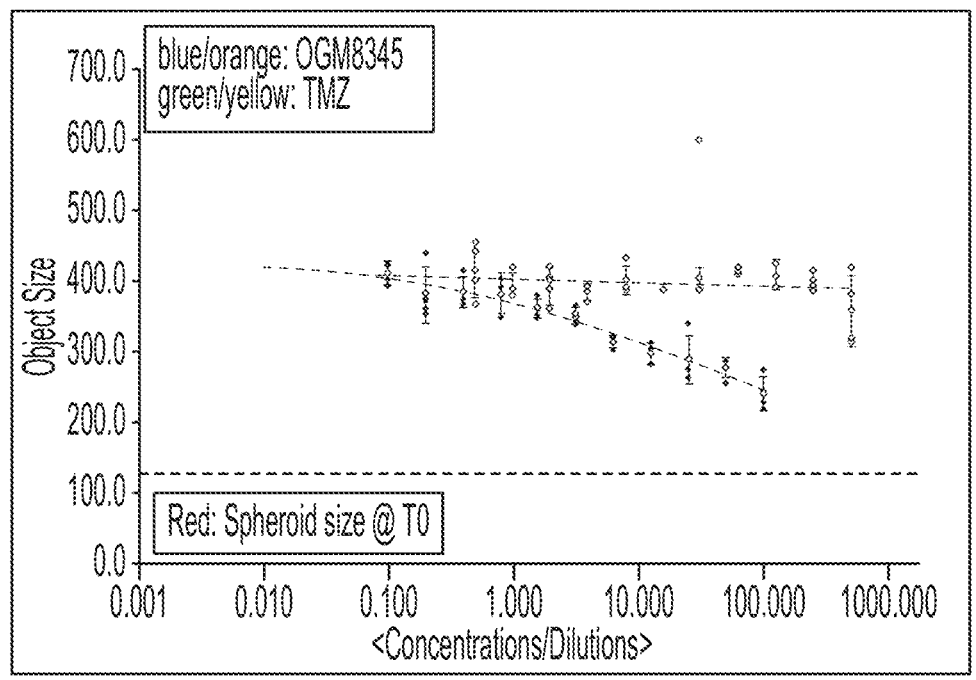

Example 14: GPR68 Inhibition Attenuates Growth in 3D Tumoroid Culture in Both TMZ Sensitive (U87) and Insensitive (U138) Glioblastoma Models Tumor spheroid cultures are a more physiological model of tumor growth than typical 2D cell culture. Temozolomide sensitive U87 (FIG. 18A) and Temozolomide insensitive U138 (FIG. 18B) glioblastoma cell lines were plated in low attachment round bottom 96-well plates and allowed to form tumor spheroids for 3 days (T0). At T0, spheroids were imaged using Lionheart™ (HCS) High-Content Imaging Systems (Biotek™) and then were exposed to increasing doses of either Temozolomide or OGM2. After 5 days of treatment the spheroids were imaged again (T5). The size (area) of the spheroids after 5 days of treatment was quantified, and the average size of the spheroids at T0 is depicted in red. OGM was more effective than Temozolomide in this test. See FIG. 18.

Figure 19A:
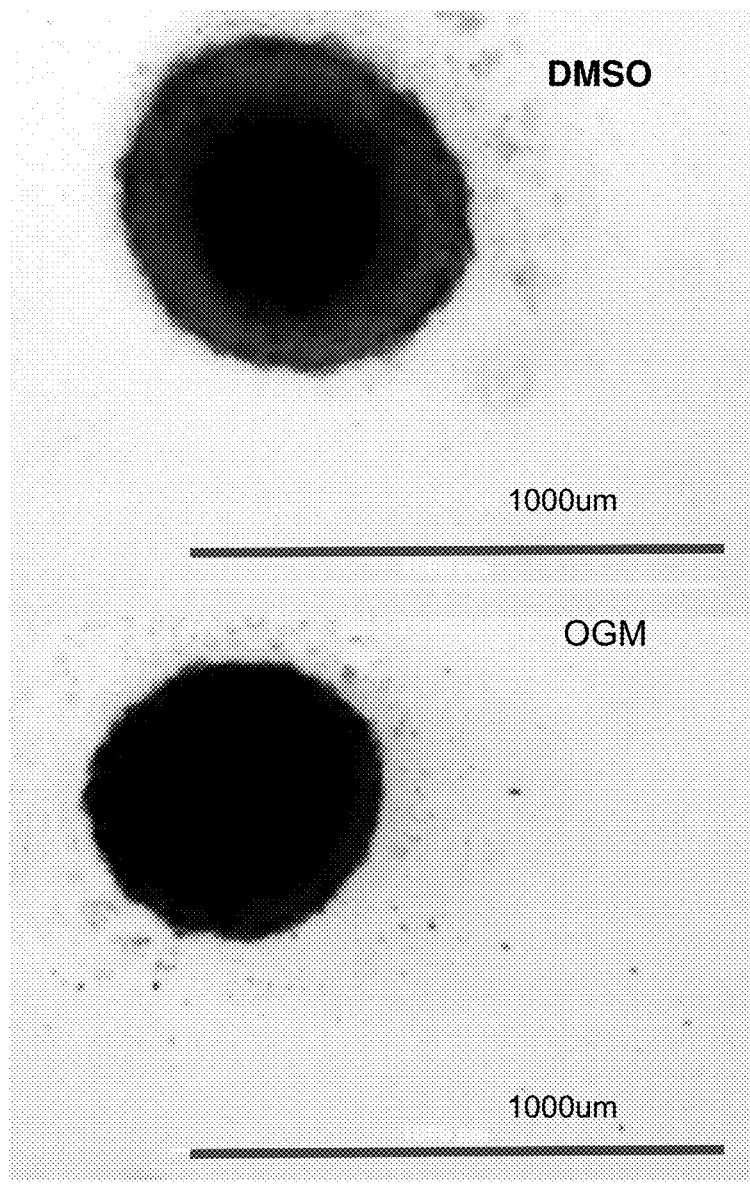
FIG. 19A and FIG. 19B. Ogerin GPR68 Positive Allosteric Modulator (PAM).
Figure 19B:
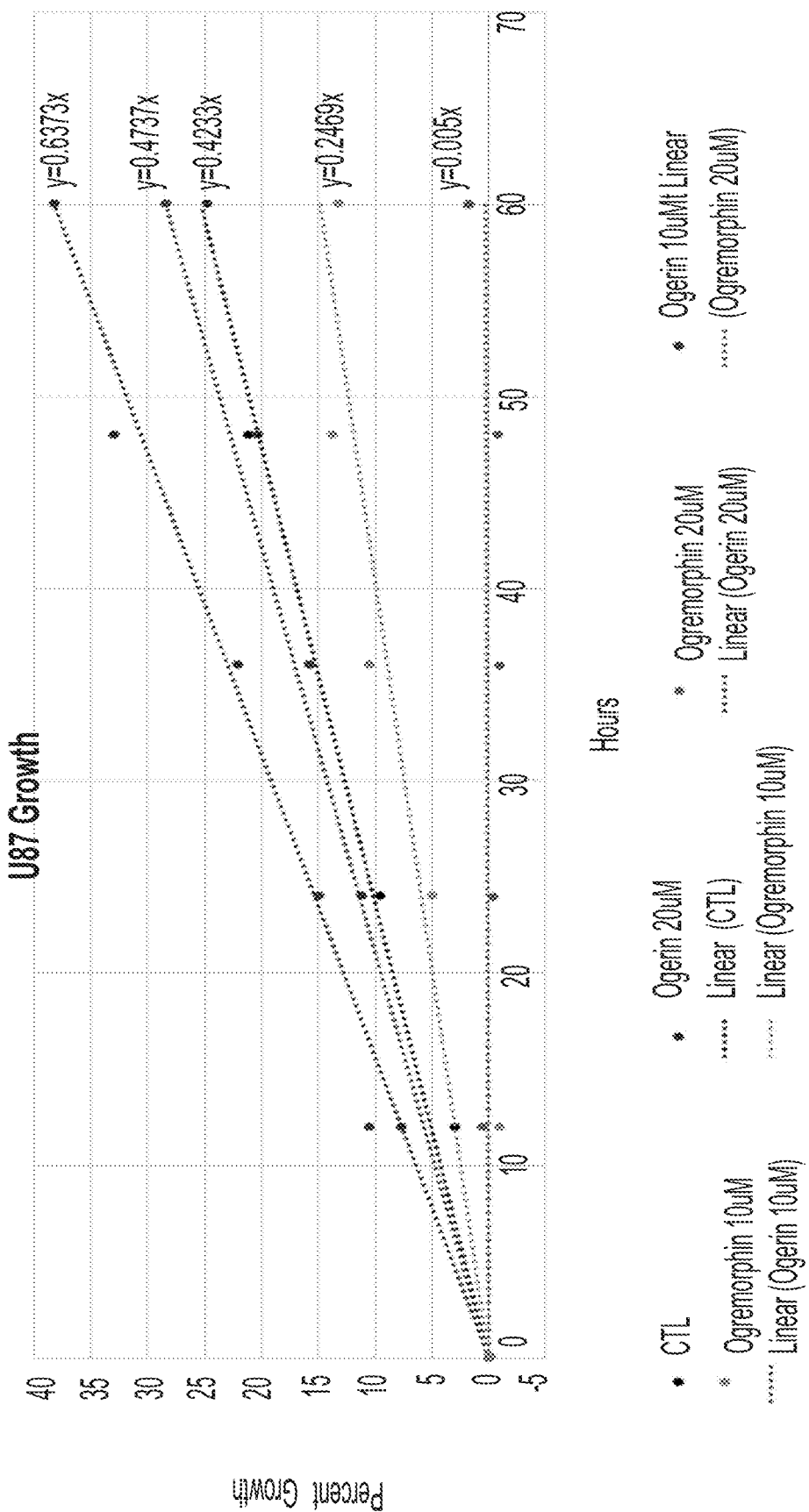

Example 15: Ogerin GPR68 Positive Allosteric Modulator (PAM) Stimulates Growth in 3D Tumoroid Culture in Glioblastoma Models A GPR68-positive allosteric modulator, Ogerin, was tested. U87glioblastoma cells were plated in low attachment round bottom 96-well plates and allowed to form tumor spheroids for 3 days (T0). These spheroids were treated with Vehicle (DMSO), 10 µM/20 µM Ogerin or 10 µM/20 µM Ogremorphin (OGM2). The spheroids were placed in the Lionheart™ HCS equipped with environmental control (5% $CO_2$ at 37° C.) and imaged every 12 hours. See FIG. 19A and FIG. 19B.

Example 16: GPR68 Inhibition Increases Cell Death 2D and 3D tumor spheroid assays were carried out as described herein with U87 cells using 10 µM OGM2 and stained with ReadyProbes™ Cell Viability Imaging Kit, Blue/Green (Thermo™). All cell nuclei labeled in blue, only nuclei with disrupted cell membranes are stained green, indicating cell death. See FIG. 20A and FIG. 20B.

Example 17: OGM Inhibition of Tumoroid Growth is pH Dependent

Figure 21B:
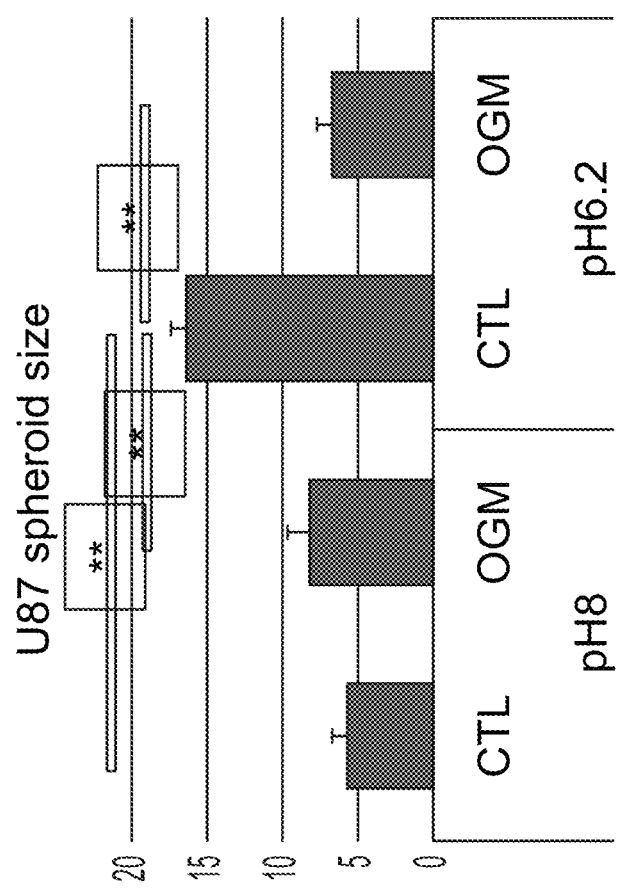
FIG. 21A and FIG. 21B. pH dependent OGM inhibition of tumoroid growth.
Figure 21A:
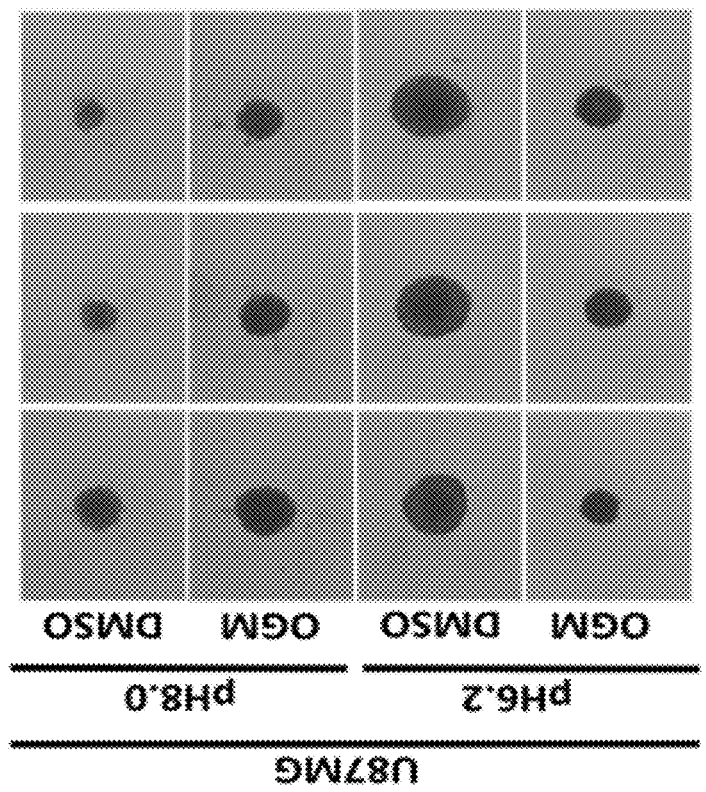

Spheroids were formed over 3 days using low attachment 96-well round bottom plates and then treated with DMSO or OGM2 in either pH 8 buffered media or pH 6.2 buffered media and grown for 3 days. The size (area) of spheroids was measured in relative area units. Spheroids grown in pH 6.2 were significantly larger than those grown at pH 8. Thus, GPR68 is inactive at pH 8 and is active at pH 6.2. This increase in growth was abrogated by OGM2. See FIG. 21.

Example 18: OGM Reduces Clonogenicity of U87 Glioblastoma Cells

Figure 22:
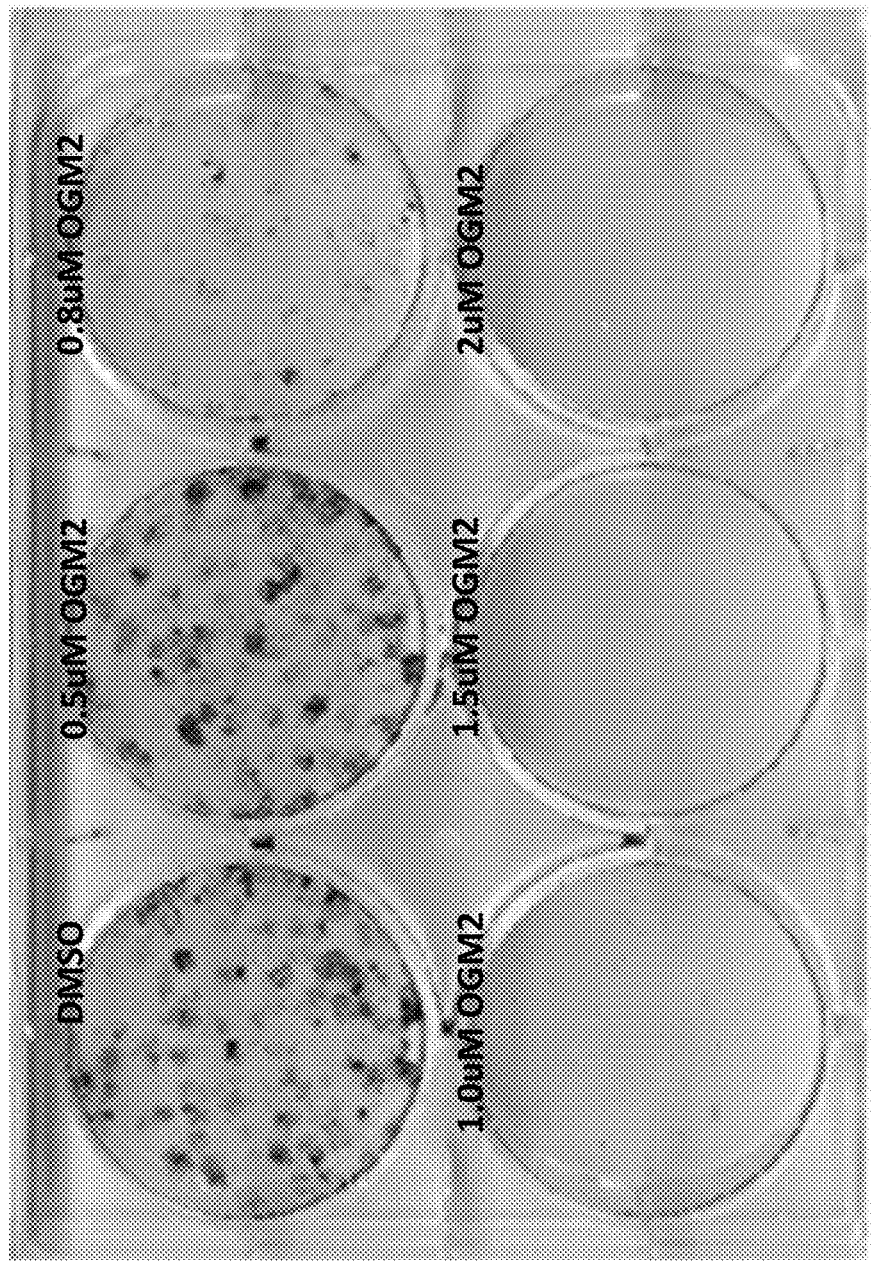
FIG. 22. OGM reduces clonogenicity of U87 glioblastoma cells.

U87 cells were plated at 400 cells per well in a 6-well plate and on the next day were treated with increasing concentrations of OGM2 for 12 days. The doses were 0 uM (DMSO control) 0.1 μM 0.5 uM, 1 uM, 1.5 uM and 2 uM, as labelled. The plate was fixed with formalin and stained with crystal violet. See FIG. 22.

Example 19: HCT116 Colon Cancer Effects

Figure 23:
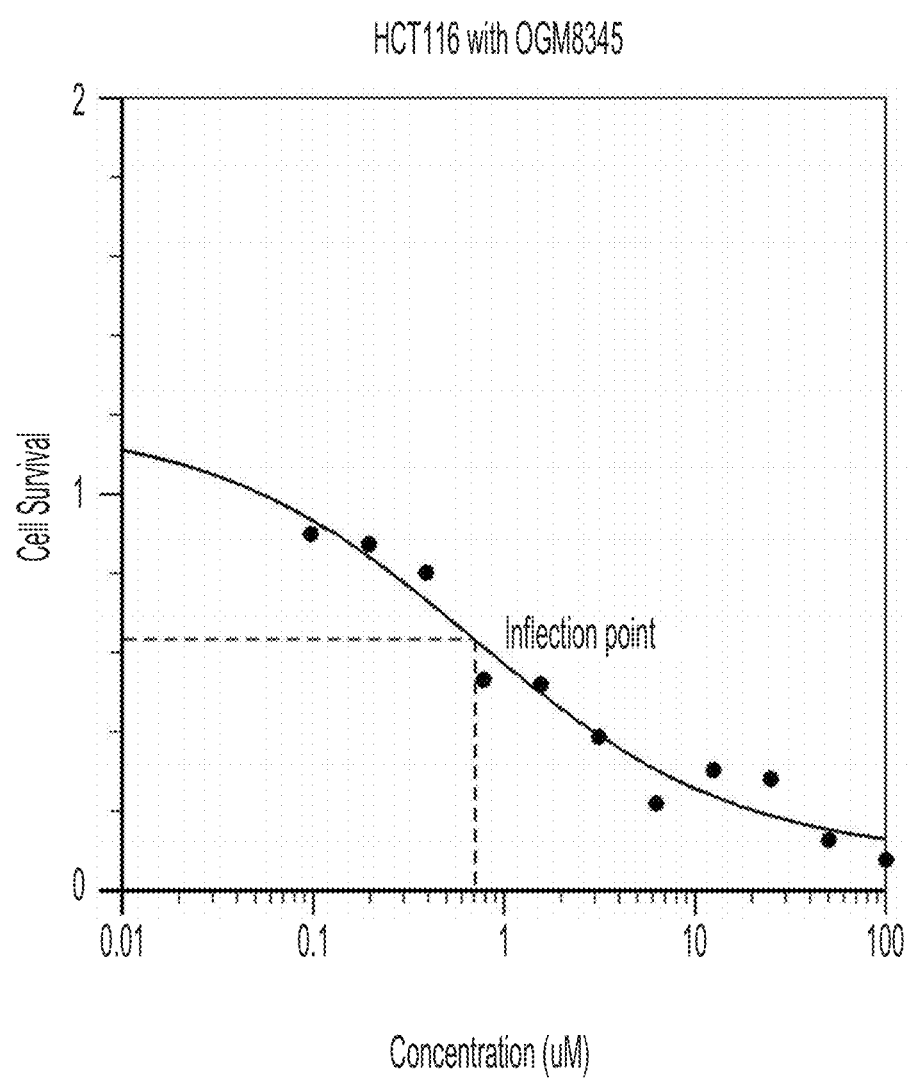
FIG. 23. HCT116 colon cancer treatment.

HCT116 colon cancer cells were treated with OGM2 at different concentrations for 48 hours. Cell viability was assessed using Cell titre blue. The results are shown in FIG. 23.

Example 20: Effects on Pancreatic Cancer

Figure 24A:
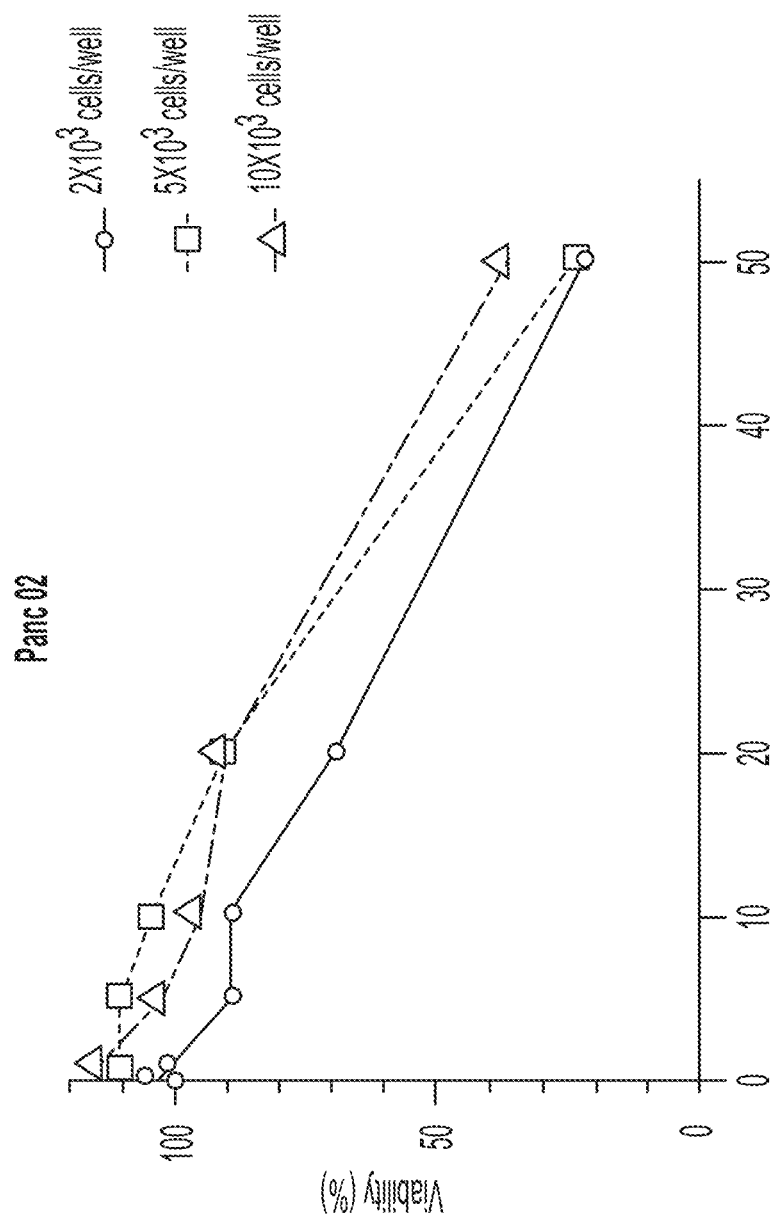
FIG. 24A through FIG. 24C. Studies of PAN02 pancreatic cancer cells.

PANC02 pancreatic cells were plated at different concentrations of cell per well in a 96-well plate. On the following day, cells were treated with increasing doses of OGM2. Twenty-four hours later, the cell viability was assayed with crystal violet and normalized to untreated cells. See FIG. 24A.

Figure 24B:
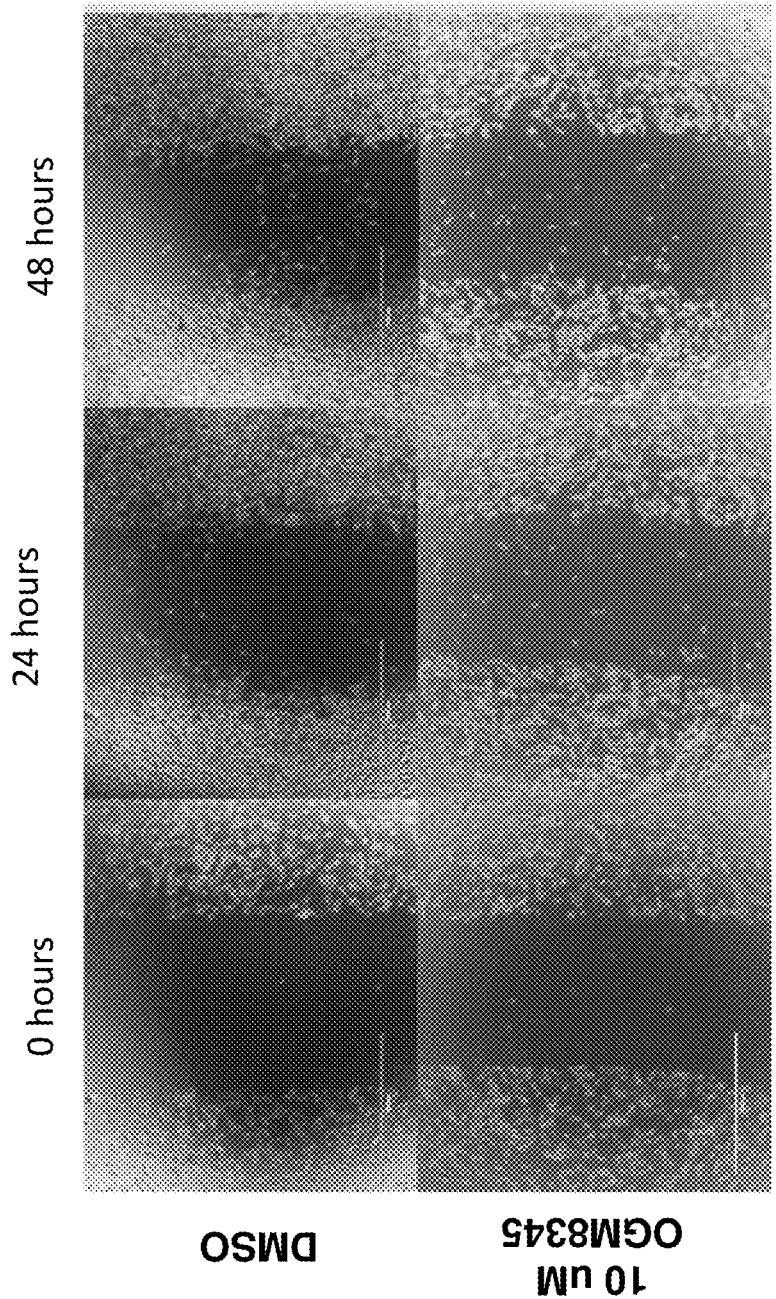

In a second study, PANC02 pancreatic cells plated and grown to confluence. Using a P200 tip, cells were denuded and allowed to migrate for 24 hours in DMSO or 10 μM OGM2 and imaged. OGM-treated wells had significantly reduced migration. See FIG. 24B.

Figure 24C:
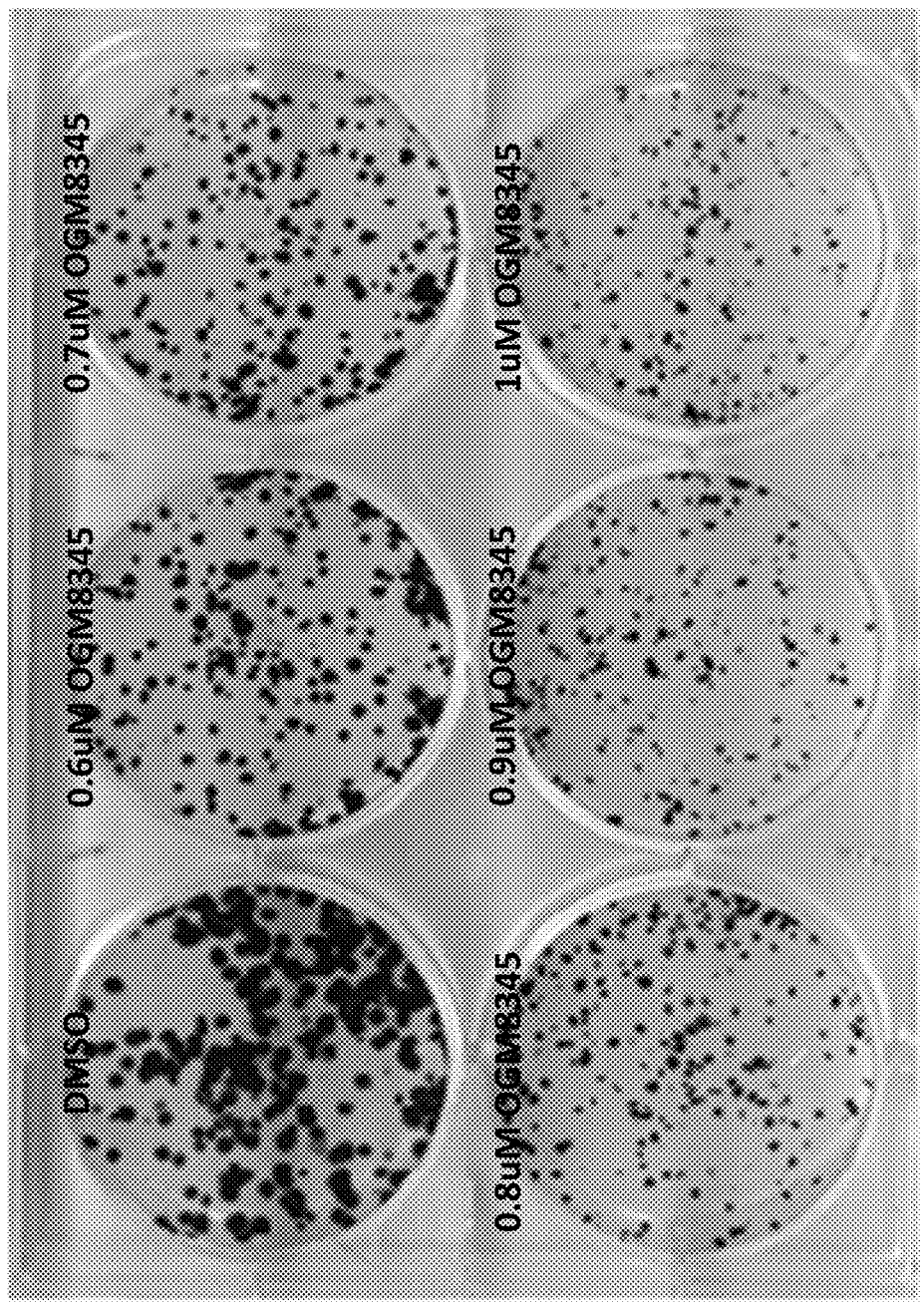

In a third study, PANC02 pancreatic cells were plated at 400 cells per well in a 6-well plate and on the next day were treated with increasing concentrations of OGM2 for 7 days. The plate was fixed with formalin and stained with crystal violet. The results are shown in FIG. 24C for the indicated concentrations of OGM2, and demonstrate that OGM2 treated well reduced the clonogenicity of pancreatic cancer cells.

Example 21: Effects on Lung Cancer

Figure 25A:
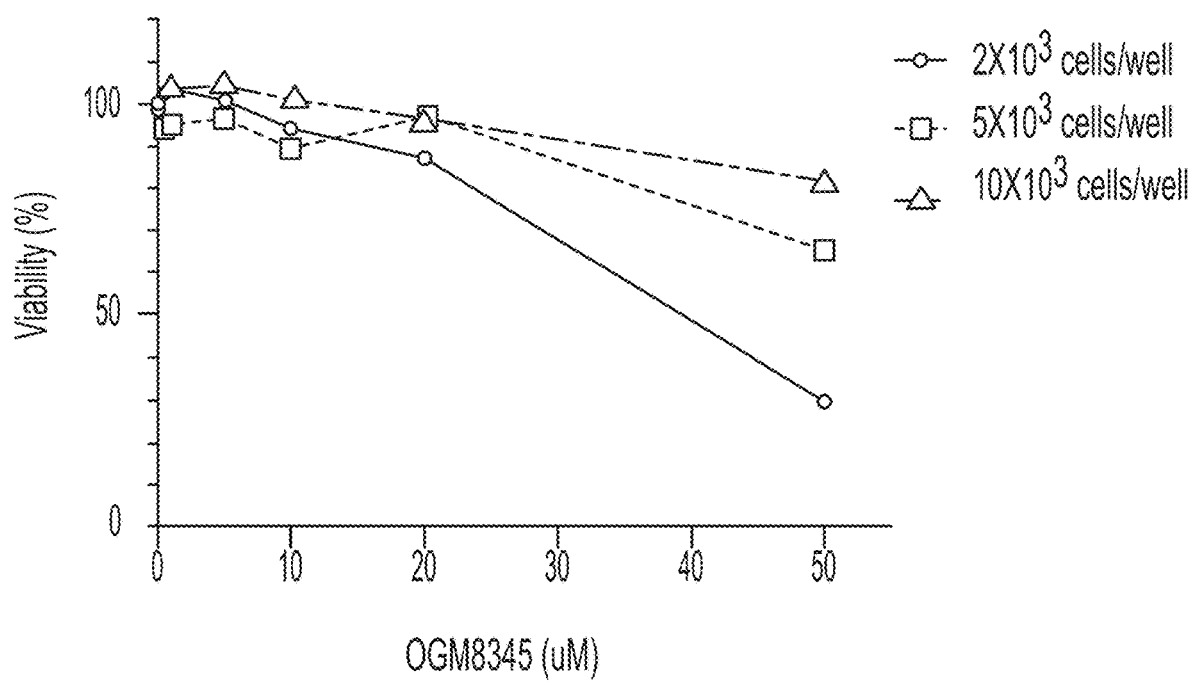
FIG. 25A and FIG. 25B. Studies of A549 lung cancer cells.

A549 lung cancer cells were plated at different concentrations of cell per well in a 96-well plate. On the following day cells were treated with increasing doses of OGM2. Twenty-four hours later cells viability was assayed with crystal violet and normalized to untreated. See FIG. 25A. These data show that relatively High doses of OGM2 are necessary for toxicity in A549 cells.

Figure 25B:
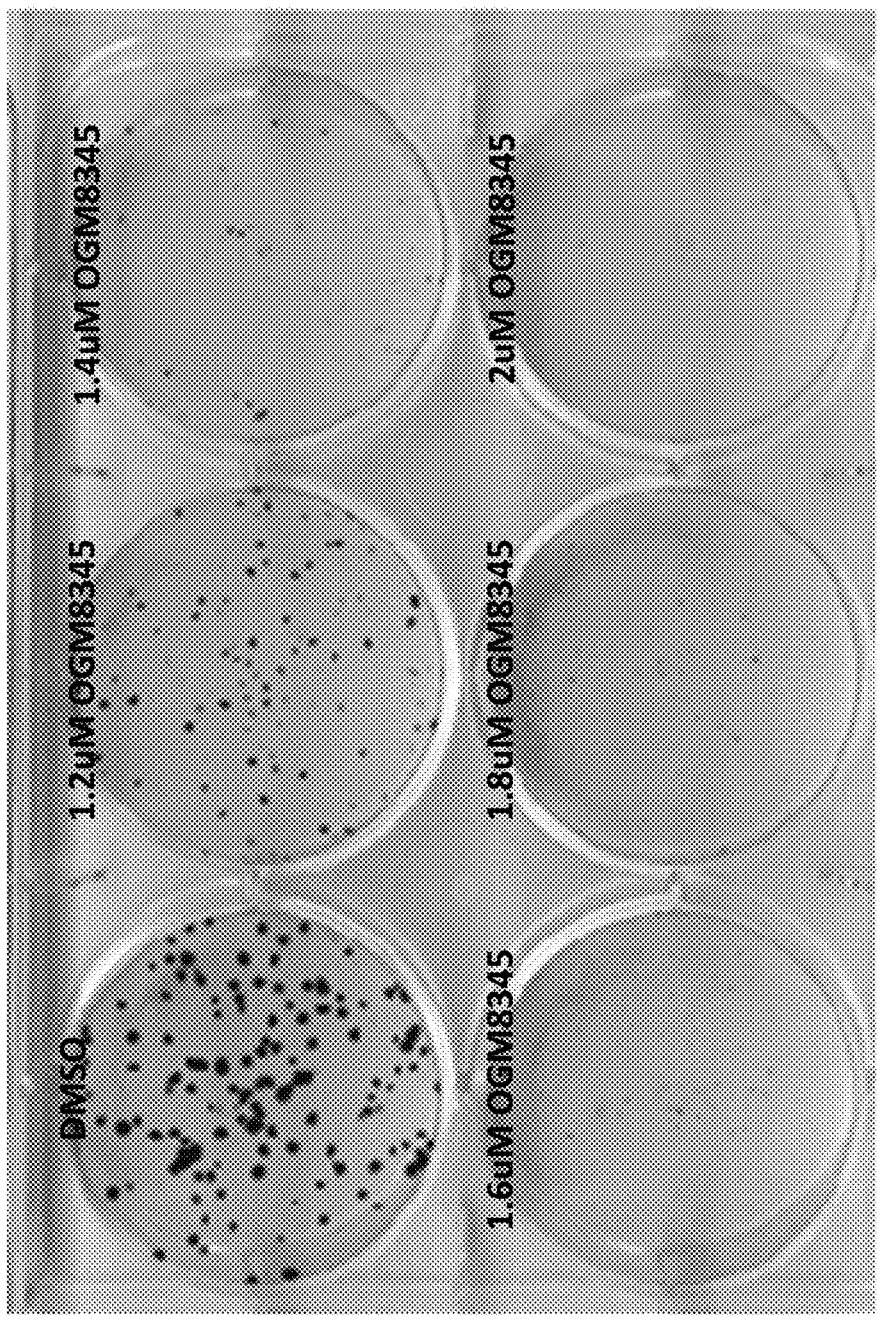

A549 lung cancer cells were plated at 300 cells per well in a 6-well plate and on the next day were treated with increasing concentrations of OGM2 for 8 days. The plate was fixed with formalin and stained with crystal violet. See FIG. 25B for results at the indicated concentrations. The results are shown in FIG. 25C for the indicated concentrations of OGM2, and demonstrate that OGM2 treated well reduced the clonogenicity of lung cancer cells.

Figure 26A:
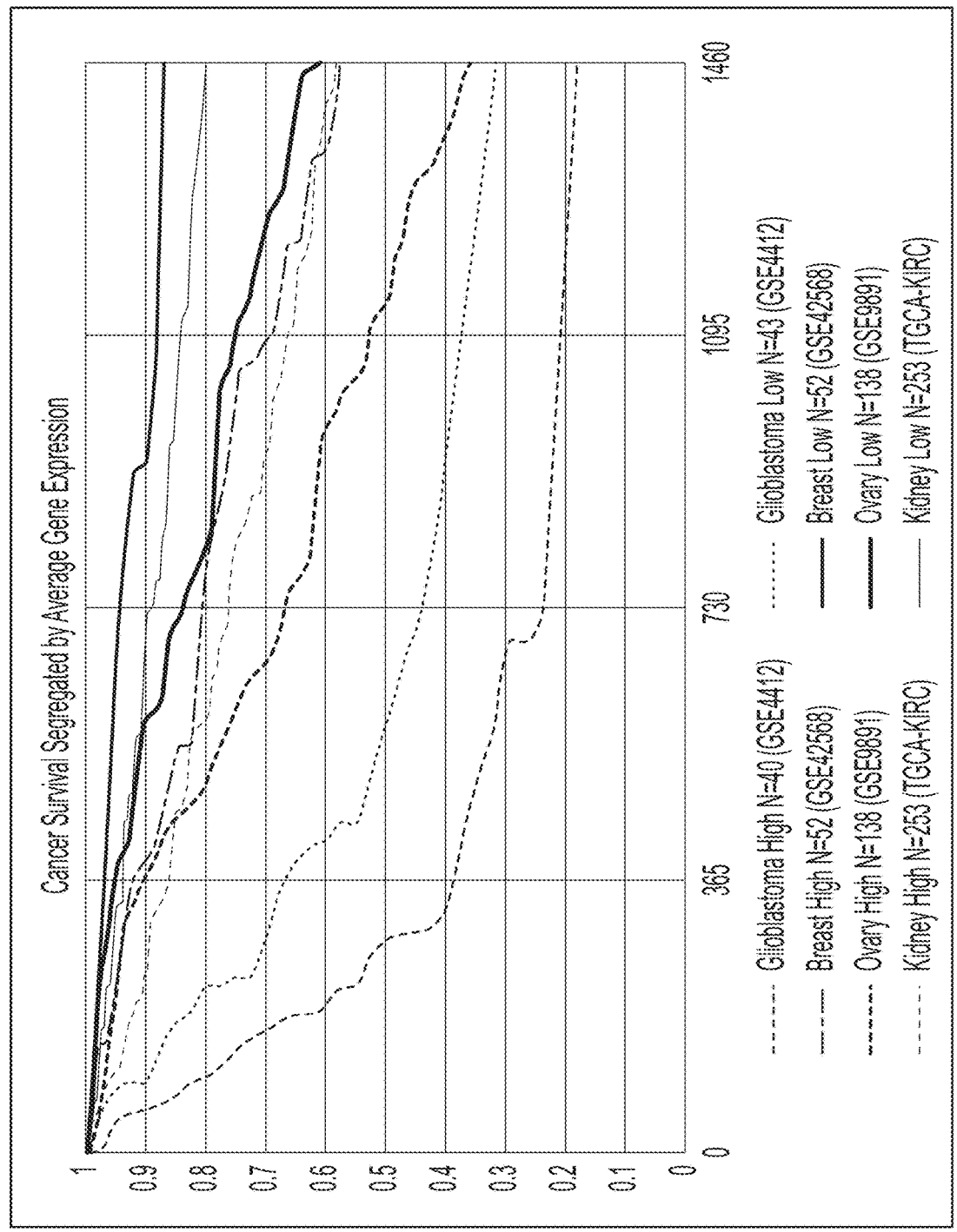
FIG. 26A and FIG. 26B. Viability of cancer cells.
Figure 26B:
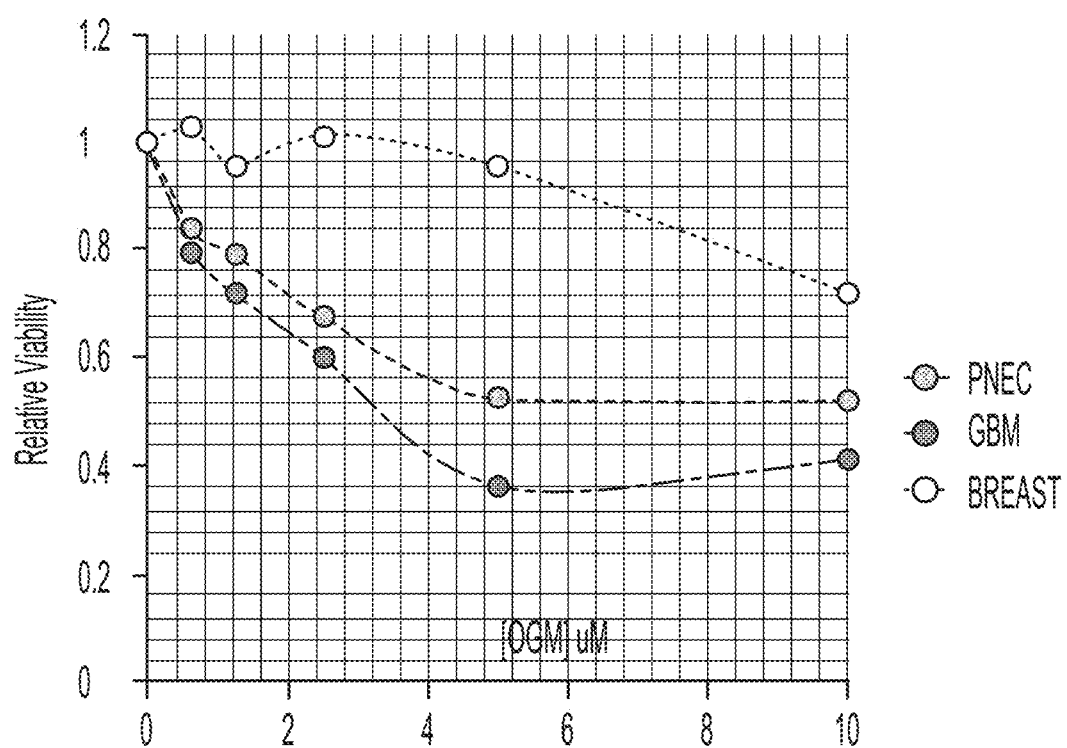

Example 22: Lower GPR68 Expression Correlates to Better Prognosis of Multiple Cancer Cell Types. OGM2 Reduces Viability of Prostate and Breast Cancer Cells Multiple studies were conducted as discussed herein, but with different cancer type cohorts. Data was extracted from Gene expression omnibus using ProggeneV2. Briefly, probes were prepared using standard Affymetrix™ protocols, and hybridized to Affymetrix™ HG-U133A and HG-U133B arrays. The cohort was separated by High and low expression of GPR68 by above or below the median expression level. Survival of the cohorts was plotted in FIG. 26A. Survival of multiple cancer types including breast (MDA MB231), glioblastoma (U87), and Prostatic Neuroendocrine cancer (PNEC: PC3) is shown in FIG. 26B. Cells were plated in 96-well plates and then treated with increasing doses OGM2. Seventy-two hours later, survival was assayed with cell titer blue. Each cell line was normalized to DMSO treated control. See FIG. 26.

Example 23: OGM Synergizes with TMZ and Radiation

Figure 27A:
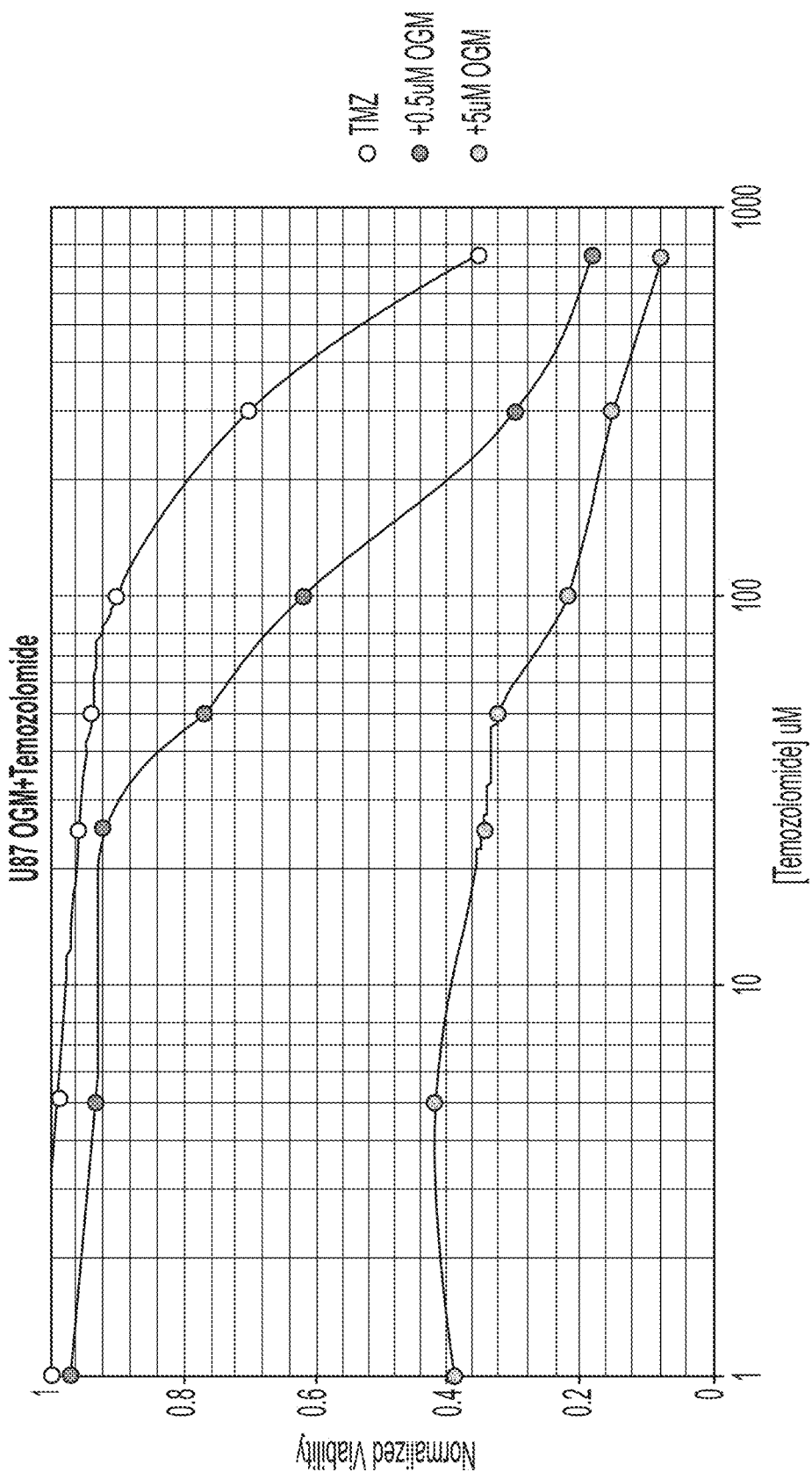
FIG. 27A and FIG. 27B. OGM synergizes with TMZ and radiation.

U87 cells were treated with increasing concentrations of temozolomide (TMZ) without OGM2 or with 0.5 μM or 5 μM OGM2. See results in FIG. 27A, showing a synergistic result for cell viability.

Figure 27B:
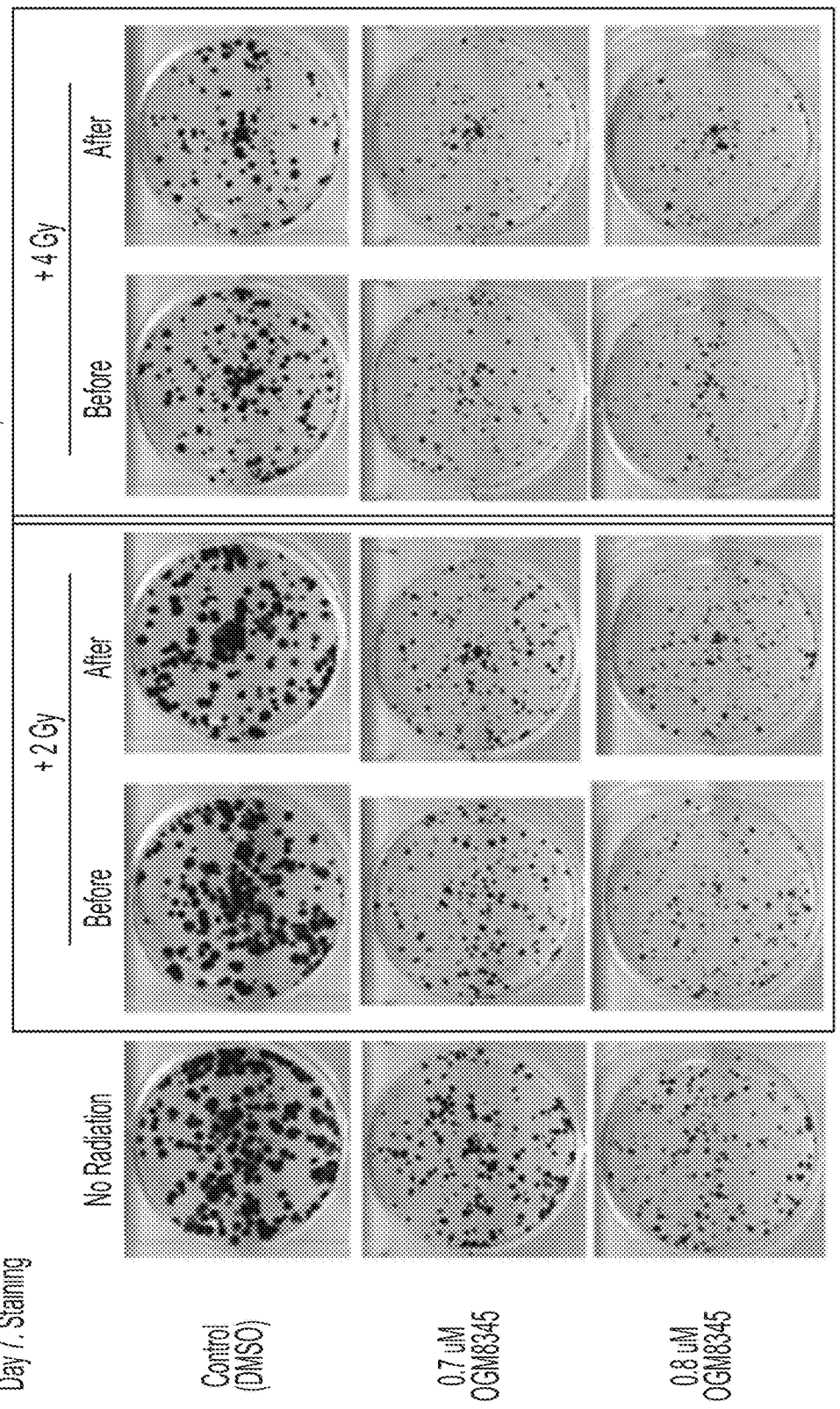

In a second study, four hundred PANC02 cells were plated per well in 6-well plates. The next day, cells were irradiated with either 2y of 4y of radiation, and also treated either 100 minutes before or 100 minutes after radiation with 0.7 μM or 0.8 μM OGM2. The results are presented in FIG. 27B.

Example 24: OGM Inhibits Acid Induced Mucin Production

Figures 28A, 28B:
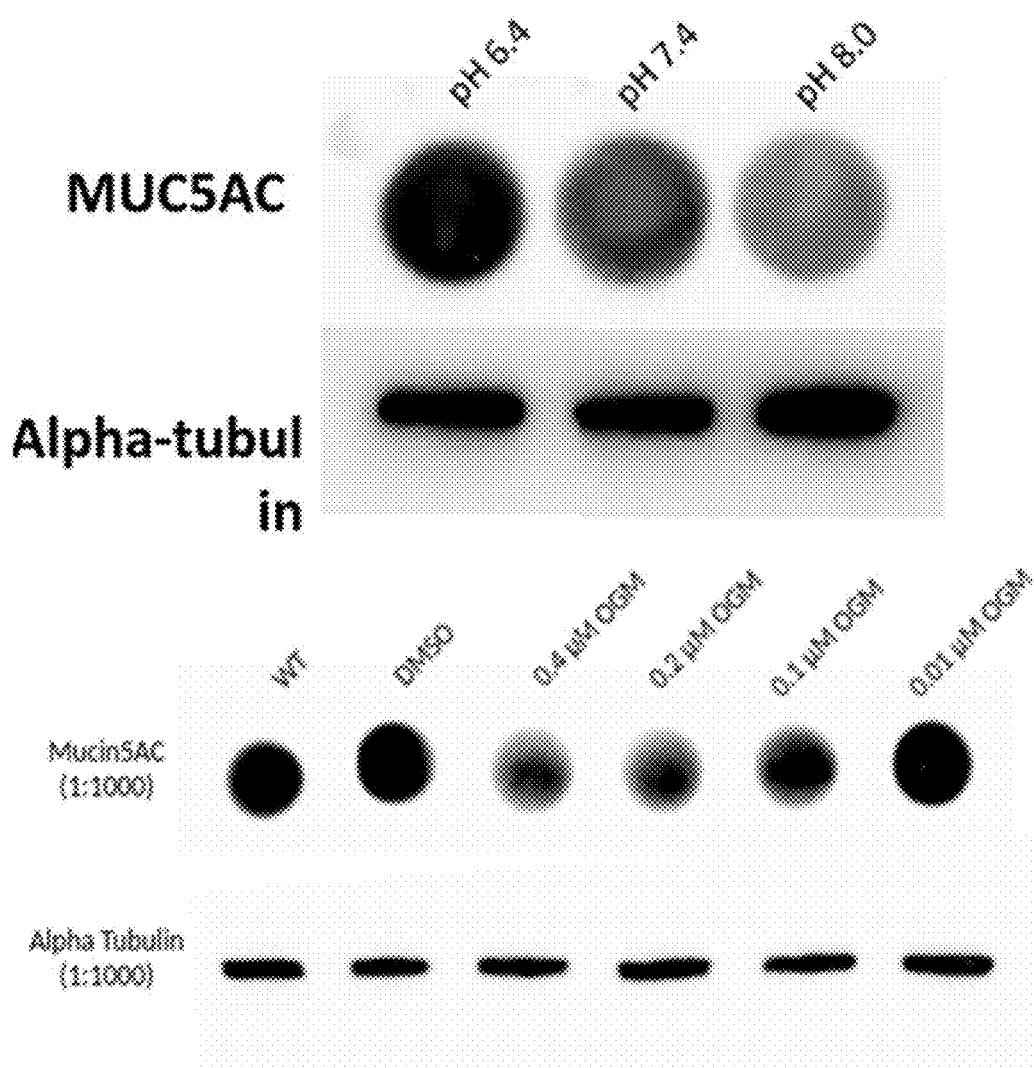

Lung (A549) cells were plated in 6-well plates. Cells were incubated in pH-buffered medium (at the pH indicated in FIG. 28A) for 24 hours. The cells then were rinsed and protein was isolated. Dot blots were made with anti Mucin-5AC antibodies, and an equivalent amount of protein was run on a western blot to detect alpha tubulin. See FIG. 28A. Lung (A549) cells were cultured as above, but in pH 6.4 buffered media with increasing concentrations of OGM834. Mucin5AC and alpha tubulin were detected in the same way. See FIG. 28B, which shows that inhibition of GPR68 inhibits Mucin 5AC in a dose-dependent manner.

Figure 28E:
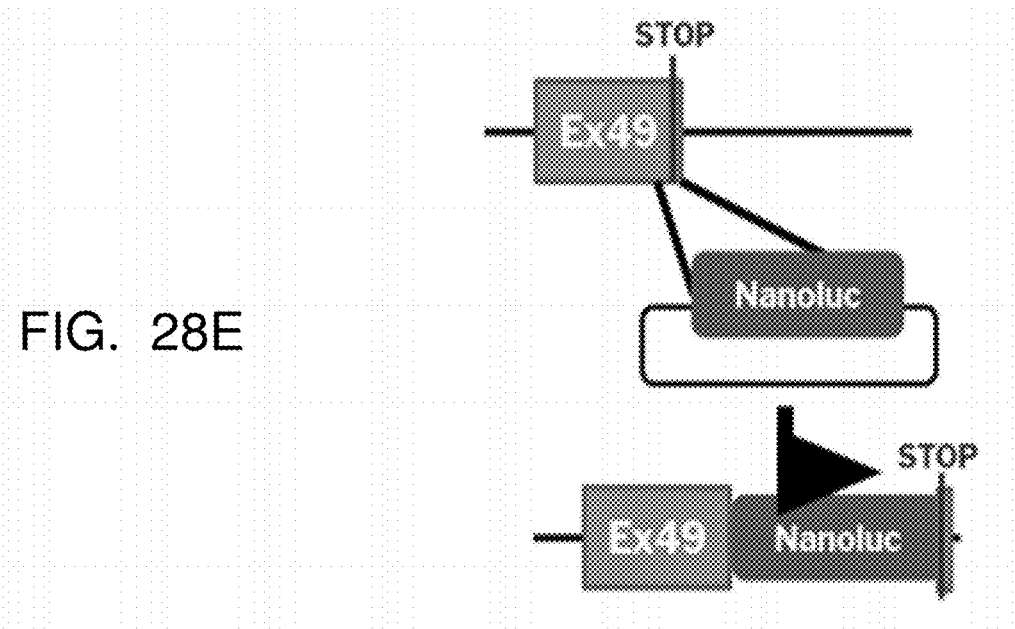
Figure 28F:
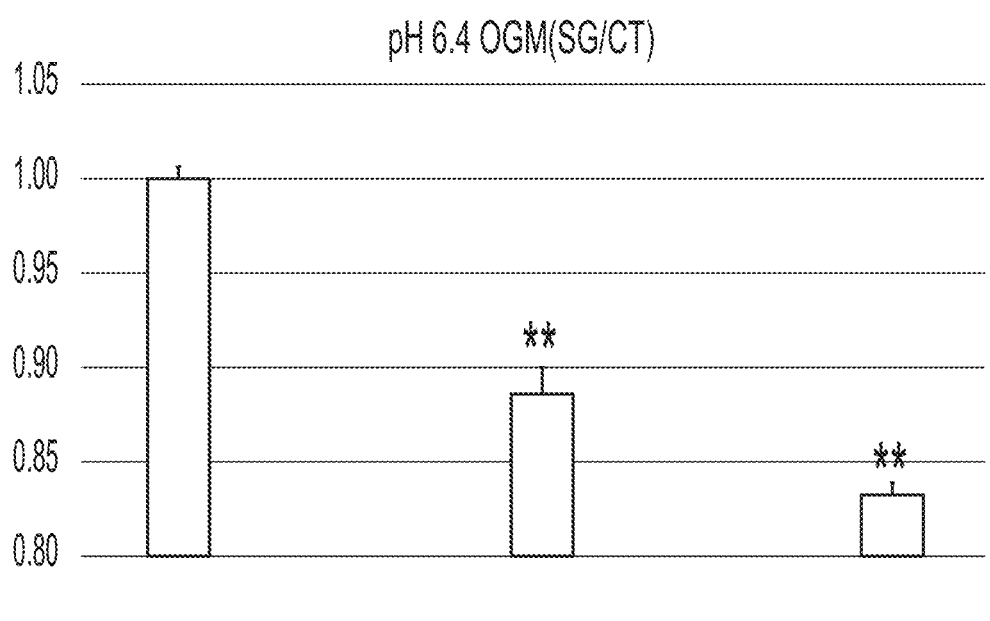

In addition, A549 cells were cultured in pH 6.4 medium with or without OGM2 for 24 hours cells were then rinsed and then stained with Periodic Acid Staining solution which detects mucins. See FIG. 28C and FIG. 28D. FIG. 28E is a schematic of cas9 mediated endogenous tagging of MU5AC genetic locus with nano-luciferase in A549 cells. For FIG. 28F, Muc5ac-Luc cells were cultured in pH 6.4 buffered medium with and without OGM2 for 24 hours. Cell lysates were then assayed for luciferase activity and normalized to untreated control. See results in FIG. 28G.

Example 25: Additional Pulmonary Indications

Figure 29:
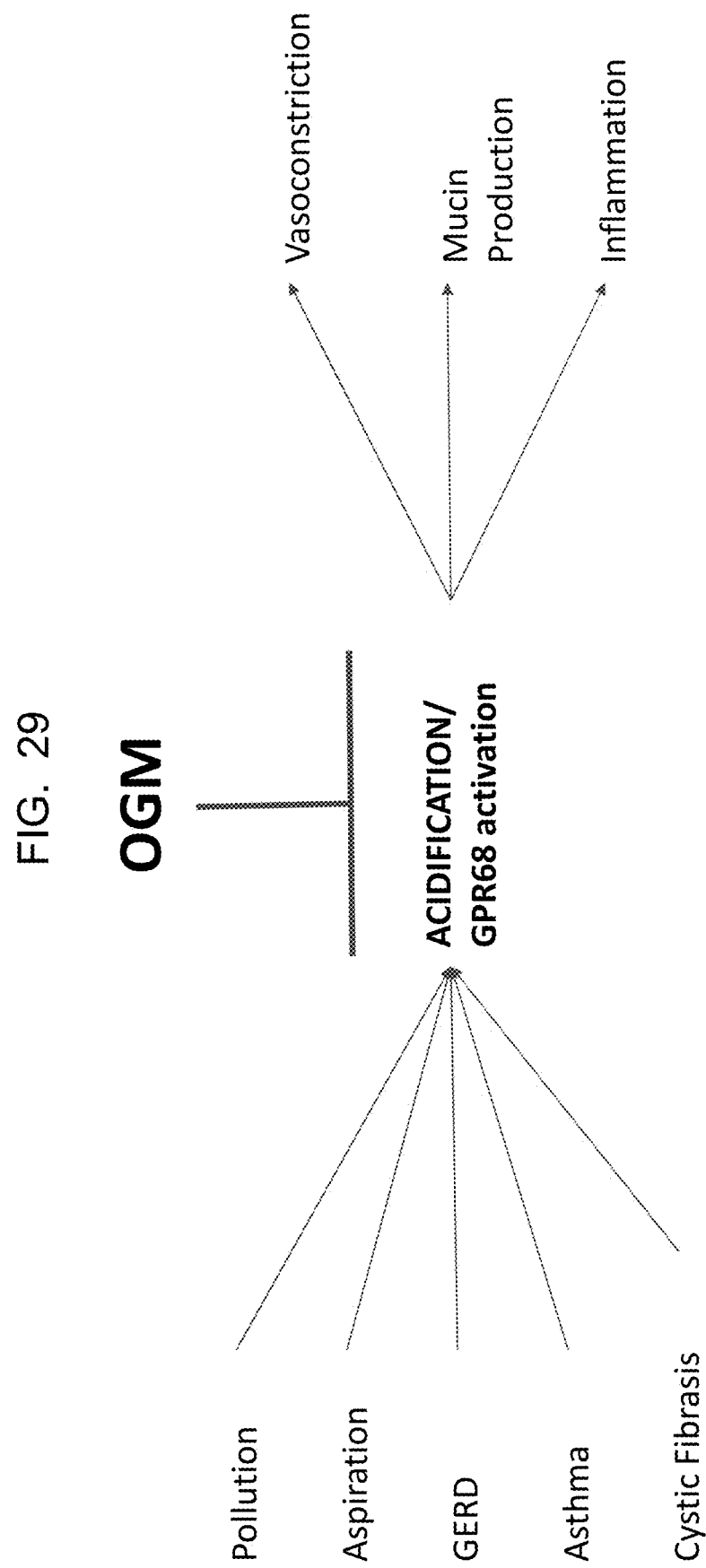
FIG. 29. Schematic of GPR68 activation effects in the lungs.

Further applications which are part of the invention and form embodiments of the invention include, but are not limited to, GERD, aspiration pneumonitis, COPD, ARDS, COVID-19, and the like. GPR68 is involved in sensing acidifications. In the airways this acidification is prevalent in asthmatic populations, those with GERD, some subjects exposed to certain pollutants, cystic fibrosis patients, and persons undergoing ventilation (where almost 90% of patients intubated for 4 or more days suffer from aspiration). Acidification of the mouse lung is a key model of ARDS, resulting in injury of the airway and alveolar epithelium, including type I alveolar epithelial cells, followed by a repair process that involves proliferation of alveolar type II cells, impairment in the alveolar epithelial fluid transport function, resulting in changes in alveolar fluid clearance independently of pulmonary blood flow or vascular filtration, and neutrophil infiltrations. The clinical development of ALI/ARDS typically involves a sudden, severe pulmonary inflammatory injury with the loss of integrity of alveolar-capillary permeability. Similarly, activation of GPR68 caused airway smooth muscles to contract using VASP in response to acidosis (pH 6.8). GPR68 was shown as critical for the inflammatory cascade, as well. See FIG. 29 for a diagram of these effects.

Example 26: Detection of Rs61745752 for Diagnostic Purposes

Finally, given the association of rs61745752 with cancer (FIG. 9) and the functional studies of increased metastatic ability in MCF7 cells expressing the truncation construct (FIG. 14), further applications of the invention include, the diagnostic testing for the SNP rs61745752 (In human genome assembly GRCh38.p12 this variant is on chromosome 14 at position 91234045 coding a change of the nucleotide Cytosine to Adenine) which results in an early truncation of the protein E336X, at the DNA, cDNA, or protein level to make medical care decisions in treatment of neoplasms.

REFERENCES

All references listed below and throughout the specification are hereby incorporated by reference in their entirety.
1. Adams, D. S., Robinson, K. R., Fukumoto, T., Yuan, S., Albertson, R. C., Yelick, P., Kuo, L., McSweeney, M., Levin, M., 2006. Early, H+-V-ATPase-dependent proton flux is necessary for consistent left-right patterning of non-mammalian vertebrates. Development 133, 1657-1671. doi:10.1242/dev.02341.
2. Ahn, S., Nelson, C. D., Garrison, T. R., Miller, W. E., Lefkowitz, R. J., 2003. Desensitization, internalization, and signaling functions of beta-arrestins demonstrated by RNA interference. Proc Natl Acad Sci USA 100, 1740-1744. doi:10.1073/pnas.262789099.
3. Aoki, H, et al. Proton-sensing ovarian cancer G protein-coupled receptor 1 on dendritic cells is required for airway responses in a murine asthma model. PLoS One. 2013 Nov. 11; 8(11): e79985. doi: 10.1371/journal.pone.0079985.
4. Baebler, C. Maeyashiki, P. Busenhart, M. Schwarzfischer, I<. Atrott, S. Lang, M. Spalinger, M. Scharl, G. Rogler, C. de Valliere (2018). A novel OG 1 (GPR68) inhibitor attenuates inflammation in a murine model of acute colitis. 2018 *European Crohn's & Colitis Organization Meeting Abstract* P087
5. Bhujwalla, Z. M., Artemov, D., Aboagye, E., Ackerstaff, E., Gillies, R. J., Natarajan, K., Solaiyappan, M., 2001. The physiological environment in cancer vascularization, invasion and metastasis. Novartis Found. Symp. 240, 23-38; discussion 38.
6. Boonpiyathad T, Sözener Z C, Satitsuksanoa P, Akdis C A. Immunologic Mechanisms in Asthma. Semin Immunol. 2019 December; 46:101333. doi: 10.1016/j.smim.2019.101333.
7. Carroll, R. J., Bastarache, L., Denny, J. C., 2014. R PheWAS: data analysis and plotting tools for phenome-wide association studies in the R environment. Bioinformatics 30, 2375-2376. doi:10.1093/bioinformatics/btu197.
8. Castellone, R. D., Leffler, N. R., Dong, L., Yang, L. V., 2011. Inhibition of tumor cell migration and metastasis by the proton-sensing GPR4 receptor. Cancer Lett. 312, 197-208. doi:10.1016/j.canlet.2011.08.013.
9. Cerami, E., Gao, J., Dogrusoz, U., Gross, B. E., Sumer, S. O., Aksoy, B. A., Jacobsen, A., Byrne, C. J., Heuer, M. L., Larsson, E., Antipin, Y., Reva, B., Goldberg, A. P., Sander, C., Schultz, N., 2012. The cBio cancer genomics portal: an open platform for exploring multidimensional cancer genomics data. Cancer Discov. 2, 401-404. doi:10.1158/2159-8290.CD-12-0095.
10. Chen, B., Dodge, M. E., Tang, W., Lu, J., Ma, Z., Fan, C.-W., Wei, S., Hao, W., Kilgore, J., Williams, N. S., Roth, M. G., Amatruda, J. F., Chen, C., Lum, L., 2009. Small molecule-mediated disruption of Wnt-dependent signaling in tissue regeneration and cancer. Nat. Chem. Biol. 5, 100-107. doi:10.1038/nchembio.137.
11. Chen Y Jl, Huang C W, Lin C S, Chang W H, Sun W H (July 2009) Expression and funct i on of pro ton-sensing G-protein-coupied receptors in inflammatory pain. Molecular *Pain* 5:39
12. Cheng, Z., Garvin, D., Paguio, A., Stecha, P., Wood, K., Fan, F., 2010. Luciferase Reporter Assay System for Deciphering GPCR Pathways. Curr. Chem. Genomics 4, 84-91. doi:10.2174/1875397301004010084.
13. Coakley R D, Grubb B R, Paradiso A M, Gatzy J T, Johnson L G, Kreda S M, O'Neal W K, Boucher R C. Abnormal surface liquid pH regulation by cultured cystic fibrosis bronchial epithelium. Proc Natl Acad Sci USA. 2003 Dec. 23; 100(26):16081-8. Epub 2003 Dec. 10.
14. Cui X, Hartl'lnto Y, Zhang H (February 2017). Advances in multicellular spheroids formation. Journal Royal Society Interface. 14(127): 20160877
15. de Valliere C, Wang Y, Eloranta J J, Vidal S, Clay I, Spalinger M R, Tcymbarevich I, Terhalle A, Ludwig M G, Suply T, Fried M, l<ullak-Ublick G A, Frey-Wagner I, Scharl M, Seuwen I<, Wagner C A, Rogler G (June 2015). G Protein-coupled pH-sensing Receptor OGR1 Is a Regulator of Intestinal Inflammation. *Inflammatory Bowel Dis* 21: 1269-1281
16. de Vallière, C, et al. Hypoxia Positively Regulates the Expression of pH-Sensing G-Protein-Coupled Receptor OGR1 (GPR68). *Cell Mol Gastroenterol Hepatol*. 2016 November; 2(6): 796-810.
17. Denny, J. C., Bastarache, L., Ritchie, M. D., Carroll, R. J., Zink, R., Mosley, J. D., Field, J. R., Pulley, J. M., Ramirez, A. H., Bowton, E., Basford, M. A., Carrell, D. S., Peissig, P. L., Kho, A. N., Pacheco, J. A., Rasmussen, L. V., Crosslin, D. R., Crane, P. K., Pathak, J., Bielinski, S. J., Roden, D. M., 2013. Systematic comparison of phenome-wide association study of electronic medical record data and genome-wide association study data. Nat. Biotechnol. 31, 1102-1110. doi:10.1038/nbt.2749.
18. Denny, J. C., Bastarache, L., Roden, D. M., 2016. Phenome-Wide Association Studies as a Tool to Advance Precision Medicine. Annu. Rev. Genomics Hum. Genet. 17, 353-373. doi:10.1146/annurev-genom-090314-024956.

19. D'Souza C A, Zhao F L, LiX, Xu Y, Dunn S E, Zhang L (February 2016). OGR1/GPR68 Modulates the Severity of Experimental Autoimmune Encephalomyelitis and Regulates Nitric Oxide Production by Macrophages. *PLoS ONE* 11(2): e0148439

20. Gao, J., Aksoy, B. A., Dogrusoz, U., Dresdner, G., Gross, B., Sumer, S. O., Sun, Y., Jacobsen, A., Sinha, R., Larsson, E., Cerami, E., Sander, C., Schultz, N., 2013. Integrative analysis of complex cancer genomics and clinical profiles using the cBioPortal. Sci. Signal. 6, p11. doi: 10.1126/scisignal.2004088.

21. Gayan, S., Teli, A., Dey, T., 2017. Inherent aggressive character of invasive and noninvasive cells dictates the in vitro migration pattern of multicellular spheroid. Sci. Rep. 7, 11527. doi:10.1038/s41598-017-10078-7

22. Glunde, K., Guggino, S. E., Solaiyappan, M., Pathak, A. P., Ichikawa, Y., Bhujwalla, Z. M., 2003. Extracellular acidification alters lysosomal trafficking in human breast cancer cells. Neoplasia 5, 533-545.

23. Hanahan D and Weinberg R A (March 2011). Hallmarks of Cancer: The Next Generation. *Cell*; 144: 646-674.

24. Hao, J., Ao, A., Zhou, L., Murphy, C. K., Frist, A. Y., Keel, J. J., Thorne, C. A., Kim, K., Lee, E., Hong, C. C., 2013. Selective small molecule targeting β-catenin function discovered by in vivo chemical genetic screen. Cell Rep. 4, 898-904. doi:10.1016/j.celrep.2013.07.047.

25. Hill, R. P., De Jaeger, K., Jang, A., Cairns, R., 2001. pH, hypoxia and metastasis. Novartis Found. Symp. 240, 154-65; discussion 165.

26. Horman, S. R., To, J., Lamb, J., Zoll, J. H., Leonetti, N., Tu, B., Moran, R., Newlin, R., Walker, J. R., Orth, A. P., 2017. Functional profiling of microtumors to identify cancer associated fibroblast-derived drug targets. Oncotarget 8, 99913-99930. doi:10.18632/oncotarget.21915.

27. Hu Z W. Zhao Y N, Cheng Y, Guo C Y, Wang X, Li N, Liu J Q, Kang H, Xia G G, Hu P, Zhang P J, Ma J, Liu Y, Zhang C, Su L, Wang G F. Living near a Major Road in Beijing: Association with Lower Lung Function, Airway Acidification, and Chronic Cough. Chin Med J 2016; 129:2184-90.

28. Hunt E B, Sullivan A, Galvin J, MacSharry J, Murphy D M. Gastric Aspiration and Its Role in Airway Inflammation. *Open Respir Med J.* 2018; 12:1-10. Published 2018 Jan. 23. doi:10.2174/1874306401812010000.

29. Jung, H.-Y., Fattet, L., Tsai, J. H., Kajimoto, T., Chang, Q., Newton, A. C., Yang, J., 2019. Apical-basal polarity inhibits epithelial-mesenchymal transition and tumour metastasis by PAR-complex-mediated SNAI1 degradation. *Nat. Cell Biol.* 21, 359-371. doi:10.1038/s41556-019-0291-8.

30. Justus, C. R., Dong, L., Yang, L. V., 2013. Acidic tumor microenvironment and pH-sensing G protein-coupled receptors. Front. Physiol. 4, 354. doi:10.3389/fphys.2013.00354.

31. Kodric, M., Shah, A. N., Fabbri, L. M. & Confalonieri, M. An investigation of airway acidification in asthma using induced sputum: a study of feasibility and correlation. *Am. J. Respir. Crit. Care Med.* 175, 905-910 (2007).

32. Krieger N S, Yao Z, Kyker-Snowman K, Kim M H, Boyce B F, Bushinsky D A (March 2016). Increased bone density in mice lacking the proton receptor OGR1. *Kidney International* 89:565-573.

33. Kuba K, et al. A crucial role of angiotensin converting enzyme 2 (ACE2) in SARS coronavirus-induced lung injury. Nat Med. 2005 August; 11(8):875-9.

34. Kwak, J., Park, O. K., Jung, Y. J., Hwang, B. J., Kwon, S.-H., Kee, Y., 2013. Live image profiling of neural crest lineages in zebrafish transgenic lines. Mol. Cells 35, 255-260. doi:10.1007/s10059-013-0001-5.

35. Li, G., Zhou, Q., Yu, Y., Chen, L., Shi, Y., Luo, J., Benovic, J., Lu, J., Zhou, N., 2012. Identification and characterization of distinct C-terminal domains of the human hydroxycarboxylic acid receptor-2 that are essential for receptor export, constitutive activity, desensitization, and internalization. Mol. Pharmacol. 82, 1150-1161. doi:10.1124/mol.112.081307.

36. Liu C, Li Q, Zhou X, Kolosov V P, Perelman J M. Regulator of G-protein signaling 2 inhibits acid-induced mucin5A C hypersecretion in human airway epithelial cells. Respir Physiol Neurobiol. 2013 Jan. 15; 185(2): 265-71.

37. Lopez-Lazaro M (April 20081. The Warburg effect: why and how do cancer cells activate glycolysis in the presence of oxygen? *Anti-Cancer Agents in Medicinal Chemistry* 8 (3): 305-12.

38. Ludwig, F. T., Schwab, A., Stock, C., 2013. The Na+/H+-exchanger (NHE1) generates pH nanodomains at focal adhesions. J. Cell. Physiol. 228, 1351-1358. doi: 10.1002/jcp.24293.

39. Luttrell, L. M., Lefkowitz, R. J., 2002. The role of beta-arrestins in the termination and transduction of G-protein-coupled receptor signals. J. Cell Sci. 115, 455-465. Marik P. E. Aspiration pneumonitis and aspiration pneumonia. N. Engl. J. Med. 2001:344(9):665-671.

40. Marik P. E. Aspiration pneumonitis and aspiration pneumonia. N. Engl. J. Med. 2001; 344(9):665-671.

41. Marino M L, Pellegrini P, Di Lernia G, DJavaher-Mergny M, Brnjic 5, Zhang X, Hagg M, Linder S, Fais S, Codogno P, De Milito A (August 2012). Autophagy is a protective mechanism for human melanoma cells under acidic stress. *J Biol Chem.* 287(36):30664-76

42. Martinez-Zaguilan, R., Lynch, R. M., Martinez, G. M., Gillies, R. J., 1993. Vacuolar-type H(+)-ATPases are functionally expressed in plasma membranes of human tumor cells. Am. J. Physiol. 265, C1015-29. doi:10.1152/ajpcell.1993.265.4.C1015.

43. Martínez-Zaguilán, R., Martinez, G. M., Gomez, A., Hendrix, M. J., Gillies, R. J., 1998. Distinct regulation of pH in and [Ca2+] in human melanoma cells with different metastatic potential. J. Cell. Physiol. 176, 196-205. doi: 10.1002/(SICI)1097-4652(199807)176:1<196::AID-JCP21>3.0.CO; 2-4.

44. Martínez-Zaguilán, R., Seftor, E. A., Seftor, R. E., Chu, Y. W., Gillies, R. J., Hendrix, M. J., 1996. Acidic pH enhances the invasive behavior of human melanoma cells. Clin. Exp. Metastasis 14, 176-186.

45. Matthews, H., Ranson, M., Kelso, M. J., 2011. Antitumour/metastasis effects of the potassium-sparing diuretic amiloride: an orally active anti-cancer drug waiting for its call-of-duty? Int. J. Cancer 129, 2051-2061. doi:10.1002/ijc.26156.

46. Matute-Bello G, Frevert C W, Martin T R. Animal models of acute lung injury. *Am J Physiol Lung Cell Mol Physiol.* 2008; 295(3):L379-L399. doi:10.1152/ajplung.00010.2008.

47. McLean, L. A., Roscoe, J., Jorgensen, N. K., Gorin, F. A., Cala, P. M., 2000. Malignant gliomas display altered pH regulation by NHE1 compared with nontransformed astrocytes. *Am J Physiol, Cell Physiol* 278, C676-88. doi:10.1152/ajpcell.2000.278.4.C676.
48. Metheny N A, Clouse R E, Chang Y H, Stewart B J, Oliver D A, Kollef M H. Tracheobronchial aspiration of gastric contents in critically ill tube-fed patients: frequency, outcomes, and risk factors. Crit Care Med. 2006.
49. Miraglia, E., Viarisio, D., Riganti, C., Costamagna, C., Ghigo, D., Bosia, A., 2005. Na+/H+ exchanger activity is increased in doxorubicin-resistant human colon cancer cells and its modulation modifies the sensitivity of the cells to doxorubicin. Int. J. Cancer 115, 924-929. doi: 10.1002/ijc.20959.
50. Mochimaru, Y., Azuma, M., Oshima, N., Ichijo, Y., Satou, K., Matsuda, K., Asaoka, Y., Nishina, H., Nakakura, T., Mogi, C., Sato, K., Okajima, F., Tomura, H., 2015. Extracellular acidification activates ovarian cancer G-protein-coupled receptor 1 and GPR4 homologs of zebra fish. Biochem. Biophys. Res. Commun. 457, 493-499. doi:10.1016/j.bbrc.2014.12.105.
51. Monteiro A, Hill R, Pilkington G, Madureira P (December 2017). The Role of Hypoxia in Glioblastoma Invasion. *Cells* 6(4): 45.
52. Nassios, A., Wallner, S., Haferkamp, S., Klingelhöffer, C., Brochhausen, C., Schreml, S., 2019. Expression of proton-sensing G-protein-coupled receptors in selected skin tumors. Exp. Dermatol. 28, 66-71. doi:10.1111/exd.13809.
53. Neri D and Supuran C T (September 2011). Interfering with pH regulation in tumours as a therapeutic strategy. Nature Reviews Drug Discovery 10:767-777
54. Nishisho, T., Hata, K., Nakanishi, M., Morita, Y., Sun-Wada, G.-H., Wada, Y., Yasui, N., Yoneda, T., 2011. The a3 isoform vacuolar type $H^+$-ATPase promotes distant metastasis in the mouse B16 melanoma cells. Mol. Cancer Res. 9, 845-855. doi:10.1158/1541-7786.MCR-10-0449.
55. Oppitz, M., Busch, C., Schriek, G., Metzger, M., Just, L., Drews, U., 2007. Non-malignant migration of B16 mouse melanoma cells in the neural crest and invasive growth in the eye cup of the chick embryo. Melanoma Res. 17, 17-30. doi:10.1097/CMR.0b013e3280114f49.
56. Paganetti. P A, Caroni P, Schwab M E. {December 1988). Glioblastoma infiltration into central nervous system tissue in vitro: involvement of a metalloprotease. *J Cell Biol.* 107(6 Pt 1):2281-91.
57. Parks, S. K., Chiche, J., Pouysségur, J., 2013. Disrupting proton dynamics and energy metabolism for cancer therapy. Nat. Rev. Cancer 13, 611-623. doi:10.1038/nrc3579.
58. Peppicelli, S., Bianchini, F., Torre, E., Calorini, L., 2014. Contribution of acidic melanoma cells undergoing epithelial-to-mesenchymal transition to aggressiveness of non-acidic melanoma cells. Clin. Exp. Metastasis 31, 423-433. doi:10.1007/s10585-014-9637-6.
59. Ren, J., Zhang, L., 2011. Effects of ovarian cancer G protein coupled receptor 1 on the proliferation, migration, and adhesion of human ovarian cancer cells. Chin. Med. J. 124, 1327-1332.
60. Riemann, A., Ihling, A., Thomas, J., Schneider, B., Thews, O., Gekle, M., 2015. Acidic environment activates inflammatory programs in fibroblasts via a cAMP-MAPK pathway. Biochim. Biophys. Acta 1853, 299-307. doi: 10.1016/j.bbamcr.2014.11.022.
61. Rofstad, E. K., Mathiesen, B., Kindem, K., Galappathi, K., 2006. Acidic extracellular pH promotes experimental metastasis of human melanoma cells in athymic nude mice. Cancer Res. 66, 6699-6707. doi:10.1158/0008-5472.CAN-06-0983.
62. Saxena H, Deshpande D A, Tiegs B C, Yan H, Battafarano R J, Burrows W M, Damera G, Panettieri R A, Dubose T D Jr, An S S, Penn R B. The GPCR OGR1 (GPR68) mediates diverse signalling and contraction of airway smooth muscle in response to small reductions in extracellular pH. Br J Pharmacol. 2012 June; 166(3):981-90.
63. Schneider, L., Stock, C.-M., Dieterich, P., Jensen, B. H., Pedersen, L. B., Satir, P., Schwab, A., Christensen, S. T., Pedersen, S. F., 2009. The Na+/H+ exchanger NHE1 is required for directional migration stimulated via PDGFR-alpha in the primary cilium. J. Cell Biol. 185, 163-176. doi:10.1083/jcb.200806019.
64. Schriek, G., Oppitz, M., Busch, C., Just, L., Drews, U., 2005. Human SK-Mel 28 melanoma cells resume neural crest cell migration after transplantation into the chick embryo. Melanoma Res. 15, 225-234.
65. Sennoune, S. R., Bakunts, K., Martínez, G. M., Chua-Tuan, J. L., Kebir, Y., Attaya, M. N., Martínez-Zaguilán, R., 2004. Vacuolar H+-ATPase in human breast cancer cells with distinct metastatic potential: distribution and functional activity. Am J Physiol, Cell Physiol 286, C1443-52. doi:10.1152/ajpcell.00407.2003.
66. Sente, A., Peer, R., Srivastava, A., Baidya, M., Lesk, A. M., Balaji, S., Shukla, A. K., Babu, M. M., Flock, T., 2018. Molecular mechanism of modulating arrestin conformation by GPCR phosphorylation. *Nat. Struct. Mol. Biol.* 25, 538-545. doi:10.1038/s41594-018-0071-3.
67. Shimizu Y, Dobashi K, Mori M. Exhaled breath marker in asthma patients with gastroesophageal reflux disease. *J Clin Biochem Nutr,* 2007; 41(3):147-153. doi:10.3164/jcbn.2007020
68. Singh, L. S., Berk, M., Oates, R., Zhao, Z., Tan, H., Jiang, Y., Zhou, A., Kirmani, K., Steinmetz, R., Lindner, D., Xu, Y., 2007. Ovarian cancer G protein-coupled receptor 1, a new metastasis suppressor gene in prostate cancer. J Natl Cancer Inst 99, 1313-1327. doi:10.1093/jnci/djm107.
69. Sinnberg, T., Levesque, M. P., Krochmann, J., Cheng, P. F., Ikenberg, K., Meraz-Torres, F., Niessner, H., Garbe, C., Busch, C., 2018. Wnt-signaling enhances neural crest migration of melanoma cells and induces an invasive phenotype. Mol. Cancer 17, 59. doi:10.1186/s12943-018-0773-5.
70. Son Y G, Shin J, Ryu H G. Pneumonitis and pneumonia after aspiration. J Dent Anesth Pain Med. 2017 March; 17(1):1-12. doi: 10.17245/jdapm.2017.17.1.1
71. Stewart, R. A., Arduini, B. L., Berghmans, S., George, R. E., Kanki, J. P., Henion, P. D., Look, A. T., 2006. Zebrafish foxd3 is selectively required for neural crest specification, migration and survival. Dev. Biol. 292, 174-188. doi:10.1016/j.ydbio.2005.12.035.
72. Stock, C., Gassner, B., Hauck, C. R., Arnold, H., Mally, S., Eble, J. A., Dieterich, P., Schwab, A., 2005. Migration of human melanoma cells depends on extracellular pH and Na+/H+ exchange. J Physiol (Lond) 567, 225-238. doi:10.1113/jphysiol.2005.088344.
73. Stock, C., Mueller, M., Kraehling, H., Mally, S., Noel, J., Eder, C., Schwab, A., 2007. pH nanoenvironment at the surface of single melanoma cells. Cell. Physiol. *Biochem.* 20, 679-686. doi:10.1159/000107550.
74. Stüwe, L., Müller, M., Fabian, A., Waning, J., Mally, S., Noël, J., Schwab, A., Stock, C., 2007. pH dependence of melanoma cell migration: protons extruded by NHE1 dominate protons of the bulk solution. J Physiol (Lond) 585, 351-360. doi:10.1113/jphysiol.2007.145185.

75. Suresh M V, et al. Hypoxia-Inducible Factor (HIF)-1α Promotes Inflammation and Injury Following Aspiration-Induced Lung Injury in Mice. Shock. 2019 December; 52(6):612-621.
76. Vandenberg, L. N., Morrie, R. D., Adams, D. S., 2011. V-ATPase-dependent ectodermal voltage and pH regionalization are required for craniofacial morphogenesis. Dev. Dyn. 240, 1889-1904. doi:10.1002/dvdy.22685.
77. Vander Heiden, M. G., Cantley, L. C., Thompson, C. B., 2009. Understanding the Warburg effect: the metabolic requirements of cell proliferation. Science 324, 1029-1033. doi:10.1126/science.1160809.
78. Warburg, On the origin of cancer cells. Science 123 (3191): 309-14.
79. Webb, B. A., Chimenti, M., Jacobson, M. P., Barber, D. L., 2011. Dysregulated pH: a perfect storm for cancer progression. Nat. Rev. Cancer 11, 671-677. doi:10.1038/nrc3110.
80. Wei, W.-C., Bianchi, F., Wang, Y.-K., Tang, M.-J., Ye, H., Glitsch, M. D., 2018. Coincidence Detection of Membrane Stretch and Extracellular pH by the Proton-Sensing Receptor OGR1 (GPR68). Curr. Biol. 28, 3815-3823.e4. doi:10.1016/j.cub.2018.10.046.
81. Wei, W.-C., Huang, W.-C., Lin, Y.-P., Becker, E. B. E., Ansorge, O., Flockerzi, V., Conti, D., Cenacchi, G., Glitsch, M. D., 2017. Functional expression of calcium-permeable canonical transient receptor potential 4-containing channels promotes migration of medulloblastoma cells. J Physiol (Lond) 595, 5525-5544. doi:10.1113/JP274659.
82. Weiß, K. T., Fante, M., Köhl, G., Schreml, J., Haubner, F., Kreutz, M., Haverkampf, S., Berneburg, M., Schreml, S., 2017. Proton-sensing G protein-coupled receptors as regulators of cell proliferation and migration during tumor growth and wound healing. Exp. Dermatol. 26, 127-132. doi:10.1111/exd.13209.
83. Westerfield, M., 2000. The zebrafish book: a guide for the laboratory use of zebrafish, 4th ed. University of Oregon Press, Eugene, OR.
84. Wiley, S. Z., Sriram, K., Liang, W., Chang, S. E., French, R., McCann, T., Sicklick, J., Nishihara, H., Lowy, A. M., Insel, P. A., 2018. GPR68, a proton-sensing GPCR, mediates interaction of cancer-associated fibroblasts and cancer cells. FASEB J. 32, 1170-1183. doi:10.1096/fj.201700834R.
85. Wiley, S. Z., Sriram, K., Salmerón, C., Insel, P. A., 2019. GPR68: an emerging drug target in cancer. Int. J. Mol. Sci. 20. doi:10.3390/ijms20030559.
86. Williams, C. H., Hempel, J. E., Hao, J., Frist, A. Y., Williams, M. M., Fleming, J. T., Sulikowski, G. A., Cooper, M. K., Chiang, C., Hong, C. C., 2015. An in vivo chemical genetic screen identifies phosphodiesterase 4 as a pharmacological target for hedgehog signaling inhibition. Cell Rep. 11, 43-50. doi:10.1016/j.celrep.2015.03.001.
87. Wojtkowlak J W, Rothberg J M, Kumar V, Schramm K J, Halter E, Proemsey J B, Lloyd M C, Sloane B F, Gillies R J (August 2012). Chronic autophagy is a cellular adaptation to tumor acidic pH microenvironments, *Cancer Res*, 1 5; 72(16):3938-47.
88. Xu, J., Mathur, J., Vessières, E., Hammack, S., Nonomura, K., Favre, J., Grimaud, L., Petrus, M., Francisco, A., Li, J., Lee, V., Xiang, F.-L., Mainquist, J. K., Cahalan, S. M., Orth, A. P., Walker, J. R., Ma, S., Lukacs, V., Bordone, L., Bandell, M., Patapoutian, A., 2018. GPR68 senses flow and is essential for vascular physiology. Cell 173, 762-775.e16. doi:10.1016/j.cell.2018.03.076.
89. Yu, P. B., Hong, C. C., Sachidanandan, C., Babitt, J. L., Deng, D. Y., Hoyng, S. A., Lin, H. Y., Bloch, K. D., Peterson, R. T., 2008. Dorsomorphin inhibits BMP signals required for embryogenesis and iron metabolism. Nat. Chem. Biol. 4, 33-41. doi:10.1038/nchembio.2007.54.
90. Zhou, X. E., He, Y., de Waal, P. W., Gao, X., Kang, Y., Van Eps, N., Yin, Y., Pal, K., Goswami, D., White, T. A., Barty, A., Latorraca, N. R., Chapman, H. N., Hubbell, W. L., Dror, R. O., Stevens, R. C., Cherezov, V., Gurevich, V. V., Griffin, P. R., Ernst, O. P., Xu, H. E., 2017. Identification of Phosphorylation Codes for Arrestin Recruitment by G Protein-Coupled Receptors. Cell 170, 457-469.e13. doi:10.1016/j.cell.2017.07.002.
91. Zhu, H., Guo, S., Zhang, Y., Yin, J., Yin, W., Tao, S., Wang, Y., Zhang, C., 2016. Proton-sensing GPCR-YAP Signalling Promotes Cancer-associated Fibroblast Activation of Mesenchymal Stem Cells. Int. J. Biol. Sci. 12, 389-396. doi:10.7150/ijbs.13688.

The invention claimed is:

1. A method of treating or preventing a malignancy in a mammalian subject in need thereof, comprising administering to the subject

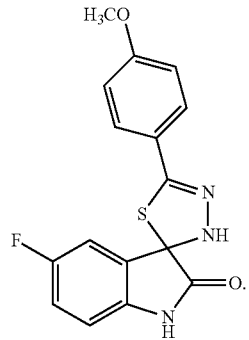

2. The method of claim 1, wherein the malignancy is selected from the group consisting of glioblastoma, medulloblastoma, neuroendocrine prostate cancer, melanoma, skin cancer, breast cancer, ovarian cancer, kidney cancer, and lung cancer.

3. The method of claim 1, which further comprises administering to the mammalian subject in need thereof at least one additional therapeutic agent.

4. The method of claim 3, wherein the at least one additional therapeutic agent is an anticancer agent.

5. The method of claim 4, wherein the anticancer agent is Temozolomide.

* * * * *